US010406211B2

(12) United States Patent
Newman et al.

(10) Patent No.: US 10,406,211 B2
(45) Date of Patent: Sep. 10, 2019

(54) METHODS AND SYSTEM FOR INTERFERING WITH VIABILITY OF BACTERIA AND RELATED COMPOUNDS AND COMPOSITIONS

(71) Applicants: CALIFORNIA INSTITUTE OF TECHNOLOGY, Pasadena, CA (US); THE TRUSTEES OF DARTMOUTH COLLEGE, Hanover, NH (US)

(72) Inventors: Dianne K. Newman, Brookline, MA (US); Ryan C. Hunter, Little Canada, MN (US); George A O'Toole, Hanover, NH (US)

(73) Assignees: CALIFORNIA INSTITUTE OF TECHNOLOGY, Pasadena, CA (US); TRUSTEES OF DARTMOUTH COLLEGE, Hanover, NH (US)

( * ) Notice: Subject to any disclaimer, the term of this patent is extended or adjusted under 35 U.S.C. 154(b) by 0 days.

(21) Appl. No.: 14/830,673

(22) Filed: Aug. 19, 2015

(65) Prior Publication Data
US 2016/0058843 A1 Mar. 3, 2016

Related U.S. Application Data

(63) Continuation-in-part of application No. 13/456,172, filed on Apr. 25, 2012.

(60) Provisional application No. 62/039,385, filed on Aug. 19, 2014, provisional application No. 61/478,746, filed on Apr. 25, 2011.

(51) Int. Cl.
*A01N 37/18* (2006.01)
*A01N 43/707* (2006.01)
*A61K 38/38* (2006.01)
*A61K 31/53* (2006.01)
*C12N 1/20* (2006.01)
*C12N 1/36* (2006.01)

(52) U.S. Cl.
CPC .............. *A61K 38/38* (2013.01); *A01N 37/18* (2013.01); *A01N 43/707* (2013.01); *A61K 31/53* (2013.01); *C12N 1/20* (2013.01); *C12N 1/36* (2013.01)

(58) Field of Classification Search
CPC ........ A61K 38/38; A61K 31/53; A01N 37/18; A01N 43/707; C12N 1/20; C12N 1/36
See application file for complete search history.

(56) References Cited

U.S. PATENT DOCUMENTS

| 5,223,409 | A | 6/1993 | Ladner et al. | |
| 2002/0102628 | A1 | 8/2002 | Phibbs et al. | |
| 2003/0022349 | A1 | 1/2003 | Ausubel et al. | |
| 2010/0035992 | A1 | 2/2010 | Bhushan et al. | |
| 2011/0189260 | A1* | 8/2011 | Herr et al. | 424/447 |
| 2013/0022578 | A1* | 1/2013 | Newman | C12N 1/20 424/93.4 |
| 2017/0266215 | A1 | 9/2017 | Newman et al. | |
| 2017/0275597 | A1 | 9/2017 | Newman et al. | |
| 2017/0283763 | A1 | 10/2017 | Newman et al. | |

FOREIGN PATENT DOCUMENTS

| EP | 2702141 B1 | 3/2014 |
| WO | 2012/149058 A2 | 11/2012 |
| WO | 2017/165578 A1 | 9/2017 |

OTHER PUBLICATIONS

Avery A.M. et al., "Iron Blocks the Accumulation and Activity of Tetracyclines in Bacteria", Antimicrobial Agents and Chemotherapy, May 2004, vol. 48, No. 5, pp. 1892-1894.*
Singh P. K. et al., "A component of innate immunity prevents bacterial biofilm development", Nature, May 2002, vol. 417, pp. 552-555.*
O'May C. Y. et al., "Iron-binding compounds impair Pseudomonas aeruginosa biofilm formation, especially under anaerobic conditions", Journal of Medical Microbiology, 2009, vol. 58, pp. 765-773. (Year: 2009).*
European Examination Report issued for European Patent Application No. 12775958.7, dated Jan. 29, 2016. 8 pages.
European Examination Report issued for European Patent Application No. 12775958.7, dated Nov. 14, 2016. 6 pages.
International Preliminary Report on Patentability issued for International Patent Application PCT/US2012/035052, filed Apr. 25, 2012 in the name of California Institute of Technology et al. dated Nov. 7, 2013. 9 pages.
Non-Final Office Action issued for U.S. Appl. No. 12/548,362, filed Aug. 26, 2009 on behalf of California Institute of Technology, dated Jun. 29, 2016. 10 pages.
Abdul Rahim S., et al., "Studies of Binary Complexes of Metal Ions with 2,2-Bipyridyl by Potentiometry," Chemical Science Transactions, 2015, vol. 4 (1), 5 pages.
Adams et al. "PHENIX: a comprehensive Python-based system for macromolecular structure solution" *Acta Crystallographica Section D—Biological Crystallography, International Union of Crystallography.* 2010. vol. D66. pp. 231-221. 9 pages.
Aendekerk S., et al., "The MexGHI-OpmD Multidrug Efflux Pump Controls Growth, Antibiotic Susceptibility and Virulence in Pseudomonas Aeruginosa via 4-Quinolone-Dependent Cell-to-Cell Communication," Microbiology, Apr. 2005, vol. 151 (Pt 4), 13 pages.

(Continued)

*Primary Examiner* — Satyendra K Singh
(74) *Attorney, Agent, or Firm* — Steinfl + Bruno LLP

(57) ABSTRACT

Provided herein are methods and systems for interfering with viability of bacteria and related compounds and compositions.

22 Claims, 16 Drawing Sheets

Specification includes a Sequence Listing.

(56) References Cited

OTHER PUBLICATIONS

Afonine et al. "Towards automated crystallographic structure refinement with phenix.refine" *Acta Crystallographica Section D, International Union of Crystallography*.2012. vol. D68. pp. 352-367. 16 pages.
Alibert-Franco et al., "Efflux Mechanism, an Attractive Target to Combat Multidrug Resistant Plasmodium Falciparum and Pseudomonas Aeruginosa," Current Medicinal Chemistry, 2009, vol. 16 (3), 17 pages.
Altschul et al. "Gapped BLAST and PSI-BLAST: a new generation of protein database search programs" *Nucleic Acids Research, Oxford University Press*.1997. vol. 25, No. 17. pp. 3389-3402. 14 pages.
Anand et al. "Structure and Mechanism of Lysine-specific Demethylase Enzymes" *Journal of Biological Chemistry, The American Society for Biochemistry and Molecular Biology Inc*.Dec. 7, 2007. vol. 282, No. 49. pp. 35425-35429. 6 pages.
Babin et al. "SutA is a bacterial transcription factor expressed during slow growth in Pseudomonas aeruginosa" *Proceedings of the National Academy of Sciences, National Academy of Sciences*.Jan. 19, 2016.vol. 113, No. 5. pp. E597-E605. 9 pages.
Baker E.N., et al., "Three-Dimensional Structure of Lactoferrin in Various Functional States," Advances in Experimental Medicine and Biology, 1994, vol. 357, 12 pages.
Bange et al. "Recovery of Mycobacteria from Patients with Cystic Fibrosis" *Journal of Clinical Microbiology, American Society for Microbiology*.Nov. 1999. vol. 37, No. 11. pp. 3761-3763. 3 pages.
Barua P.K., et al., "Effect of Iron Limitation on Bacteroids Gingivalis," Oral Microbiology and Immunology, Oct. 1990, vol. 5 (5), 8 pages.
Bashiri et al. "Production of recombinant proteins in Mycobacterium smegmatis for structural and functional studies" *Protein Science, The Protein Society*.2015. vol. 24, No. 1. pp. 1-10. 10 pages.
Baxendale J.H., et al., "The Kinetics of Formation and Dissociation of the Ferrous Trisdipyridyl Ion," Transactions of the Faraday Society, 1950, vol. 46, 9 pages.
Baynes R. D., et al., "Effects of Ferrous and Ferric Chelators on Transferrin-Iron-Macrophage Interactions," American Journal of Hematology, Sep. 1988, vol. 29 (1), abstract, 1 page.
Bjarnsholt et al. "Pseudomonas aeruginosa tolerance to tobramycin, hydrogen peroxide and polymorphonuclear leukocytes is quorum-sensing dependent" *Microbiology, Microbiological Society*.2005. vol. 151. pp. 373-383. 11 pages.
Bjarnsholt et al. "The in-vivo biofilm" *Trends in Microbiology, Cell Press*.Sep. 2013. vol. 21, No. 9. pp. 466-474. 9 pages.
Bolte et al. "A guided tour into subcellular colocalization analysis in light microscopy." *Journal of Microscopy, The Royal Microscopical Society*.Dec. 2006. vol. 224 (Pt 3). pp. 213-232. 20 pages.
Borriello et al. "Oxygen Limitation Contributes to Antibiotic Tolerance of Pseudomonas aeruginosa in Biolfilms" *Antimicrobial Agents and Chemotherapy, American Society for Microbiology*.Jul. 2004. vol. 48, No. 7. pp. 2659-2664. 6 pages.
Bradford et al. "A Rapid and Sensitive Method for the Quantitation of Microgram Quantities of Protein Utilizing the Principle of Protein-Dye Binding" *Analytical Biochemistry, Academic Press Inc*.1976. vol. 72. pp. 248-254. 7 pages.
Brandon et al. "The determination of the stability constant for the iron(II) complex of the biochelator pyridine-2,6-bis(monothiocarboxylic acid)" *Biodegradation, Kluwer Academic Publishers*.2003. vol. 14. pp. 73-82. 10 pages.
Breuer W., et al., "Iron Acquired From Transferrin by K562 Cells Is Delivered Into a Cytoplasmic Pool of Chelatable Iron(II)," The Journal of Biological Chemistry, Oct. 1995, vol. 270 (41), 8 pages.
Briard et al. "Pseudomonas aeruginosa manipulates redox and iron homeostasis of its microbiota partner Aspergillus fumigatus via phenazines" *Scientific Reports, Nature Publishing Group*.Feb. 10, 2015. vol. 5, No. 8220. pp. 1-13. 13 pages.
Brown C.T., et al., "Evolutionary Comparisons Suggest Many Novel cAMP Response Protein Binding Sites in *Escherichia coli*," Proceedings of the National Academy of Sciences of the United States of America, Feb. 2004, vol. 101 (8), 6 pages.
Bus J.S., et al., "Paraquat: Model for Oxidant-initiated Toxicity," Environmental Health Perspectives, Apr. 1984, vol. 55, 10 pages.
Carrell T., et al., "A Novel Procedure for the Synthesis of Libraries Containing Small Organic Molecules," Angewandte Chemie International Edition in English, Nov. 1994, vol. 33 (20), 3 pages.
Carrell T., et al., "A Solution-Phase Screening Procedure for the Isolation of Active Compounds from a Library of Molecules," Angewandte Chemie International Edition in English, Nov. 1994, vol. 33 (20), 4 pages.
Chater K.F., "Streptomyces Inside-out: A New Perspective on the Bacteria that Provide us with Antibiotics," Philosophical Transactions of the Royal Society of London. Series B, Biological Sciences, May 2006, vol. 361 (1469), 8 pages.
Cho C.Y., et al., "An Unnatural Biopolymer," Science, Sep. 1993, vol. 261 (5126), 3 pages.
Cloos et al. "Erasing the methyl mark: histone demethylases at the center of cellular differentiation and disease" *Genes and Development, Cold Spring Harbor Laboratory Press*.2008. vol. 22. pp. 1115-1140. 27 pages.
Cohen et al. "Oligoribonuclease is a central feature of cyclic diguanylate signaling in Pseudomonas aeruginosa" *Proceedings of the National Academy of Sciences, National Academy of Sciences*. Sep. 8, 2015. vol. 112, No. 36. pp. 11359-11364. 6 pages.
Costa et al. "Enzymatic Degradation of Phenazines Can Generate Energy and Protect Sensitive Organisms from Toxicity" *mBio, American Society of Microbiology*. Nov./Dec. 2015. vol. 6, No. 6. pp. 1-10. 10 pages.
Costa et al. "Pyocyanin degradation by a tautomerizing demethylase inhibits Pseudomonas aeruginosa biofilms" *Science, American Association for the Advancement of Science*.Dec. 8, 2016. vol. 355, No. 6321. pp. 170-173. 5 pages.
Cull M.G., et al., "Screening for Receptor Ligands using Large Libraries of Peptides Linked to the C Terminus of the Lac Repressor," Proceedings of the National Academy of Sciences of the United States of America, 1992, vol. 89 (5), 5 pages.
Cundliffe E., "How Antibiotic-Producing Organisms Avoid Suicide," Annual Review of Microbiology, 1989, vol. 43, 27 pages.
Cwirla S.E., et al., "Peptides on Phage: A Vast Library of Peptides for Identifying Ligands," Proceedings of the National Academy of Sciences of the United States of America, Aug. 1990, vol. 87 (16), 5 pages.
Czarnik A.W, "Encoding Methods for Combinatorial Chemistry," Current Opinion in Chemical Biology, Jun. 1997, vol. 1 (1), 7 pages.
Das et al. "Phenazine production enhances extracellular DNA release via hydrogen peroxide generation in Pseudomonas aeruginosa" *Communicative and Integrative Biology,Landes Bioscience*.2013. vol. 6, No. 3. pp. e23570-1-e23570-4. 4 pages.
Das et al. "Phenazine virulence factor binding to extracellular DNA is important for Pseudomonas aeruginosa biofilm formation" *Scientific Reports, Nature Publishing Group*.Feb. 11, 2015.vol. 5, No. 8398. pp. 1-9. 9 pages.
Das et al. "Pyocyanin Promotes Extracellular DNA Release in Pseudomonas aeruginosa" *PLOS One, Public Library of Science*. Oct. 2012. vol. 7, No. 10. pp. 1-9. 9 pages.
Das et al. "Pyocyanin Facilitates Extracellular DNA Binding to Pseudomonas aeruginosa Influencing Cell Surface Properties and Aggregation" *PLOS One, Public Library of Science*.Mar. 11, 2013. vol. 8, No. 3. 11 pages.
Dasgupta et al. "Expression Systems for Study of Mycobacterial Gene Regulation and Development of Recombinant BCG Vaccines" *Biochemical and Biophysical Research Communications, Academic Press*.1998. vol. 246. pp. 797-804. 8 pages.
Davies D.G., et al., "The Involvement of Cell-to-cell Signals in the Development of a Bacterial Biofilm," Science, Apr. 1998, vol. 280 (5361), 4 pages.
De La Fuente-Nunez et al. "Bacterial biofilm development as a multicellular adaptation: antibiotic resistance and new therapeutic strategies" *Current Opinion in Microbiology, Elsevier*.2013. vol. 16. pp. 580-589. 9 pages.

(56) References Cited

OTHER PUBLICATIONS

Devlin J.J., et al., "Random Peptide Libraries: A Source of Specific Protein Binding Molecules," Science, Jul. 1990, vol. 249 (4967), 3 pages.

Dewitt S.H., et al., "Diversomers: An Approach to Nonpeptide, Nonoligomeric Chemical Diversity," Proceedings of the National Academy of Sciences of the United States of America, Aug. 1993, vol. 90 (15), 5 pages.

Dhall et al. "Generating and Reversing Chronic Wounds in a Diabetic Mice by Manipulating Wound Redox Parameters" *Journal of Diabetes Research, Hindawi Publishing Corporation*.Dec. 2014. vol. 2014, No. 562625. pp. 1-18. 19 pages.

Dias M.V., et al., "Chorimate Synthase: An Attractive Target for Drug Development Against Orphan Diseases," Current Drug Targets, 2007, vol. 8 (3), 8 pages.

Dietrich et al. "Bacterial Community Morphogenesis Is Intimately Linked to the Intracellular Redox State" *Journal of Bacteriology, American Society of Microbiology*.Apr. 2013. vol. 195, No. 7. pp. 1371-1380. 10 pages.

Diggle et al. "The Pseudomonas aeruginosa quinolone signal molecule overcomes the cell density-dependency of the quorum sensing hierarchy, regulates rhl-dependent genes at the onset of stationary phase and can be produced in the absence of LasR" *Molecular Microbiology, Blackwell Publishing Ltd*.2003. vol. 50, No. 1. pp. 29-43. 15 pages.

Ding et al. "The Redox State of the [2Fe—2S] Clusters in SoxR Protein Regulates Its Activity as a Transcription Factor" *The Journal of Biological Chemistry, American Society for Biochemistry and Molecular Biology Inc*.Dec. 27, 1996. vol. 271, No. 52. pp. 33173-33175. 4 .

Kummerli et al. "Viscous medium promotes cooperation in pathogenic bacterium Pseudomonas aeruginosa" *Proceedings of the Royal Society, The Royal Society*.2009. vol. 276. pp. 3531-3538. 8 pages.

Schneider et al. "NIH Image to ImageJ: 25 years of Image Analysis" *Natural Methods, Nature Publishing Group*.Jul. 2012. vol. 9, No. 7. pp. 671-675. 12 pages.

Driscoll et al. "The Epidemiology, Pathogenesis, and Treatment of Pseudomonas aeruginosa Infections" *Drugs, Adis Data Information BV*.2007. vol. 67, No. 3. pp. 351-368. 18 pages.

Eiamphungporn W., et al., "Agrobacterium tumefaciens soxR is Involved in Superoxide Stress Protection and also Directly Regulates Superoxide-Inducible Expression of itself and a Target Gene," Journal of Bacteriology, Dec. 2006, vol. 188 (24), 5 pages.

Emerson et al. "Pseudomonas Aeruginosa and Other Predictors of Mortality and Morbidity in Young Children with Cystic Fibrosis" *Pediatric Pulmonology, Wiley-Liss Inc*.2002. vol. 34. pp. 91-100. 10 pages.

Emsley et al. "Features and development of Coot" *Acta Crystallographica Section D—Biological Crystallography, International Union of Crystallography*. 2010. vol. D66. pp. 486-501. 16 pages.

Erb E., et al., "Recursive Deconvolution of Combinatorial Chemical Libraries," Proceedings of the National Academy of Sciences of the United States of America, Nov. 1994, vol. 91 (24), 5 pages.

Evans et al. "How good are my data and what is the resolution?" *Acta Crystallographica Section D—Biological Crystallography, International Union of Crystallography*.2013. vol. D69. pp. 1204-1214. 12 pages.

Evans, Philip. "Scaling and assessment of data quality" *Acta Crystallographica Section D—Biological Crystallography, International Union of Crystallography*.2006. vol. D62. pp. 72-82. 11 pages.

Evans, Philip R. "An introduction to data reduction: space-group determination, scaling and intensity statistics" *Acta Crystallographica Section D—Biological Crystallography. International Union of Crystallography*.2011. vol. D67. pp. 282-292. 11 pages.

Extended European Search Report for European Application No. 12775958.7, dated Dec. 5, 2014, 8 pages.

Felici F., et al., "Selection of Antibody Ligands from a Large Library of Oligopeptides Expressed on a Multivalent Exposition Vector," Journal of Molecular Biology, Nov. 1991, vol. 222 (2), 10 pages.

Fernandes P.B., "Technological Advances in High-throughput Screening," Current Opinion in Chemical Biology, Oct. 1998, vol. 2 (5), 7 pages.

Final Office Action for U.S. Appl. No. 12/548,362, dated Dec. 5, 2012, 9 pages.

Final Office Action for U.S. Appl. No. 12/548,362, dated Sep. 10, 2015, 30 pages.

Final Office Action for U.S. Appl. No. 13/456,172, dated Aug. 21, 2014, 20 pages.

Floriano B., et al., "AfsR is a Pleiotropic but Conditionally Required Regulatory Gene for Antibiotic Production in Streptomyces Coelicolor A3(2)," Molecular MicroBiology, Jul. 1996, vol. 21 (2), 12 pages.

Fodor S.P., et al., "Multiplexed Biochemical Assays with Biological Chips," Nature, Aug. 1993, vol. 364 (6437), 2 pages.

Friedman L., et al., "Genes Involved in Matrix Formation in Pseudomonas Aeruginosa PA14 Biofilms," Molecular MicroBiology, Feb. 2004, vol. 51 (3), 16 pages.

Gallop M.A., et al., "Applications of Combinatorial Technologies to Drug Discovery. 1. Background and Peptide Combinatorial Libraries," Journal of Medical Chemistry, Apr. 1994, vol. 37 (9), 19 pages.

Gibbs C.R., et al., "Characterization and Application of Ferrozine Iron Reagent as a Ferrous Iron Indicator," Analytical Chemistry, Jul. 1976, vol. 48 (8), 5 pages.

Glasser et al. "Phenazine redox cycling enhances anaerobic survival in Pseudomonas aeruginosa by facilitating generation of ATP and a proton-motive force" *Molecular Microbiology, John Wiley & Sons Ltd*.2014. vol. 92, No. 2. pp. 399-412. 14 pages.

Gohain N., "Studies on the Structure and Function of Phenazine Modifying Enzymes PhzM and PhzS involved in the Biosynthesis of Pyocyanin," Ph.D. Thesis Dissertation submitted in 2008 to Max Planck Institute for Molecular Physiology & Department of Chemistry, University of Dortmund, Germany, 2008, 143 pages.

Goldenzweig et al. "Automated Structure- and Sequence-Based Design of Proteins for High Bacterial Expression and Stability" *Molecular Cell, Cell Press*.2016. vol. 63. pp. 337-346. 11 pages.

Goodwin J. F., et al., "Chelation of Ferrous Sulphate Solutions by Desferrioxamine B," Nature, Jan. 1965, vol. 205, 3 pages.

Grahl et al. "Ch 3.—The Yin and Yang of Phenazine Physiology" *Microbial Phenazines, Springer-Verlag Berlin Heidelberg*.2013. pp. 43-69. 28 pages.

Gutteridge et al. "Understanding nature's catalytic toolkit" *Trends in Biochemical Sciences, Elsevier*.Nov. 2005. vol. 30, No. 11. pp. 622-629. 8 pages.

Hagel et al. "Biochemistry and occurrence of O-demethylation in plant metabolism" *frontiers in Physiology, Frontiers Media S.A*.Jul. 2010. vol. 1, No. 14. pp. 1-7. 7 pages.

Hassan et al. "Mechanism of the Antibiotic Action of Pyocyanine" *Journal of Bacteriology, American Society of Microbiology*.Jan. 1980. vol. 141, No. 1. pp. 156-163. 8 pages.

Headd et al. "Use of knowledge-based restraints in phenix.refine to improve macromolecular refinement at low resolution" *Acta Crystallographica Section D: Biological Crystallography, International Union of Crystallography*.Apr. 2012. vol. 68 (part 4). pp. 381-390. 17 pages.

Hidalgo E., et al., "The Redox-regulated soxR Protein Acts From a Single DNA Site as a Repressor and an Allosteric Activator," The Embo Journal, May 1998, vol. 17 (9), 2629-2636. 8 pages.

Holby et al. "Pseudomonas aeruginosa biofilms in cystic fibrosis" *Future Microbiology, Future Medicine Ltd*.Nov. 2010. vol. 5, No. 11. pp. 1663-1674. 18 pages.

Houghten R.A., et al., "The Use of Synthetic Peptide Combinatorial Libraries for the Identification of Bioactive Peptides," Biotechniques, Sep. 1992, vol. 13 (3), 10 pages.

Huang J., et al., "Global Analysis of Growth Phase Responsive Gene Expression and Regulation of Antibiotic Biosynthetic Pathways in Streptomyces Coelicolor Using DNA Microarrays," Genes & Development, Dec. 2001, vol. 15 (23), 10 pages.

(56) References Cited

OTHER PUBLICATIONS

Hunter et al. "Ferrous Iron is a Significant Component of Bioavailable Iron in Cystic Fibrosis Airways" *mBio, American Society of Microbiology*.Jul./Aug. 2013. vol. 4, No. 4. pp. 1-8. 8 pages.

International Preliminary Report on Patentability for International Application No. PCT/US2017/023688 filed on Mar. 22, 2017 on behalf of California Institute of Technology dated Sep. 25, 2018 15 pages.

International Search Report for International Application No. PCT/US2017/023688, filed on Mar. 22, 2017, on behalf of California Institute of Technology, dated Jun. 30, 2017. 6 pages.

Johnson et al. "Hidden Markov model speed heuristic and iterative HMM search procedure" *BMC Bioinformatics, BioMed Central Ltd*.2010. vol. 11, No. 431. pp. 1-8. 8 pages.

Jones et al. "Determination of Submicromolar Concentrations of Formaldehyde by Liquid Chromatography" *Analytical Chemistry, American Chemical Society*.Sep. 15, 1999. vol. 71, No. 18. pp. 4030-4033. 4 pages.

Jones et al. "Mycobacteria Isolated From Soil" *Canadian Journal of Microbiology, National Research Council of Canada*.Apr. 1965. vol. 11, No. 2. pp. 127-133. 9 pages.

Kabsch, Wolfrang. "Integration, scaling, space-group assignment and post-refinement" *Acta Crystallographica Section D—Biological Crystallography, International Union of Crystallography*.2010. vol. D66. pp. 133-144. 12 pages.

Kabsch, Wolfrang. "XDS" *Acta Crystallographica Section D—Biological Crystallography, International Union of Crystallography*. 2010. vol. D66. pp. 125-132. 9 pages.

Karasulu et al. "Photoinduced Intramolecular Charge Transfer in an Electronically Modified Flavin Derivative: Roseoflavin" *The Journal of Physical Chemistry, American Chemical Society*.2015. vol. 119. pp. 928-943. 17 pages.

Kelley et al. "The Phyre2 web portal for protein modeling, prediction and analysis" *Nature Protocols, Nature America Inc*.2015. vol. 10, No. 6. pp. 845-858. 14 pages.

Kemmer et al. "Nonlinear least-squares data fitting in Excel spreadsheets" *Nature Protocols, Nature Publishing Group*.2010. vol. 5, No. 2. pp. 267-281. 15 pages.

Kerbarh O., et al., "Mechanistic and Inhibition Studies of Chorismate-utilizing Enzymes," Biochemical Society Transactions, Aug. 2005, vol. 33 (Pt 4), 4 pages.

Kern et al. "Ch. 25—Measurement of Phenazines in Bacterial Cultures" *Methods in Molecular Biology—Pseudomonas Methods and Protocols, Springer Science+Business Media*.2014.pp. 303-310. 9 pages.

Kidani et al. "Studies on Metal Chelate Compounds of Phenazine Derivatives. I. Spectrophotometric Studies on Copper Chelate Compounds of I-Hydroxphenazine and its Di-N-oxide" *Chemical and Pharmaceutical Bulletin, Pharmaceutical Society of Japan*.1958. vol. 6, No. 5. pp. 556-562. 7 pages.

Kidani et al. "Studies on Metal Chelate Compounds of Phenazine Derivatives. VIII. Metal Complexes of I-Hydroxphenazine—Abstract Only" *Yakugaku Zasshi, Pharmaceutical Society of Japan*. 1973.vol. 93, No. 9. pp. 1089-1093. 5 pages.

Kim et al. "Protein structure prediction and analysis using the Robetta server" *Nucleic Acids Research, Oxford University Press*. 2004. vol. 32. pp. W5236-W531. 6 pages.

Kim et al. "Tolerance of dormant and active cells in Pseudomonas aeruginosa PA01 biofilm to antimicrobial agents" *Journal of Antimicrobial Chemotherapy, Oxford University Press*.2009. vol. 63. pp. 129-135. 7 pages.

Kobayashi K., et al., "Activation of SoxR-dependent Transcription in Pseudomonas Aeruginosa," Journal of Biochemistry, Nov. 2004, vol. 136 (5), 9 pages.

Konings A.F., et al., "Pseudomonas Aeruginosa Uses Multiple Pathways to Acquire Iron During Chronic Infection in Cystic Fibrosis Lungs," Infection and Immunity, Aug. 2013, vol. 81 (8), 8 pages.

Kopf et al. "Ligand-Enhanced Abiotic Iron Oxidation and the Effects of Chemical versus Biological Iron Cycling in Anoxic Environments" Environmental Science & Technology, American Chemical Society. 2013. vol. 47. pp. 2602-2611. 10 pages.

Kragh et al. "Role of Multicellular Aggregates in Biofilm Formation" *mBio, American Society for Microbiology*.2016. vol. 7, No. 3. pp. 1-11. 11 pages.

Kreamer et al. "The Ferrous Iron-Responsive BqsRS Two-Component System Activates Genes That Promote Cationic Stress Tolerance" *mBio, American Society of Microbiology*.Mar./Apr. 2015. vol. 6, No. 2. pp. 1-12. 12 pages.

Krogh et al. "Predicting Transmembrane Protein Topology with a Hidden Markov Model: Application to Complete Genomes" *Journal of Molecular Biology, Academic Press*.2001. vol. 305. pp. 567-580. 14 pages.

Lam K.S., et al., "A New Type of Synthetic Peptide Library for Identifying Ligand-binding Activity," Nature, Nov. 1991, vol. 354 (6348), 23 pages.

Lam K.S., et al., "Application of Combinatorial Library Methods in Cancer Research and Drug Discovery," Anti-cancer Drug Design, Apr. 1997, vol. 12 (3), 24 pages.

Laursen J.B., et al., "Phenazine Natural Products: Biosynthesis, Synthetic Analogues, and Biological Activity," Chemical Reviews, Mar. 2004, vol. 104 (3), 24 pages.

Li X.Z., et al., "Influence of the MexA-MexB-oprM Multidrug Efflux System on Expression of the MexC-MexD-oprJ and MexE-MexF-oprN Multidrug Efflux Systems in Pseudomonas Aeruginosa," The Journal of Antimicrobial Chemotherapy, Dec. 2000, vol. 46 (6), 9 pages.

Lim, Y.W., et al., "Metagenomics and Metatranscriptomics: Windows on CF-associated Viral and Microbial Communities," Journal of Cystic Fibrosis, Mar. 2013, vol. 12 (2), 11 pages.

Lin M.H., et al., "Involvement of Iron in Biofilm Formation by *Staphylococcus aureus*," PLoS One, Mar. 2012, vol. 7 (3), 7 pages. 7 pages.

Liochev S.I., et al., "Induction of the soxRS Regulon of *Escherichia coli* by Superoxide," The Journal of Biological Chemistry, Apr. 1999, vol. 274 (14), 4 pages.

Liu Y., et al., "Synergistic Activities of an Efflux Pump Inhibitor and Iron Chelators Against Pseudomonas Aeruginosa Growth and Biofilm Formation," Antimicrobial Agents and Chemotherapy, Sep. 2010, vol. 54 (9), 4 pages.

Lovley D.R., et al., "Humic Substances as Electron Acceptors for Microbial Respiration," Nature, Aug. 1996, vol. 382, 4 pages.

Mah et al. "A genetic basis for Pseudomonas aeruginosa biofilm antibiotic resistance" *Nature, Nature Publishing Group*.Nov. 20, 2003. vol. 426. pp. 306-310. 5 pages.

Malasarn et al. "Characterization of the Arsenate Respiratory Reductase from *Shewanella* sp. Strain ANA-3" *Journal of Bacteriology, American Society for Microbiology*.Jan. 2008. vol. 190, No. 1. pp. 135-142. 8 pages.

Mavrodi et al. "Irrigation Differentially Impacts Populations of Indigenous Antibiotic-Producing *Pseudomonas* spp. in the Rhizosphere of Wheat" *Applied and Environmental Microbiology, American Society of Microbiology*. May 2012. vol. 78, No. 9. pp. 3214-3220. 7 pages.

Mazzola M., et al., "Contribution of Phenazine Antibiotic Biosynthesis to the Ecological Competence of Fluorescent Pseudomonads in Soil Habitats," Applied and Environmental Microbiology, Aug. 1992, vol. 58 (8), 9 pages.

McCoy et al. "Phaser crystallographic software" *Journal of Applied Crystallography, International Union of Crystallography*.2007. vol. 40. pp. 658-674. 17 pages.

McIlwain et al. "359. The Phenazine Series. Part VI. Reactions of Alkyl Phenazonium Salts; the Phenazyls" *Journal of the Chemical Society, Royal Society of Chemistry*.1937.pp. 1704-1711. 9 pages.

Mehra S., et al., "A Framework to Analyze Multiple Time Series Data: A Case Study With Streptomyces Coelicolor," Journal of Industrial Microbiology and Biotechnology, Feb. 2006, vol. 33 (2), 14 pages.

Michaelis et al. "Potentiometric Studies on Semiquinones" *Journal of the American Chemical Society, American Chemical Society*. Apr. 1933. vol. 55. pp. 1481-1494. 14 pages.

(56) References Cited

OTHER PUBLICATIONS

Michaelis et al. "The Viologen Indicators" *The Journal of General Physiology, Rockefeller University Press*.1933. vol. 16, No. 6. pp. 859-873. 15 pages.

Michaelis L., et al., "Potentiometric Studies on Semiquinones," Journal of the American Chemical Society, Apr. 1933, vol. 55 (4), 14 pages.

Michaelis L., et al., "The Viologen Indicators," Journal of General Physiology, Jul. 1933, vol. 16 (6), 15 pages.

Moree et al. "Interkingdom metabolic transformations captured by microbial imaging mass spectrometry" *Proceedings of the National Academy of Sciences, National Academy of Sciences*.Aug. 21, 2012. vol. 109, No. 35. pp. 13811-13816. 6 pages.

Moriarty et al. "Electronic Ligand Builder and Optimization Workbench (eLBOW): a tool for ligand coordinate and restraint generation" *Acta Crystallographica Section D—Biological Crystallography, International Union of Crystallography*.2009. vol. D65. pp. 1074-1080. 7 pages.

Morrison et al. "Flavin Model Systems. I. The Electrochemistry of 1-Hydroxyphenazine and Pyocyanine in Aprotic Solvents" *Journal of the American Chemical Society, American Chemical Society*. 1978. vol. 100, No. 1. pp. 207-211. 5 pages.

Nancollas et al. "Guidelines for the Determination of Stability Constants" *Pure and Applied Chemistry, International Union of Pure and Applied Chemistry*.1982. vol. 54, No. 12. pp. 2675-2692. 18 pages.

Nash, T. "The Colorimetric Estimation of Formaldehyde by Means of the Hantzsch Reaction" *Biochemical Journal, Portland Press*. 1953. vol. 55. pp. 416-421. 6 pages.

Neubauer et al. "Lipid remodeling in Rhodopseudomonas palustris TIE-1 upon loss of hopanoids and hopanoid methylation" *Geobiology, John Wiley & Sons Ltd*.2015. vol. 13, No. 5. pp. 1-11. 11 pages.

Newman D.K., et al., "A Role for Excreted Quinones in Extracellular Electron Transfer," Nature, May 2000, vol. 405 (6782), 4 pages.

Non-Final Office Action for U.S. Appl. No. 12/548,362, dated Aug. 28, 2014, 9 pages.

Non-Final Office Action for U.S. Appl. No. 12/548,362, dated Mar. 27, 2012, 7 pages.

Non-Final Office Action for U.S. Appl. No. 13/456,172, dated Mar. 23, 2015, 25 pages.

Non-Final Office Action for U.S. Appl. No. 13/456,172, dated Nov. 18, 2013, 31 pages.

Non-Final Office Action for U.S. Appl. No. 15/394,138, filed Dec. 29, 2016 on behalf of California Institute of Technology, dated Apr. 2, 2019. 5 pages.

Non-Final Office Action for U.S. Appl. No. 15/466,839, filed Mar. 22, 2017, on behalf of California Institute of Technology, dated Dec. 11, 2018. 34 pages.

Norman et al. "Effect of Pyocyanin on a Crude-Oil-Degrading Microbial Community" *Applied and Environmental Microbiology, American Society for Microbiology*.Jul. 2004. vol. 70, No. 7. pp. 4004-4011. 8 pages.

Nosanchuk J., et al., "The Contribution of Melanin to Microbial Pathogenesis," Cellular Microbiology, Apr. 2003, vol. 5 (4), 21 pages.

O'Toole, George A. "To Build a Biofilm" *Journal of Bacteriology, American Society for Microbiology*.May 2003. vol. 185, No. 9. pp. 2687-2689. 3 pages.

Padilla et al. "A statistic for local intensity differences: robustness to anisotropy and pseudo-centering and utility for detecting twinning" *Acta Crystallographica Section D—Biological Crystallography, International Union of Crystallography*.2003. vol. D59. pp. 1124-1130. 7 pages.

Park W., et al., "Regulation of Superoxide Stress in Pseudomonas Putida KT2440 Is Different From the SoxR Paradigm in *Escherichia coli*," Biochemical and Biophysical Research Communications, Mar. 2006, vol. 341(1), 6 pages.

Parsons et al. "Structural and Functional Analysis of the Pyocyanin Biosynthetic Protein PhzM from Pseudomonas aeruginosa" *Biochemistry, American Chemical Society*. Feb. 20, 2007. vol. 46, No. 7. pp. 1821-1828. 20 pages.

Pearson et al. "Improved Tools for Biological Sequence Comparison" *Proceedings of the National Academy of Sciences, National Academy of Sciences*.Apr. 15, 1988. vol. 85, No. 8. pp. 2444-2448. 6 pages.

Pearson, William R. "Searching Protein Sequence Libraries: Comparison to the Sensitivity and Selectivity of the Smith-Waterman and FASTA Algorithms" *Genomics, Academic Press Inc*.1991. vol. 11. pp. 635-650. 16 pages.

Pezzulo et al. "Reduced Airway Surface pH Impairs Bacterial Killing in the Porcine Cystic Fibrosis Lung" *Nature, Nature Publishing Group*.2012. vol. 487, No. 7405. pp. 109-113. 20 pages.

Pomposiello P.J., et al., "Identification of SoxS-Regulated Genes in *Salmonella enterica* Serovar Typhimurium," Journal of Bacteriology, Jan. 2000, vol. 182 (1), 7 pages.

Price-Whelan et al. "Corrigendum: Rethinking "secondary" metabolism: physiological roles for phenazine antibiotics" *Nature Chemical Biology, Nature Publishing Group*.Apr. 2006. vol. 2, No. 4. pp. 221. 2 page.

Raman et al. "Structure prediction for CASP8 with all-atom refinement using Rosetta" *Proteins, Wiley-Liss Inc*.2009. vol. 77. pp. 89-99. 11 pages.

Recinos D.A., et al., "Redundant Phenazine Operons in Pseudomonas Aeruginosa Exhibit Environment-Dependent Expression and Differential Roles in Pathogenicity," Proceedings of the National Academy of Sciences of the United States of America, Nov. 20, 2012, vol. 109(47), 21 pages.

Reid D.W., et al., "Iron Chelation Directed against Biofilms as an Adjunct to Conventional Antibiotics," American Journal of Physiology-Lung Cellular and Molecular Physiology, Apr. 28, 2009, vol. 296(5), 2 pages.

Response to Restriction Requirement for U.S. Appl. No. 12/548,362, dated Nov. 29, 2011, 6 pages.

Restriction Requirement for U.S. Appl. No. 13/456,172, dated Feb. 12, 2013, 10 pages.

Restriction Requirement for U.S. Appl. No. 15/394,138, filed Dec. 29, 2016, on behalf of the California Institute of Technology, dated Oct. 1, 2018. 5 pgs.

Restriction Requirement for U.S. Appl. No. 15/420,022, filed Jan. 30, 2017, on behalf of California Institute of Technology, dated Mar. 13, 2019. 8 pages.

Restriction Requirement for U.S. Appl. No. 15/466,839, filed Mar. 22, 2017, on behalf of California Institute of Technology, dated May 1, 2018. 10 pages.

Rocha E.R., et al., "Effect of Ferric and Ferrous Iron Chelators on Growth of Bacteroides Fragilis under Anaerobic Conditions," FEMS Microbiology Letters, Nov. 1, 1991, vol. 68(1), 6 pages.

Rozen S., et al., "Primer3 on the WWW for General Users and for Biologist Programmers," Methods in Molecular Biology, 2000, vol. 132, 22 pages.

Ruiz et al. "Relationship between Clinical and Environmental Isolates of Pseudomonas aeruginosa in a Hospital Setting" *Archives of Medical Research*, Elsevier. 2004. vol. 35. pp. 251-257. 7 pages.

Scott J.K., et al., "Searching for Peptide Ligands with an Epitope Library," Science, Jul. 27, 1990, vol. 249(4967), 5 pages.

Shih et al. "Self-cleavage of fusion protein in vivo using TEV protease to yield native protein" *Protein Science, Cold Spring Harbor Laboratory Press*.2005. vol. 14. pp. 936-941. 6 pages.

Shyu et al. "Protective Role of tolC in Efflux of the Electron Shuttle Anthraquinone-2, 6-Disulfonate" *Journal of Bacteriology, American Society for Microbiology*.Mar. 2002. vol. 184, No. 6. pp. 1806-1810. 5 pages.

Smith et al. "Identification of Common Molecular Subsequences" *Journal of Molecular Biology, Academic Press Inc*.1981.vol. 147. pp. 195-197. 4 pages.

Song et al. "High-Resolution Comparative Modeling with RosettaCM" *Structure, Cell Press*.Oct. 8, 2013. vol. 21. pp. 1735-1742. 8 pages.

Stewart, Philip S. "Biofilm Accumulation Model That Predicts Antibiotic Resistance of Pseudomonas aeruginosa Biofilms" *Anti-*

(56) References Cited

OTHER PUBLICATIONS

*microbial Agents and Chemotherapy, American Society for Microbiology*.May 1994. vol. 38, No. 5. pp. 1052-1058. 7 pages.
Studier et al. "Use of Bacteriophage T7 RNA Polymerase to Direct Selective High-level Expression of Cloned Genes" *Journal of Molecular Biology, Academic Press Inc.*1986. vol. 189. pp. 113-130. 18 pages.
Summers et al. "Novel, Highly Specific N-Demethylases Enable Bacteria to Live on Caffeine and Related Purine Alkaloids" *Journal of Bacteriology, American Society for Microbiology*.Apr. 2012. vol. 194, No. 8. pp. 2041-2049. 9 pages.
Sundberg S.A., et al., "High-throughput and Ultra-high-throughput Screening: Solution-and Cell-based Approaches," Current Opinion in Biotechnology, Feb. 2000, vol. 11 (1), 7 pages.
Taga et al. "BluB cannibalizes flavin to form the lower ligand of vitamin B12" *Nature, Nature Publishing Group*.Mar. 22, 2007. vol. 446, No. 7134. pp. 449-453. 11 pages.
Tahlan K., et al., "Initiation of Actinorhodin Export in Streptomyces Coelicolor," Molecular Microbiology, Feb. 2007, vol. 63 (4), 11 pages.
Tamura et al. "MEGA6: Molecular Evolutionary Genetics Analysis Version 6.0" *Molecular Biology and Evolution, Oxford University Press*.2013. vol. 30, No. 12. pp. 2725-2729. 5 pages.
Teal et al. "Spatiometabolic Stratification of Shewanella oneidensis Biofilms" *Applied and Environmental Microbiology, American Society for Microbiology*.Nov. 2006. vol. 72, No. 11. pp. 7324-7330. 7 pages.
Terwilliger et al. "Automated ligand fitting by core-fragment fitting and extension into density" *Acta Crystallographica Section D—Biological Crystallography, International Union of Crystallography*. 2006. vol. D62. pp. 915-922. 8 pages.
Terwilliger et al. "Iterative model building, structure refinement and density modification with the PHENIX AutoBuild wizard" *Acta Crystallographica Section D—Biological Crystallography, International Union of Crystallography*.2008.vol. D64. pp. 61-69. 9 pages.
Terwilliger et al. "Ligand identification using electron-density map correlations" *Acta Crystallographica Section D—Biological Crystallography, International Union of Crystallography*, Jan. 2007. vol. 63—Part 1. pp. 101-107. 7 pages.
Timms-Wilson et al. "Chromosomal Insertion of Phenazine-1-Carboxylic Acid Biosynthetic Pathway Enhances Efficacy of Damping-off Disease Control by Pseudomonas fluorescens" *Molecular Plant-Microbe Interactions, The American Phytopathological Society*. 2000. vol. 13, No. 12. pp. 1293-1300. 8 pages.
Tipton et al. "QapR (PA5506) Represses on Operon That Negatively Affects the Pseudomonas Quinolone Signal in Pseudomonas aeruginosa" *Journal of Bacteriology, American Society for Microbiology*.Aug. 2013. vol. 195, No. 15. pp. 3433-3441. 9 pages.
To T.B., et al., "New Method for the Direct Determination of Dissolved Fe(III) Concentration in Acid Mine Waters," Environmental Science & Technology, 1999, vol. 33 (5), 7 pages.
Tsaneva I.R., et al., "soxR, a Locus Governing a Superoxide Response Regulon in *Escherichia coli* K-12," Journal of Bacteriology, Aug. 1990, vol. 172 (8), 9 pages.
Turick C.E., et al., "Melanin Production and Use as a Soluble Electron Shuttle for Fe(III) Oxide Reduction and as a Terminal Electron Acceptor by Shewanella algae BrY," Applied and Environmental Microbiology, May 2002, vol. 68 (5), 9 pages.
Turner et al. "Occurrence, Biochemistry and Physiology of Phenazine Pigment Production" *Advances in Microbial Physiology, Academic Press*.1986. vol. 27. pp. 211-275. 65 pages.
Vanitha et al. "Bio Control Potential of Pseudomonas fluorescens against Coleus Root Rot Disease" *Journal of Plant Pathology and Microbiology, OMICS International*.2014. vol. 5, No. 1. 4 pages.
Wallace Jr et al. "Spectrum of Disease Due to Rapidly Growing Mycobacteria" *Reviews of Infectious Diseases, University of Chicago*. Jul./Aug. 1983. vol. 5, No. 4. pp. 657-679. 24 pages.
Walsh et al. "Flavoenzymes: Versatile Catalysts in Biosynthetic Pathways" *Natural Product Reports, Royal Society of Chemistry*. Jan. 2013. vol. 30, No. 1. pp. 1-53. 53 pages.
Whitchurch et al. "Extracellular DNA Required for Bacterial Biofilm Formation" *Science, American Association for the Advancement of Science*. Feb. 22, 2002. vol. 295. pp. 1487. 2 pages.
Williams R.P., et al., "Symposium on Bacterial Pigments," Bacteriological Reviews, Dec. 1956, vol. 20 (4), 3 pages.
Winn et al. "Overview of the CCP4 suite and current developments" *Acta Crystallogrpahica Section D—Biological Crystallography, International Union of Crystallography*.2011. vol. D67. pp. 235-242. 8 pages.
Winn et al. "Use of TLS parameters to model anisotropic displacements in macromolecular refinement" *Acta Crystallographica Section D—Biological Crystallography, International Union of Crystallography*.2001. vol. D57. pp. 122-133. 12 pages.
Wiren V.N., et al., "Nicotianamine Chelates both FeIII and FeII. Implications for Metal Transport in Plants," Plant Physiology, Mar. 1999, vol. 119 (3), 8 pages.
Written Opinion for International Application No. PCT/US2017/023688, filed on Mar. 22, 2017, on behalf of California Institute of Technology, dated Jun. 30, 2017. 14 pages.
Wu et al. "Quantitative hopanoid analysis enables robust pattern detection and comparison between laboratories" *Geobiology, John Wiley & Sons Ltd*.2015. vol. 13, No. 4. pp. 391-407. 17 pages.
Yim G., et al., "Antibiotics as Signalling Molecules," Philosophical Transactions of the Royal Society of London, Jul. 2007, vol. 362 (1483), 6 pages.
Zuckermann R.N., et al., "Discovery of Nanomolar Ligands for 7-transmembrane G-protein-coupled Receptors From a Diverse N-(Substituted)glycine Peptoid Library," Journal of Medicinal Chemistry, Aug. 1994, vol. 37 (17), 8 pages.

\* cited by examiner

| REPORT # | PRODUCT/TEST | METHOD | RESULT | UNITS | START DT |
|---|---|---|---|---|---|
| M317164-01 | VIRGIN SHEATH FLUID (PHOSPHATE BUFFERED SALINE) | | | | |
| | STANDARD PLATE COUNT SPC | FDA(BAM)CH.3 | 74,000 | /gm | 5/9/2014 |
| | YEAST | FDA(BAM)CH.18 | < 10 | /gm | 5/9/2014 |
| | MOLD | FDA(BAM)CH.18 | < 10 | /gm | 5/9/2014 |
| | BACTERIAL IDENTIFICATION | VITEK | PSEUDOMONAS STUTZERI | | 5/9/2014 |
| M317164-02 | VIRGIN MEDIA (EXPECTED TO BE STERILE) | | | | |
| | STANDARD PLATE COUNT SPC | FDA(BAM)CH.3 | < 10 | /gm | 5/9/2014 |
| | YEAST | FDA(BAM)CH.18 | < 10 | /gm | 5/9/2014 |
| | MOLD | FDA(BAM)CH.18 | < 10 | /gm | 5/9/2014 |
| M317164-03 | FLOW THROUGH (MICROBIOLOGICALLY CONTAMINATED SHEATH PLUS MEDIA) | | | | |
| | STANDARD PLATE COUNT SPC | FDA(BAM)CH.3 | 890,000,000 | /gm | 5/9/2014 |
| | YEAST | FDA(BAM)CH.18 | < 10 | /gm | 5/9/2014 |
| | MOLD | FDA(BAM)CH.18 | < 10 | /gm | 5/9/2014 |
| | BACTERIAL IDENTIFICATION | VITEK | SEE REMARK BELOW | | 5/9/2014 |

*The isolate from M317164-03 is identified as Ochrobactrum anthropi.

FIG. 14

| REPORT # | PRODUCT / TEST | METHOD | RESULT | UNITS | START DT |
|---|---|---|---|---|---|
| M318915-01 | PURPLE CONTROL MEDIA 5/13 (EXPECTED TO BE STERILE) | | | | |
| | STANDARD PLATE COUNT SPC | FDA(BAM)CH.3 | 10 | /gm | 5/23/2014 |
| | YEAST | FDA(BAM)CH.18 | < 10 | /gm | 5/23/2014 |
| | MOLD | FDA(BAM)CH.18 | < 10 | /gm | 5/23/2014 |
| M318915-02 | PURPLE 20X PBS NEW (EXPECTED TO BE STERILE) | | | | |
| | STANDARD PLATE COUNT SPC | FDA(BAM)CH.3 | < 10 | /gm | 5/23/2014 |
| | YEAST | FDA(BAM)CH.18 | < 10 | /gm | 5/23/2014 |
| | MOLD | FDA(BAM)CH.18 | < 10 | /gm | 5/23/2014 |
| M318915-03 | PURPLE TEST 5/13 (MICROBIOLOGICALLY CONTAMINATED SHEATH PLUS MEDIA) | | | | |
| | STANDARD PLATE COUNT SPC | FDA(BAM)CH.3 | 110,000,000 | /gm | 5/23/2014 |
| | YEAST | FDA(BAM)CH.18 | < 10 | /gm | 5/23/2014 |
| | MOLD | FDA(BAM)CH.18 | < 10 | /gm | 5/23/2014 |
| | BACTERIAL IDENTIFICATION | VITEK | SEE REMARK BELOW | | 5/23/2014 |
| M318915-04 | D.I. H2O 5/15 KB | | | | |
| | STANDARD PLATE COUNT SPC | FDA(BAM)CH.3 | < 10 | /gm | 5/23/2014 |
| | YEAST | FDA(BAM)CH.18 | < 10 | /gm | 5/23/2014 |
| | MOLD | FDA(BAM)CH.18 | < 10 | /gm | 5/23/2014 |
| M318915-05 | D.I. H2O NO HOSE 5/21 KB | | | | |
| | STANDARD PLATE COUNT SPC | FDA(BAM)CH.3 | < 10 | /gm | 5/23/2014 |
| | YEAST | FDA(BAM)CH.18 | < 10 | /gm | 5/23/2014 |
| | MOLD | FDA(BAM)CH.18 | < 10 | /gm | 5/23/2014 |
| M318915-06 | MILLI Q H2O 5/15 KB (EXPECTED TO BE STERILE) | | | | |
| | STANDARD PLATE COUNT SPC | FDA(BAM)CH.3 | 67,000 | /gm | 5/23/2014 |
| | YEAST | FDA(BAM)CH.18 | < 10 | /gm | 5/23/2014 |
| | MOLD | FDA(BAM)CH.18 | < 10 | /gm | 5/23/2014 |
| | BACTERIAL IDENTIFICATION | VITEK | SEE REMARK BELOW | | 5/23/2014 |
| M318915-07 | SHEATH TANK ARIA 5/15 KB | | | | |

Fig. 15

| REPORT # | PRODUCT / TEST | METHOD | RESULT | UNITS | STARTDT |
|---|---|---|---|---|---|
| | STANDARD PLATE COUNT SPC | FDA(BAM)CH.3 | 30 | /gm | 5/23/2014 |
| | YEAST | FDA(BAM)CH.18 | < 10 | /gm | 5/23/2014 |
| | MOLD | FDA(BAM)CH.18 | < 10 | /gm | 5/23/2014 |
| M318915-08 | SHEATH FLOW THRU ARIA 5/19 KB | | | | |
| | STANDARD PLATE COUNT SPC | FDA(BAM)CH.3 | 56,000 | /gm | 5/23/2014 |
| | YEAST | FDA(BAM)CH.18 | < 10 | /gm | 5/23/2014 |
| | MOLD | FDA(BAM)CH.18 | < 10 | /gm | 5/23/2014 |
| M318915-09 | SHEATH FLOW FILTER 5/19 KB | | | | |
| | STANDARD PLATE COUNT SPC | FDA(BAM)CH.3 | < 10 | /gm | 5/23/2014 |
| | YEAST | FDA(BAM)CH.18 | < 10 | /gm | 5/23/2014 |
| | MOLD | FDA(BAM)CH.18 | < 10 | /gm | 5/23/2014 |
| M318915-10 | SHEATH (BUCKET) OVER WEEKEND 5/19 KB | | | | |
| | STANDARD PLATE COUNT SPC | FDA(BAM)CH.3 | 56,000 | /gm | 5/23/2014 |
| | YEAST | FDA(BAM)CH.18 | < 10 | /gm | 5/23/2014 |
| | MOLD | FDA(BAM)CH.18 | < 10 | /gm | 5/23/2014 |
| M318915-11 | SHEATH TANK SONY 5/19 KB | | | | |
| | STANDARD PLATE COUNT SPC | FDA(BAM)CH.3 | 92,000 | /gm | 5/23/2014 |
| | YEAST | FDA(BAM)CH.18 | < 10 | /gm | 5/23/2014 |
| | MOLD | FDA(BAM)CH.18 | < 10 | /gm | 5/23/2014 |
| M318915-12 | FLOW THROUGH SONY 5/19 KB | | | | |
| | STANDARD PLATE COUNT SPC | FDA(BAM)CH.3 | 10 | /gm | 5/23/2014 |
| | YEAST | FDA(BAM)CH.18 | < 10 | /gm | 5/23/2014 |
| | MOLD | FDA(BAM)CH.18 | < 10 | /gm | 5/23/2014 |
| M318915-13 | SHEATH FLOW THROUGH ARIA 5/19 | | | | |
| | STANDARD PLATE COUNT SPC | FDA(BAM)CH.3 | 380,000 | /gm | 5/23/2014 |
| | YEAST | FDA(BAM)CH.18 | < 10 | /gm | 5/23/2014 |
| | MOLD | FDA(BAM)CH.18 | < 10 | /gm | 5/23/2014 |
| | BACTERIAL IDENTIFICATION | VITEK | SEE REMARK BELOW | | 5/23/2014 |

*Isolates from above samples were picked for bacterial identification. The isolates were identified as: M318915-03: Ochrobactrum anthropi, M318915-06: Pseudomonas monteilii/stutzeri, M318915-13: Ochrobactrum anthropi, Pseudomonas monteilii/stutzeri.

FIG. 16

SEQUENCE LISTING

<160> NUMBER OF SEQ ID NOS: 24

<210> SEQ ID NO 1
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 1
cctgtgcaat gacatcatcc                                                  20

<210> SEQ ID NO 2
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 2
ttcttgtcac gctggttgag                                                  20

<210> SEQ ID NO 3
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 3
agcagccact ccaaagaaac                                                  20

<210> SEQ ID NO 4

```
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 4
cagagcttcg tcagccttg                                                   19

<210> SEQ ID NO 5
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 5
gagctggaaa aggacacctg                                                  20

<210> SEQ ID NO 6
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 6
tttccaggat cggcgtatag                                                  20

<210> SEQ ID NO 7
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 7
agccctacga cctgatcatt                                                  20

<210> SEQ ID NO 8
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 8
cggcttggtc agatagtcgt                                                  20

<210> SEQ ID NO 9
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 9
cacagccagt acctggaaca                                                  20

<210> SEQ ID NO 10
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 10
```
gggtagctgt cgttgaggtc                                                20

<210> SEQ ID NO 11
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 11
ggaccgcgac tacttctacg                                                20

<210> SEQ ID NO 12
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 12
tcgagtcgat gtgctggtat                                                20

<210> SEQ ID NO 13
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 13
aaccgtcccg ttcctacc                                                  18

<210> SEQ ID NO 14
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 14
cagaagcccc atggagaa                                                  18

<210> SEQ ID NO 15
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 15
gagcggctga ttaccatcat                                                20

<210> SEQ ID NO 16
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 16
cgagcaggta cagggagaag                                                20

<210> SEQ ID NO 17
<211> LENGTH: 20
<212> TYPE: DNA

<213> ORGANISM: Artificial Sequence
<220> FEATURE:
<223> OTHER INFORMATION: Synthetic polynucleotide

<400> SEQUENCE: 17
aaggtggtct acggcctgat                                          20

<210> SEQ ID NO 18
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 18
actggtcgaa ggtggagttg                                          20

<210> SEQ ID NO 19
<211> LENGTH: 43
<212> TYPE: DNA
<213> ORGANISM: Artificial Sequence
<220> FEATURE:
<223> OTHER INFORMATION: Synthetic polynucleotide

<400> SEQUENCE: 19
taatacgact cactataggg agatgctgta ttgctccttc tgc                 43

<210> SEQ ID NO 20
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 20
cgggaaatct tgtcgatctc                                          20

<210> SEQ ID NO 21
<211> LENGTH: 42
<212> TYPE: DNA
<213> ORGANISM: Artificial Sequence
<220> FEATURE:
<223> OTHER INFORMATION: Synthetic polynucleotide

<400> SEQUENCE: 21
taatacgact cactataggg agaatgcaac tggacgagca ac                  42

<210> SEQ ID NO 22
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 22
gaacgcttca gggtctcctc                                          20

<210> SEQ ID NO 23
<211> LENGTH: 43
<212> TYPE: DNA
<213> ORGANISM: Artificial Sequence
<220> FEATURE:
<223> OTHER INFORMATION: Synthetic polynucleotide

<400> SEQUENCE: 23
taatacgact cactataggg agagctggtt gaggatcacg ttc                 43

```
<210> SEQ ID NO 24
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 24
gacctcgatg acgttggaat                                              20
```

METHODS AND SYSTEM FOR INTERFERING WITH VIABILITY OF BACTERIA AND RELATED COMPOUNDS AND COMPOSITIONS

CROSS REFERENCE TO RELATED APPLICATIONS

The present application claims priority to U.S. Provisional Application No. 62/039,385 filed on Aug. 19, 2014 and entitled "Methods and Systems for Interfering with Viability of Bacteria and Related Compounds and Compositions", the disclosure of which is incorporated herein by reference in its entirety. The present application is also a continuation in part and claims priority to U.S. application Ser. No. 13/456,172 filed on Apr. 25, 2012 and entitled Methods and systems for interfering with viability of Bacteria and Related Compounds and compositions" which on its turn claims priority to U.S. Provisional Application No. 61/478,746 filed on Apr. 25, 2011 and entitled "Methods and systems for interfering with viability of Bacteria and Related Compounds and compositions", the disclosure of each of which is incorporated herein by reference in its entirety.

FIELD

The present disclosure relates to methods and systems for interfering with viability of bacteria and related compounds and compositions.

BACKGROUND

Bacteria viability has been the focus of research in the field of biological analysis, in particular when aimed at medical applications such as therapeutic or diagnostic application.

Whether for pathological examination or for fundamental biology studies, several methods are commonly used for the detection and interference with the viability of bacteria.

Although various methods, systems and compositions have been developed to interfere, and in particular, reduce bacterial viability to the extent of killing the bacteria, antibiotic resistance and additional defense mechanisms of the microorganism have made development of methods, systems and compositions able to interfere and in particular inhibit bacterial viability particularly challenging.

SUMMARY

Provided herein, are methods and systems and related compounds and compositions that in several embodiments are suitable for reducing antibiotic resistance and/or survivability of bacteria. In several embodiments, compositions, methods and systems herein described are expected to be suitable to treat and/or prevent bacterial infection in vitro or in vivo. In several embodiments compositions, methods and systems herein described are expected to be suitable to treat and/or prevent bacterial contamination of surfaces such as hospital and laboratories equipment.

According to a first aspect, a method and system to interfere with viability of bacteria in a medium is described, the method comprising contacting the medium with an Fe(II) chelator and an Fe(III) chelator to reduce survivability and/or antibiotic resistance of bacteria in the medium. The system comprises one or more Fe(II) and Fe(III) chelators optionally in combination with an antibiotic and/or other antimicrobial. In some embodiments of the methods and systems, the medium can be a liquid or gel in vitro or a tissue or biological environment in vivo or ex vivo. In some embodiments of the methods and systems, the bacteria comprise persister cells.

According to a second aspect, a method and system for treating and/or preventing a bacterial infection in an individual is described. The method comprises administering to the individual an effective amount of one or more Fe(II) chelators and Fe(III) chelators. In particular, in some embodiments, administering of one or more Fe(II) chelators and Fe(III) chelators can be performed in combination with one or more antibiotics and/or other antimicrobials. The system comprises one or more Fe(II) chelators and Fe(III) chelators and an antibiotic and/or other antimicrobial. In some embodiments of methods and systems, the bacteria comprise persister cells.

According to a third aspect, an antimicrobial is described. The antimicrobial comprises one or more Fe(II) chelators and Fe(III) chelators. The one or more Fe(II) chelators and Fe(III) chelators are in particular comprised in the antimicrobial in an amount suitable to reduce antibiotic resistance and/or survivability of bacteria. In some embodiments, the antimicrobial comprises a compatible vehicle, which can be a vehicle for effective administrating and/or delivering of the one or more agents to an individual. In some embodiments of the methods and systems, the bacteria comprise persister cells.

According to a fourth aspect, a method and system to interfere with the viability of bacteria in a medium is described, the method comprises subtracting from the medium Fe(II) in combination with Fe(III) to reduce survivability and/or antibiotic resistance of the bacteria by administering Fe(II) chelators and Fe(III) chelators. The system comprises one or more Fe(II) chelators and Fe(III) chelators (for simultaneous combined or sequential use in the method herein described).

According to a fifth aspect, a method and system to minimize contamination from a bacterium from a surface is described. The method comprises contacting the surface with an Fe(II) chelator and an Fe(III) chelator optionally in combination with an antibiotic and/or other antimicrobial. The system comprises one or more Fe(II) chelators and one or more Fe(III) chelators and optionally an antibiotic and/or other antimicrobial. In some embodiments of the methods and systems, the bacteria comprise persister cells.

The methods and systems herein described, and related compounds and compositions in several embodiments allow reducing antibiotic resistance and/or bacterial survivability according to distinct mechanism and pathways wherein phenazine functions.

The methods and systems and related compounds and compositions herein described can be used in connection with applications wherein reduction of viability of bacteria and/or reduction of antibiotic resistance is desired, which include but are not limited to medical application, drug research, biological analysis and diagnostics including but not limited to clinical applications.

The details of one or more embodiments of the disclosure are set forth in the accompanying drawings and the description below. Other features, objects, and advantages will be apparent from the description and drawings, and from the claims.

BRIEF DESCRIPTION OF THE DRAWINGS

The accompanying drawings, which are incorporated into and constitute a part of this specification, illustrate one or more embodiments of the present disclosure and, together with the detailed description and examples sections, serve to explain the principles and implementations of the disclosure.

FIG. 1A shows a non-denaturing agarose gel with mRNA extracts from sputum samples (lanes 1-5), and a heat-degraded (95° C. for 20 min) bacterial mRNA control (lane 6). FIG. 1B shows a representative Agilent 2100 Bioanalyzer electropherogram of a sputum mRNA extract. FIG. 1C shows a diagram illustrating qRT-PCR detection of clpX relative to oprI in CF sputum. Each data point represents the average of triplicate measurements on a single sputum sample. FIG. 1D shows a table summarizing the results in vitro synthesized mRNA recovery from sputum and Trizol. Values represent the ratio of mRNA for each target gene (bqsR, bqsS) relative to clpX.

FIG. 3A shows a table summarizing the results of experiments directed to investigate sputum iron chemistry versus disease severity. Reported values are mean concentrations+/−one standard deviation, and are conservative estimates based on FerroZine® and ICP-MS measurements [1]. FIG. 3B shows a diagram illustrating percentage biomass versus untreated relative to administration of conalbumin, FerroZine® or both. Biofilm growth prevention (white) and dissolution (black) by conalbumin (an Fe(III)-chelator) and FerroZine® (an Fe(II)-chelator) are reported. Effects are mitigated by addition of 80 μM Fe(II). Symbols represent significance versus (*) untreated controls and (•) combination chelator treatment. Error bars represent the standard error of the mean (n=18).

FIG. 4A shows a diagram illustrating a determination of total sputum iron using ICP-MS versus FerroZine® measurements. Dashed line represents the linear regression trendline between the two measurements ($R^2$=0.73). FIG. 4B shows a diagram wherein concentration of Fe(II) and Fe(II) was determined on samples different time periods.

FIG. 5A shows total iron [Fe(III)+Fe(II)] concentration in function of forced expiratory volume, FEV1%, FIG. 5B shows Fe(II) concentration in function of forced expiratory volume, FEV1%, and FIG. 5C shows Fe(II) % in function of forced expiratory volume, FEV1%. Each point represents the average of duplicate measurements of a single sputum sample.

FIG. 6A shows a diagram showing total iron [Fe(III)+Fe(II)] concentration measured in cystic fibrosis (CF) patients in function of forced expiratory volume, FEV1%, FIG. 6B shows a diagram showing Fe(II) concentration in cystic fibrosis (CF) patients in function of forced expiratory volume, FEV1%, FIG. 6C shows a diagram showing Fe(III) concentration in cystic fibrosis (CF) patients in function of forced expiratory volume, FEV1% and FIG. 6D) shows a diagram showing Fe(II) percentage in cystic fibrosis (CF) patients in function of forced expiratory volume, FEV1%. Each point represents the average of measurements on multiple sputum samples from a single CF patient. As shown in FIG. 6A, FIG. 6B and FIG. 6D total iron and Fe(II) concentrations and Fe (II) % all increase as pulmonary function (FEV1%) declines. There is no significant increase in Fe(III) as shown in FIG. 6C.

FIG. 7A shows the detected Fe(II) percentage in function of the total phenazines (PYO+PCA) concentrations. FIG. 7B shows the detected Fe(II) percentage in function of phenazine-1-carboxylic acid (PCA) concentrations FIG. 7C shows the detected Fe(II) percentage in function of pyocyanin (PYO) concentrations Fe(II) dominates the iron pool at high concentrations of (FIG. 7A) total phenazines (PYO+PCA), (FIG. 7B) phenazine-1-carboxylic acid (PCA) but not (FIG. 7C) pyocyanin (PYO). These data likely reflect the higher reactivity of PCA with Fe(III) under anoxic conditions [2].

FIG. 8A shows expression levels of bqsS and bqsR in planktonic cultures of P. aeruginosa in response to 50 Fe(II) (black) relative to 50 μM Fe(III) (white) or no treatment (light grey) or in CF sputum samples (dark grey). For data related to planktonic cultures points represent average Ct values from three independent experiments; bars represent the standard deviation. For data related to sputum samples, points represent relative gene expression calculated from Ct values from triplicate measurements of an individual sputum sample. Transcriptional activity is shown relative to the endogenous housekeeping gene, oprI. FIG. 8B shows expression levels of feoA and feoB fptA, pvdA, and hasAp shown compared to laboratory cultures treated with Fe(II), Fe(III), and no iron as described for FIG. 8A.

FIG. 12A and FIG. 12B show biofilm growth prevention under (FIG. 12A) aerobic (~98% Fe(III)) and (FIG. 12B) anaerobic conditions (~10 µM Fe(II) and 10 µM Fe(III)) by conalbumin (an Fe(III)-chelator) and FerroZine® (an Fe(II) chelator). FIG. 11C and FIG. 11D show biofilm dissolution under (FIG. 12C) aerobic and (FIG. 12D) anaerobic conditions by conalbumin and FerroZine®. In all cases, chelator effects are mitigated by the addition of Fe in excess of the chelation capacity (80 µM Fe(III) under oxic conditions; Fe(II) under anoxia). Symbols represent significant versus untreated controls. Error bars represent standard error of the mean (n=12)

FIG. 14, FIG. 15 and FIG. 16 show tables illustrating the plate counts and identification of contaminants of the instrumentation of Caltech Flow Cytometry Cell Sorting Facility reported by Michelson laboratories.

DETAILED DESCRIPTION

Figure 1:
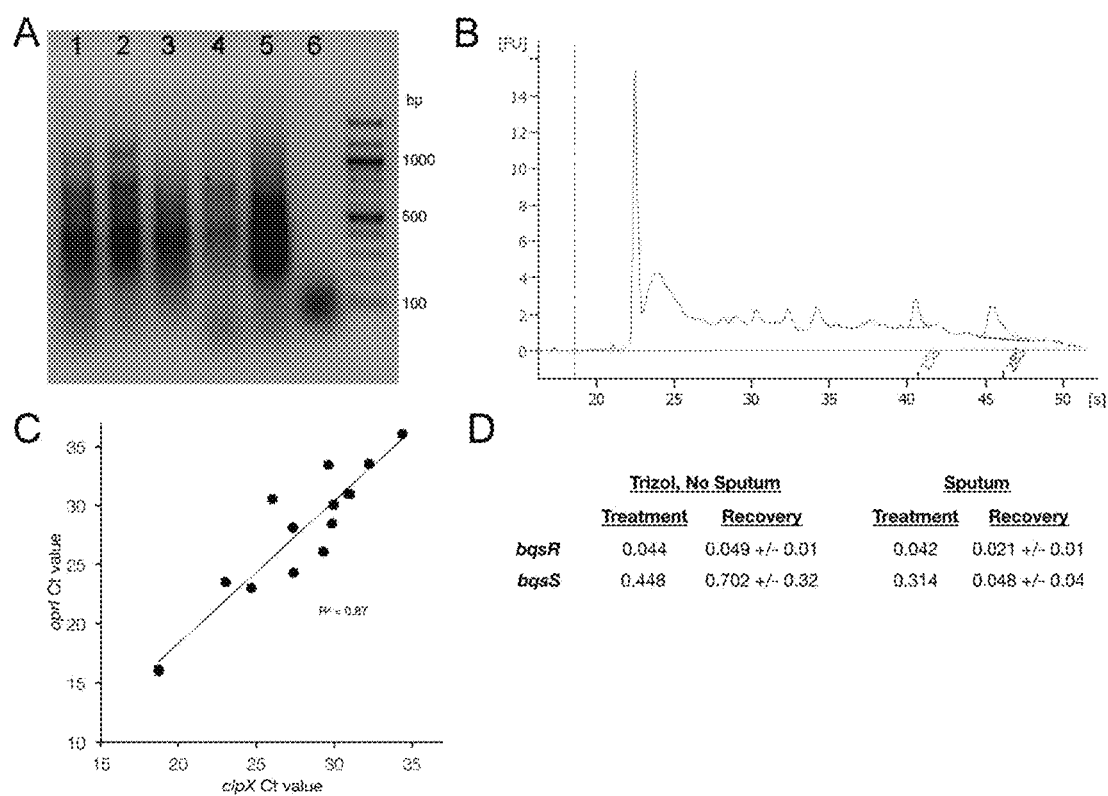
FIG. 1 shows an electrophoresis gel, diagrams and a table illustrating the results of experiments directed to validation of mRNA extraction and analysis.

Provided herein are methods and systems to directed to interfere with viability of bacteria in a medium.

The term "viability" as used here in refers to whether or not a bacterial cell is able to maintain itself or recover its potentiality. Viable cells in the sense of the present disclosure are cells able to, or capable of recover the ability to, form colonies and biofilms on or in a solid or liquid medium. Methods for evaluating the viability of bacteria after the use of the methods and systems for interference with viability of bacteria described herein include, but are not limited to measurement of colony forming units, cell counts such as that described by Wang et al. (J. Bacteriol. 2010, 192, 365-369) [3], and other methods identifiable to a skilled person upon the reading of the present disclosure.

The term "bacteria" as used herein refers to several prokaryotic microbial species which include but are not limited to Gram-negative and positive bacteria, such as, but not limited to, *Pseudomonas, Brevibacterium, Coryneform Bacteria, Nocardia Brevibacterium linens, Brevibacterium, Burkholderia cenocepecia, Methanosarcina mazei, Mycobacterium abscessus, Pantoea agglomerans, Pectobacterium atrosepticum, Pelagio variabilis, Pseudomonas fluorescens, Streptomyces anulatus, Streptomyces cinnamonensis, Ochrobactrum* to facilitate various physiological functions identifiable to a skilled person upon reading of the present disclosure. More specifically, the wording "Gram-negative bacteria" refers to bacteria that do not retain crystal violet dye in the Gram staining protocol. In contrast, the wording "Gram-positive bacteria" refers to are those that are stained dark blue or violet by Gram staining.

In some embodiments, the bacteria comprise persister cells which typically constitute a small portion of a culture which is tolerant to killing by lethal doses of bactericidal antibiotics. Persister bacterial cells can be identified, for example, by exposure of logarithmic or stationary cultures of the bacteria to antibiotics using concentrations exceeding five times the minimum inhibitory concentration for each antibiotic. Persister numbers can be determined by plating the antibiotic-treated cultures on LB agar plates and subsequent counting of colony forming units representing the cell numbers which survived antibiotic exposure. Other methods for identification of persister cells will be known by a skilled person, and can be found, for example, in Moker et al. ("*Pseudomonas aeruginosa* increases formation of multi-drug-tolerant persister cells in response to quorum-sensing signaling molecules." In J Bacteriol. 2010 April; 192(7): 1946-55. Epub 2010 Jan. 22) [4].

The term "medium" as used herein indicates an environment that is suitable to support growth of microorganisms or cells. In particular, suitable medium comprise growth medium or culture medium in a liquid or gel designed to support the bacteria in vitro, as well as tissues and other suitable environment within a host (including a human host) in vivo or a tissue or biological environment in vivo or ex vivo.

In particular, in embodiments herein described interference with viability of bacteria is performed by interfering with the iron content of a medium where bacteria might be present, where the iron includes iron in a mixed oxidation state.

The term "interfere" as used herein in connection with a reference relates to a process or activity resulting in a decrease relative to the reference item compared with a baseline level. Accordingly, interference with reference to viability of bacteria refers to a decrease in viability with respect to a baseline detectable with methods to evaluate viability in a certain medium. Analogously, interference when referred to a content of a certain chemical such as iron refers to a decrease of the relevant level with respect to a baseline which can be detected with methods and techniques identifiable by a skilled person depending on the one or more chemicals to be detected. For example interference with total iron content of a medium can be verified by iron detection performed by Inductively Coupled Plasma Mass Spectrometry (ICP-MS and additional techniques identifiable by a skilled person to verify the related subtraction from the medium (see e.g. Examples section).

The term "subtraction" as used herein with reference to iron refers to the at least partial removal of iron in any of its oxidation states from a bacteria or its local environment such that the subtracted iron is not able to be acquired or otherwise used by the bacteria. Exemplary iron subtraction can be performed by ion exchange, precipitation of the iron, sequestration of the iron, and other approaches and techniques identifiable to the skilled person upon reading of the present disclosure.

In methods and systems herein described interference with iron content is performed with reference to iron in a different oxidation state, wherein the term "oxidation state" refers to the degree of oxidation of an atom in a chemical compound. Oxidation states are typically represented by integers, which can be positive, negative, or zero. In particular, the increase in oxidation state of an atom through a chemical reaction is known as an oxidation; a decrease in oxidation state is known as a reduction. Such reactions involve the formal transfer of electrons, a net gain in electrons being a reduction and a net loss of electrons being an oxidation. For pure elements, the oxidation state is zero. Oxidation states/numbers for a specific element can be determined with methodologies identifiable by a skilled. For example, two different methodologies for determining the oxidation state of elements in chemical compounds exist. A first methodology is a rule-based approach to determine how the electrons are allocated and this method is based on the rules in the IUPAC definition, and this approach is widely taught. A second methodology is a method-based on the relative electronegativity of the elements in the compound, where in simple terms the more electronegative element is assumed to take the negative charge. In the present disclosure the oxidation state is determined and expressed as an oxidation number represented by a Roman numeral placed after the element name.

In particular methods and systems herein described are directed to interfere with iron content with oxidation state Fe(II) and Fe(III). Fe(II) content in a medium and related modification determined with respect to a baseline, can be performed by the FerroZine® assay and additional methods identifiable by a skilled person (see e.g. Examples section). Total iron content and related modification can be determined with respect to a baseline and can be performed by Inductively Coupled Plasma Mass Spectrometry (ICP-MS) and additional methods identifiable by a skilled person (see e.g. Examples section). In particular, determination can be performed directly on the medium or on a sample of the medium which is used for testing the iron content.

In particular, methods and systems herein described comprise administering to the medium a Fe(II) chelator in combination with a Fe(III) chelator.

The term "chelator" or "chelating ligand" as used herein refers to a molecule capable of binding a metal ion (e.g. iron) by forming multiple bonds to the metal. In particular, chelation involves the formation or presence of two or more separate coordinate bonds between a polydentate (multiple bonded) ligand and a single central metal. These ligands can be organic compounds, and are called chelants, chelators, chelating agents, or sequestering agents. Chelators can be molecules made by the host (such as, hemoglobin, transferrin, lactoferrin, conalbumin and ferritin); or molecules made by other microorganisms (such as siderophores including Enterobactin, Yersiniabactin, Pyoverdine, Pyochelin, and others identifiable to a skilled person.); or synthetic molecules (e.g. deferoxamine, deferiprone, deferasirox, 2,2 dipyridyl, 1,10 phenanthroline, FerroZine®, EDTA, diethylenetriamine, ethylene diamine, N,N',N''-tris(2-pyridylmethyl)-1,3,5-cis,cis-triaminocyclohexane (tachpyr), and others identifiable to a skilled person).

In general, a metal chelator is a molecule capable of binding a metal and forming a molecular complex according to the generic reaction:

$$mM + lL + hH^+ = M_m L_l H_h \quad (1)$$

wherein M is the metal, L is the chelator, and $H^+$ is positive hydrogen ions with m, l and h independently equal to or higher than 1, and wherein the equilibrium constant βmlh is determined to be $$\beta mlh(M, L) = \frac{[M_m L_l H_h]}{[M]^m [L]^l [H^+]^h} \quad (2)$$

Some molecules are capable of binding more than one metal with different binding affinities which are reflected in different equilibrium constant βmlh. In those instances, a molecule is known to a skilled person as a chelator of a particular metal when the molecule is capable of specifically binding that metal. Specific binding of a metal by a chelator is determined by the molecule binding with a highest equilibrium constant βmlh for the metal separately calculated with respect to other metals according to equation (2).

For example, some molecules capable of binding Fe(II) typically can bind also Fe(III) and possibly other metals. To determine whether a molecule is a Fe(II) chelator, the equilibrium constant βmlh can be calculated for the molecule with respect to Fe(II), with respect to Fe(III) and with respect to other metals. The calculated βmlh values can be compared to determine whether the molecule is a Fe(II) chelator.

In particular, for an exemplary chelator L capable of binding Fe(II), Fe(III) and Mg(II), βmlh ($Fe^{2+}$, L)) indicating an equilibrium constant of the chelator L binding to Fe(II) can be calculated according to the following equation:

$$\beta mlh(Fe^{2+}, L) = \frac{[Fe_m^{2+} L_l H_h]}{[Fe^{2+}]^m [L]^l [H^+]^h} \quad (3)$$

βmlh ($Fe^{3+}$, L)) indicating an equilibrium constant of the chelator L binding to Fe(III) can be calculated according to the following equation:

$$\beta mlh(Fe^{3+}, L) = \frac{[Fe_m^{3+} L_l H_h]}{[Fe^{3+}]^m [L]^l [H^+]^h} \quad (4)$$

A similar calculation can be performed for βmlh ($Mg^{2+}$, L)). A comparison between βmlh ($Fe^{2+}$, L)), βmlh ($Fe^{3+}$, L)), βmlh ($Mg^{2+}$, L)) will provide an indication of whether the chelator L is a Fe(II) chelator, a Fe(III) chelator or a Mg(II) chelator.

Accordingly, a Fe(II) chelator in the sense of the present disclosure is a chelating ligand having a log of the equilibrium constant βmlh of binding Fe(II) (βmlh ($Fe^{2+}$, L)) greater than a log of the equilibrium constant βmlh of binding Fe(III) (βmlh ($Fe^{3+}$, L)) and greater than a log of the equilibrium constant βmlh of binding any other metal.

A Fe(III) chelator in the sense of the present disclosure is a chelating ligand having a log of the equilibrium constant βmlh of binding Fe(III) (βmlh ($Fe^{3+}$, L)) greater than a log of the equilibrium constant βmlh of binding Fe(II) (βmlh ($Fe^{2+}$, L)) and greater than a log of the equilibrium constant βmlh of binding any other metal.

In embodiments herein described, Fe(II) and Fe(III) chelators can be bidentate, tridentate or tetradentate ligand chelators able to respectively bind Fe(II) and Fe(III) in aqueous solution with a log of the equilibrium constant βmlh ($Fe^{2+}$, L) or βmlh ($Fe^{2+}$, L) as above described.

Exemplary Fe(II) chelators in the sense of the disclosure include FerroZine® having a log of the equilibrium constant βmlh in aqueous solutions (βmlh ($Fe^{2+}$, L)) of 15.56 [5]; [6]; [7]), 1,10 phenanthroline having the log of the equilibrium constant βmlh in aqueous solutions (βmlh ($Fe^{2+}$, L)) of 21 compared to a log of the equilibrium constant (βmlh ($Fe^{3+}$, L)) of 14.1 [8], other Fe(II) chelators listed in Robert M. Smith, Arthur E. Martell "Critical Stability Constant" Volume 6 1989 Springer US [8] and additional chelators identifiable by a skilled person by comparing the equilibrium constants of the chelators binding to Fe(II), Fe(III), and other metals.

Exemplary of Fe(III) chelators in the sense of the disclosure include Ethylenediaminetetraacetic acid (EDTA) having the log of the equilibrium constant βmlh in aqueous solutions (βmlh ($Fe^{3+}$, L)) of 27.7 compared the log of the equilibrium constant βmlh in aqueous solutions (βmlh ($Fe^{2+}$, L)) of 16.1, desferrin-ferrioxamine B having the log of the equilibrium constant βmlh in aqueous solutions (βmlh ($Fe^{3+}$, L)) of 31.9 compared with the log of the equilibrium constant βmlh in aqueous solutions (βmlh ($Fe^{2+}$, L)) of 18.7, and additional chelators such as Trans-1,2-Cyclohexanediaminetetraacetic Acid (CDTA), Nitrilotriacetic acid (NTA), iminodiacetic acid (IDA), citrate conalbumin, Desferri-ferrioxamine B, all siderophores (ranging from bidentate to hexadentate), other chelators listed in Robert M. Smith, Arthur E. Martell "Critical Stability Constant" Volume 6 1989 Springer US [8] and further chelators identifiable by a skilled person by comparing the equilibrium constants of the chelators binding to Fe(II), Fe(III) and other metals.

Additional equilibrium constant βmlh of chelators binding to metals can be found in the following excerpt from Table 6.3 of Principles and Applications of Aquatic Chemistry Wiley and Sons 1993 [9] showing the log of the equilibrium constant βmlh for various multidentate ligands in aqueous environment (first column) and other environment as will be understood by a skilled person.

TABLE 6.3

| | | | | | | | | |
|---|---|---|---|---|---|---|---|---|
| Stability Constants for Formation of Complexes and Solids from Metals and Ligands | | | | | | | | |
| | Ethylenediamine | NTA | EDTA | CDTA | IDA | Picolinate | Cysteine | Desferri-ferrioxamine B |
| $H^+$ | HL 9.93 | HL 10.33 | HL 11.12 | HL 13.28 | HL 9.73 | HL 5.39 | HL 10.77 | HL 10.1 |
| | $H_2L$ 16.78 | $H_2L$ 13.27 | $H_2L$ 17.8 | $H_2L$ 20.0 | $H_2L$ 12.63 | $H_2L$ 6.40 | $H_2L$ 19.13 | $H_2L$ 19.4 |
| | | $H_3L$ 14.92 | $H_3L$ 21.04 | $H_3L$ 23.98 | $H_3L$ 14.51 | | $H_3L$ 20.84 | $H_3L$ 27.8 |
| | | $H_4L$ 16.02 | $H_4L$ 23.76 | $H_4L$ 26.62 | | | | |
| | | | $H_5L$ 24.76 | $H_5L$ 28.34 | | | | |
| $Na^+$ | | NaL 1.9 | NaL 2.5 | | NaL 0.8 | | | |
| $K^+$ | | | KL 1.7 | | | | | |
| $Ca^+$ | | CaL 7.6 | CaL 12.4 | CaL 15.0 | CaL 3.5 | CaL 2.2 | | CaL 3.5 |
| | | | CaHL 16.0 | | | $CaL_2$ 3.8 | | |
| $Mg^{2+}$ | MgL 0.4 | MgL 6.5 | MgL 10.6 | MgL 12.8 | MgL 3.8 | MgL 2.6 | | MgL 5.2 |
| | | | MgHL 15.1 | | | $MgL_2$ 4.0 | | |
| $Sr^{2+}$ | | SrL 6.3 | SrL 10.5 | SrL 12.4 | SrL 3.1 | SrL 1.8 | | SrL 3.1 |
| | | | SrHL 14.9 | | | $SrL_2$ 3.0 | | |
| $Ba^{2+}$ | | BaL 5.9 | BaL 9.6 | BaL 10.5 | Ba 2.5 | BaL 1.6 | | |
| | | | BaHL 14.6 | BaHL 17.8 | | | | |
| $Cr^{3+}$ | | | CrL 26.0 | | CrL 12.2 | | | |
| | | | CrHL 28.2 | | CrL 23.2 | | | |
| | | | CrOHL 32.2 | | | | | |
| $Al^{3+}$ | | AlL 13.4 | AlL 18.9 | AlL 22.1 | AlL 9.9 | | | |
| | | AlOHL 22.1 | AlHL 21.6 | AlHL 24.3 | $AlL_2$ 17.5 | | | |
| | | | AlOHL 26.6 | | | | | |
| | | | $Al(OH)_2L$ 30.0 | AlOHL 28.1 | | | | |
| $Fe^{3+}$ | | FeL 17.9 | FeL 27.7 | FeL 32.6 | FeL 12.5 | $FeL_2$ 13.9 | | FeL 31.9 |
| | | $FeL_2$ 26.3 | FeHL 29.2 | FeOHL 36.5 | | | | FeHL 32.6 |
| | | | FeOHL 33.8 | | | $FeOHL_2$ 24.9 | | |
| | | | $Fe(OH)_2L$ 37.7 | | | | | |
| $Mn^+$ | MnL 2.8 | MnL 8.7 | MnL 15.6 | MnL 19.2 | | MnL 4.0 | | |
| | $MnL_2$ 3.7 | $MnL_2$ 11.6 | MnHL 19.1 | MnHL 22.4 | | $MnL_2$ 7.1 | | |
| | $MnL_3$ 5.8 | | | | | $MnL_3$ 8.8 | MnL 5.6 | |
| $Fe^{2+}$ | FeL 4.3 | FeL 9.6 | FeL 16.1 | FeL 20.8 | FeL 6.7 | FeL 5.3 | | FeHL 18.7 |
| | $FeL_2$ 7.7 | $FeL_2$ 13.6 | FeHL 19.3 | FeHL 23.9 | $FeL_2$ 11.0 | $FeL_2$ 9.7 | | $FeH_2L$ 21.0 |
| | $FeL_3$ 9.7 | | FeOHL 20.4 | | | $FeL_3$ 13.0 | | |
| | | | $Fe(OH)_2L$ 23.7 | | | | | |
| $Co^{2+}$ | CoL 6.0 | CoL 11.7 | CoL 18.1 | CoL 21.4 | CoL 7.9 | CoL 6.4 | | CoL 11.2 |
| | $CoL_2$ 10.8 | $CoL_2$ 15.0 | CoHL 21.5 | CoHL 24.7 | $CoL_2$ 13.2 | $CoL_2$ 11.3 | | CoHL 18.0 |
| | $CoL_3$ 14.1 | CoOHL 14.5 | | | | $CoL_3$ 14.8 | | CoHL 23.6 |
| $Ni^{2+}$ | NiL 7.4 | NiL 12.8 | NiL 20.4 | NiL 22.1 | NiL 9.1 | NiL 7.2 | NiL 10.7 | NiL 11.8 |
| | $NiL_2$ 13.6 | $NiL_2$ 17.0 | NiHL 24.0 | NiHL 25.4 | $NiL_2$ 15.7 | $NiL_2$ 12.5 | | NiHL 18.3 |
| | $NiL_3$ 17.9 | NiOHL 15.5 | NiOHL 21.8 | | | $NiL_3$ 17.9 | $NiL_2$ 20.9 | $NiH_2L$ 23.8 |
| $Cu^{2+}$ | CuL 10.5 | CuL 14.2 | CuL 20.5 | CuL 23.7 | CuL 11.5 | CuL 8.4 | Cu(II) | CuL 15.0 |
| | $CuL_2$ 19.6 | $CuL_2$18.1 | CuHL 23.9 | CuHL 27.3 | $CuL_2$ 17.6 | $CuL_2$ 15.6 | →Cu(I) | CuHL 24.1 |
| | CuOHL 11.8 | CuOHL 18.6 | CuOHL 22.6 | | | | | $CuH_2L$ 27.0 |
| $Zn^{2+}$ | ZnL 5.7 | ZnL 12.0 | ZnL 18.3 | ZnL 21.1 | ZnL 8.2 | ZnL 5.7 | ZnL 10.1 | ZnL 11.0 |
| | $ZnL_2$ 10.6 | $ZnL_2$ 14.9 | ZnHL 21.7 | ZnHL 24.4 | $ZnL_2$ 13.5 | $ZnL_2$ 10.3 | ZnL 19.1 | ZnHL 17.5 |
| | $ZnL_3$ 13.9 | ZnOHL 15.5 | ZnOHL 19.9 | | | $ZnL_3$ 13.6 | ZnHL 16.4 | $ZnH_2L$ 22.9 |
| $Pb^{2+}$ | PbL 7.0 | PbL 12.6 | PbL 19.8 | PbL 22.1 | PbL 8.3 | PbL 5.0 | PbL 12.5 | |
| | $PbL_2$ 8.5 | | PbHL 23.0 | PbHL 25.3 | | $PbL_2$ 8.6 | | |
| $Hg^{2+}$ | HgL 14.3 | HgL 15.9 | HgL 23.5 | HgL 26.8 | HgL 11.7 | HgL 8.1 | HgL 15.3 | |
| | $HgL_2$ 23.2 | | HgHL 27.0 | HgHL 30.3 | | $HgL_2$ 16.2 | | |
| | HgOHL 24.2 | | HgOHL 27.7 | HgOHL 29.7 | | | | |
| | $HgHL_2$ 28.0 | | | | | | | |
| $Cd^{2+}$ | CdL 5.4 | CdL 11.1 | CdL 18.2 | CdL 21.7 | CdL 6.6 | CdL 5.0 | | CdL 8.8 |
| | $CdL_2$ 9.9 | $CdL_2$ 15.1 | CdHL 21.5 | CdHL 25.1 | $CdL_2$ 11.1 | $CdL_2$ 8.3 | | CdHL 16.2 |
| | $CdL_3$ 11.7 | CdOHL 13.4 | | | | $CdL_3$ 11.4 | | $CdH_2L$ 22.7 |
| $Ag^{2+}$ | AgL 4.7 | AgL 5.8 | AgL 8.2 | AgL 9.9 | | AgL 3.6 | | |
| | $AgL_2$ 7.7 | | AgHL 14.9 | | | $AgL_2$ 6.1 | | |
| | $AgHL_2$11.9 | | | | | | | |

In general, Fe(II) chelators can be detected by various spectroscopic measurements for example by first displacing them from iron by a stronger chelator (for example, 4,4'-bipyridine, phenanthroline, EDTA, FerroZine®) and using various spectroscopic methods to analyze for the unbound chelator (e.g., NMR and IR spectroscopy, mass spectrometry, HPLC). Also, the iron-chelator complex can be characterized directly, such as in cases where the iron chelator binds iron more favorably than other chelates one would use to displace it, using the aforementioned spectroscopic techniques (for example, paramagnetic NMR spectroscopy), in addition to X-ray crystallography, combustion analysis, or by standard electrochemical techniques. In particular, in embodiments herein described, the chelating ability of a candidate chelator as well as different chelating ability among bidentate, tridentate tetradentate chelators such as degree of complexation and other feature that might be used by a skilled person to identify an Fe(II) chelator or chelator combination for a certain application can be identified by a combination of methods herein described to determine the local coordination environment of Fe and the related oxidation state. For example, a skilled practitioner can titrate a potential chelator and study its binding affinity by, for example, optical spectroscopy (UV-vis) and compare this binding affinity with reference data (e.g. literature data) available for known binding affinities of many classes of chelators, including those that are bidentate, tridentate, tetradentate, and additional class of chelators identifiable by a skilled person.

Analogously for what already indicated for the Fe(II) chelator, an Fe(III) chelator can also be identified as a molecule capable of chelating Fe(III) with enhanced affinity compared to the affinity of a collection of similar nonchelating (monodentate) ligands for the same metal. Reactions (1) to (4) above also apply for the identification of Fe(III) chelating ligand.

The same methodologies and techniques described in connection with detection of Fe(II) apply for Fe(III) as will be understood by a skilled person.

In particular, in embodiments herein described, the chelating ability of a candidate Fe(III) chelator as well as different chelating ability among bidentate, tridentate tetradentate chelators such as degree of complexation and other feature that can be used by a skilled person to identify an Fe(III) chelator or chelator combination for a certain application can be identified by a combination of methods herein described to determine the local coordination environment of Fe and the related oxidation state. Reference is made to the exemplary techniques indicated herein for Fe(II) such as various spectroscopic measurements (e.g., NMR and IR spectroscopy, mass spectrometry, HPLC) X-ray crystallography, combustion analysis, or by standard electrochemical techniques which can be performed to detect the binding affinity of a candidate Fe(III) chelator which can then be compared to reference data to identify the chelating ability of the compound.

In some embodiments of methods and systems herein described, an Fe(II) chelator and an Fe(III) chelator can be administered in an amount of Fe(II) chelator of between 1 nM-10 mM and of Fe(III) chelator in an amount ranging between 1 nM-10 mM (see, for example, Examples 3-4).

In some embodiments, the composition comprises FerroZine® in an amount ranging between 1 nM-10 mM and conalbumin in an amount ranging between 1 nM-10 mM. In some embodiments, FerroZine® of the composition is in an amount ranging between 10-1000 μM and conalbumin of the composition is in an amount ranging between 10-1000 μM (see, for example, Examples 1-4).

In some embodiments, the Fe(II) chelator and an Fe(III) chelator can be administered in a proportion 2:1 under aerobic or anaerobic conditions. In some embodiments the Fe(II) chelator and an Fe(III) chelator can be administered in a proportion 1:1 under aerobic or anaerobic conditions (see Examples 10 and 11) and in particular under aerobic conditions (see Example 12).

The concentrations of the Fe(II) and Fe(III) chelator and their proportion depends on the anaerobic/aerobic conditions of the local iron environment, the oxidation state of the target iron that needs to be chelated, the concentration of Fe(II) and Fe(III) and their percentage, the degree of complexation such as bidentate, tridentate, tetradentate or pentavalent and many other factors known to a skilled person in the art. The appropriate minimal amount of Fe(II) and/or Fe(III) chelators can be provided in concentrations at least equal to the amount of the target ion in a specific oxidation state which can be detected with techniques identifiable by a skilled person. In some embodiments, Fe(II) and Fe(III) chelators can be provided in an amount selected to maximize chelation of Fe(II) and Fe(III) while minimizing non-specific chelation of other metals such as calcium in view of the total iron concentration and the equilibrium constant βmlh of the chelators for Fe (II), Fe (III) and the other metals.

In some embodiments, the concentrations of the Fe(II) and Fe(III) chelators and their proportions can be determined based on measurements of the Fe oxidation states of a sample performed over time with techniques and methods identifiable by a skilled person. In particular, in some embodiments herein described, the Fe(II) and Fe(III) chelator concentrations are provided in direct correlation to the oxidation-reduction potentials of the sample. For example, the more reduced the sample is, the higher percentage of Fe(II) exists in the sample, indicating that a higher amount of Fe(II) chelators needs to be administered.

In some embodiments, the composition comprises conalbumin in an amount of approximately 100 μM (see, for example, Examples 1-4).

In some embodiments, the composition comprises FerroZine® in an amount of approximately 100 μM (see, for example, Examples 1-4).

In some embodiments, the composition comprises FerroZine® in an amount of approximately 200 μM (see, for example, Examples 1-4).

In some embodiments, the composition comprises FerroZine® and conalbumin, in which the FerroZine® is in an amount higher than the amount of conalbumin. For example, the composition comprises conalbumin in an amount of approximately 100 μM and FerroZine® in an amount of approximately 200 μM (see, for example, Examples 1-4).

In some embodiments, a method and system to interfere with viability of bacteria is described, the method comprising contacting Fe(II) and Fe (III) chelators with the bacteria to reduce survivability and/or antibiotic resistance of the bacteria.

In some embodiments, the Fe(II) chelator is in the form of a protein and/or a chemical compound. In an embodiment, the activation of the Fe(II) chelator can be performed by adding the Fe(II) chelator to a bacterial culture in a way similar to the use of conalbumin to chelate Fe(III) described herein (see, for example, Example 3).

In some embodiments, the Fe(II) chelator is FerroZine®, and activating of the Fe(II) chelator can be performed by delivering FerroZine® into, for example, the mucus environment of bacteria (see, for example, Examples 1-4).

In some embodiments, combined administration of Fe(II) chelators and Fe(II) chelators is performed according to methods and systems herein described comprising impairing bacterial biofilm development in the bacteria.

As used herein the term "biofilm" indicates an aggregate of microorganisms in which cells adhere to each other on or at an interface. These adherent cells are frequently embedded within a self-produced matrix of extracellular polymeric substance (EPS). Biofilms can form on living or non-living surfaces and can be prevalent in natural, industrial and hospital settings. The microbial cells growing in a biofilm are physiologically distinct from planktonic cells of the same organism, which, by contrast, are single-cells that can float or swim in a liquid medium. Formation of a biofilm begins with the attachment of free-floating microorganisms to a surface. Establishment of a mature biofilm is associated with high level antibiotic tolerance that exceeds the ability of planktonic cells to resist antimicrobial agents. Methods to quantify and measure biofilms will be known to a skilled person and can include, for example, the COMSTAT method of Heydorn et al. (Microbiology 2000, 146, 2395-2407;). [10]

In some embodiments, the bacterial biofilm development can be facilitated by phenazine-mediated iron acquisition of bacteria. Iron has been shown to be involved as a signal in bacterial biofilm formation (see, for example, Banin et al. PNAS, 2005, 102, 11076-11081) [11]. Phenazines have been shown to mediate iron acquisition in bacterial biofilm development, for example, by reduction of insoluble Fe(III) to more soluble Fe(II) (See, for example, Wang et al. J. Bacteriol. 2011, 193, 3606-3617, and Examples 1-6). [12]

In some embodiments, reducing the amount of Fe(II) available to a bacterial culture is performed by a suitable addition of iron chelator such as FerroZine®, to the bacterial culture (see, for example, Examples 1-4). Other iron-binding molecules usable in this method would be identifiable to skilled person and can include, for example, 1, 10 phenanthroline.

In some embodiments, the Fe(II) chelator is in the form of an aerosol and can thus be delivered topically, e.g. directly into the lungs of an individual and in particular a patient. Methods to deliver the Fe(II) chelator into the lungs of a patient can be identified by a skilled person using, for example, the methods of Corkery ("Inhalable Drugs for Systemic Therapy" Respiratory Care 2000, 45, 931-835) [13] (see, for example, Examples 1-4).

In other embodiments, the Fe(II) chelator is a host protein, and activating a Fe(II) chelator comprises regulating of one or more host genes encoding a host Fe(II) chelator. Fe(II) chelating host proteins are identifiable to a skilled person can include, but not be limited to, apoferritin and methods for regulating the host genes encoding the host Fe(II) chelators can be identified by a skilled person and can include, but not be limited to, use of the siRNA techniques described above.

In some embodiments, reducing amount of Fe(III) available to a bacterial culture is performed by a suitable addition of iron chelator such as conalbumin, to the bacterial culture. As seen in Example 3 and, for example, and in Wang et al. (J. Bacteriol. 2011, 193, 3606-3617) [12] the biofilm development was impaired when in presence of conalbumin. Other iron-binding molecules usable in this method would be identifiable to skilled person and can include, for example, EDTA, desferrioxamine, hemoglobin, transferrin, lactoferrin, and ferritin.

In some embodiments, the Fe(III) chelator is in the form of a protein and/or a chemical compound (see Examples 1-4). In exemplary embodiment, the activation of the Fe(III) chelator can be performed by adding the Fe(III) chelator to a bacterial culture the in a way similar to the use of conalbumin to chelate Fe(III) to inhibit its reduction to Fe(II) described above in reference to Example 3 below. In another non-limiting example, a DNA sequence of a Fe(III) chelating protein delivered by introduction of the DNA sequence into a bacteria via a virus, or another technique identifiable to a skilled person upon reading of the present disclosure, and the DNA sequence expressed in the bacteria to produce the Fe(III) chelating protein. Appropriate Fe(III) chelating proteins can include, but are not limited to, hemoglobin, transferrin, lactoferrin, and ferritin.

In some embodiments, the Fe(III) chelator is conalbumin, and activating a Fe(III) chelator can be performed by delivering conalbumin into the mucus environment of bacteria (see, for example, Examples 1-4).

In some embodiments, the Fe(III) chelator is in the form of an aerosol and can thus be delivered directly into the lungs of an individual. Methods to deliver the Fe(III) chelator into the lungs of an individual (e.g. a patient) can be identified by a skilled person using, for example, the methods of Corkery ("Inhalable Drugs for Systemic Therapy" Respiratory Care 2000, 45, 931-835) [13] (see, for example, Examples 1-4).

In other embodiments, the Fe(III) chelator is a host protein, and activating a Fe (III) chelator comprises regulating of one or more host genes encoding a host Fe(III) chelator. Fe(III) chelating host proteins are identifiable to a skilled person can include, but not be limited to, hemoglobin, transferrin, lactoferrin, conalbumin, and ferritin, and methods for regulating the host genes encoding the host Fe(III) chelators can be identified by a skilled person and can include, but not be limited to, use of the siRNA techniques described above (see, for example, Examples 1-4).

In some embodiments herein described, iron chelation can be used to inhibit pathogenic microbial biofilms in vitro and in vivo.

In some embodiments, Fe(II) and Fe(III) chelators can be activated in combination to substantially minimize and/or disrupt biofilm growth as exemplified in Examples 3-4. In these embodiments, Fe(II) and Fe(III) chelators can act synergistically to substantially prevent and/or disrupt biofilm growth as also exemplified in Examples 3-4.

In some embodiments, the Fe(II) chelator to be used in combination with an Fe(III) chelator is FerroZine®. In some embodiments the Fe(III) chelator to be used in combination with an Fe(II) chelator is conalbumin. In some embodiments, the Fe(II) chelator and Fe(III) chelator administered in combination can be FerroZine® and conalbumin (see, for example, Examples 2-4).

In particular, in some embodiments, the combination of activation of Fe(II) and Fe(III) chelators in combination can be used to target mature biofilms. Mature biofilms are of significance, for example, because increased resistance to antibiotics (see, for example, Ito et al. Applied and Environmental Microbiology 2009, 75, 4093-4100 and Example 4) [14].

Thus, in some embodiments, a method for interfering with viability of bacteria comprises activating a combination of Fe(II) and Fe(III) chelators to substantially prevent and/or disrupt biofilm growth. In these embodiments, Fe(II) and Fe(III) chelators can act synergistically to substantially prevent and/or disrupt biofilm growth and can be used to target mature biofilms. (See, for example, Example 4).

In some embodiments, the combined Fe(II) and Fe(III) chelators can be used for minimizing contamination of a surface e.g. surface of instrumentations (see e.g. the flow cytometer of Example 12).

In some embodiments, the combined Fe(II) and Fe(III) chelators can be used in vivo in methods and systems for treating and/or preventing a bacterial infection in an individual is described. The method comprises administering to the individual an effective amount of one or more Fe(II) chelators and Fe(III) chelators. In particular, in some embodiments, administering of one or more Fe(II) chelators and Fe(III) chelators can be performed in combination with one or more antibiotics and/or other antimicrobials. The system comprises one or more Fe(II) chelators and Fe(III) chelators and an antibiotic and/or other antimicrobial. In some embodiments of methods and systems, the bacteria comprise persister cells.

The ability of the combination of Fe(II) and Fe(III) chelators in substantially preventing and/or disrupting biofilm growth can be due to the appreciable levels of ferrous iron [Fe(II)] which can exist in the majority of CF lung which can compromise Fe(III) chelation therapy under hypoxic or anoxic conditions. Such appreciable levels of Fe(II) can be due to localized hypoxic microenvironments exist which can stabilize Fe(II) (see, for example, Examples 1-4).

Thus, in some embodiments, a treatment for cystic fibrosis (CF) patients comprises administering Fe(II) and Fe(III) chelators in combination to substantially prevent and/or disrupt biofilm growth. (See, for example, Examples 1-4).

In some embodiments, compositions for substantially preventing and/or reducing biofilms are described. The composition comprises one or more Fe(II) chelators and Fe(III) chelators to reduce survivability of bacteria. (See, for example, Examples 1-4).

In some embodiments, the composition comprises an Fe(II) chelator and an Fe(III) chelator. In some embodiments, the Fe(II) chelator is FerroZine® and is comprised in the composition in an amount ranging between 1 nM-10 mM. In some embodiments, the Fe(III) chelator is conalbumin and is comprised in the composition in an amount ranging between 1 nM-10 mM. (see, for example, Examples 3-4).

In some embodiments, the composition comprises FerroZine® in an amount ranging between 10-1000 μM and conalbumin in an amount ranging between 10-1000 μM (see, for example, Examples 1-4). In some embodiments, FerroZine® is in an amount ranging between 10-250 μM and conalbumin in an amount ranging between 10-250 μM.

In some embodiments, the concentrations of the Fe(II) chelators such as FerroZine® and the Fe(III) chelators such as conalbumin and their proportions correlate to the stage of the disease. In exemplary embodiments shown in Examples 5-6, the total iron concentration and the proportion of Fe(II) increases with the severity of the disease. The administration of the Fe(II) and Fe(III) chelators including the concentration and proportions of Fe(II) and Fe(III) chelators therefore can be modified accordingly. For example, the administration can be adjusted based on the stage and/or severity of CF by increasing the total amount of the Fe chelator and/or particularly the proportion of the Fe(II) chelator as will be understood by a skilled person upon reading of the present disclosure.

In some embodiments, the composition comprises FerroZine® in an amount of approximately 200 μM (see, for example, Examples 1-4).

In some embodiments, the composition comprises conalbumin in an amount of approximately 100 μM (see, for example, Examples 1-4).

In some embodiments, the CF airways of sick patients have been tested to have a total iron of about 10 μM. In such embodiments, the composition for treating the CF patients comprises FerroZine® in an amount ranging from about 10-250 μM and conalbumin in an amount ranging from about 10-250 μM.

In some embodiments, the composition comprising administering a combination of the Fe(II) chelator and the Fe(III) chelator to reduce biofilm accumulation by greater than approximately 20%. In some embodiments, composition comprising the combination of the Fe(II) chelator and the Fe(III) chelator reduces biofilm accumulation by greater than approximately 50% (see, for example, Examples 1-4).

In some embodiments, the delivery of Fe(II) and Fe(III) chelators such as FerroZine® and conalbumin to treat a patient in need can be administered via inhalation therapy, intravenous (IV), oral routes or intramuscularly, depending upon the oral bioavailability, side-effect profiles and the maximum dose for single administration of the chelators as well as the clinical response of the patient such as compliance, absorption and efficacy and many other factors known to a skilled person in the clinical art.

In some embodiments, a method and system to interfere with the viability of bacteria is described, the method comprising the chelation of Fe(II) alone/or Fe(III) to reduce survivability and/or antibiotic resistance of the bacteria.

In some embodiments, Fe(II) and Fe(III) chelators can be activated in combination to substantially prevent and/or disrupt biofilm growth as exemplified in Examples 1-4. In these embodiments, Fe(II) and Fe(III) chelators can act synergistically to substantially prevent and/or disrupt biofilm growth as also exemplified in Examples 1-4. In addition, such treatments can act synergistically with conventional antibiotics such as tobramycin [15].

In some embodiments, the Fe(II) chelator to be used in combination with an Fe(III) chelator is FerroZine®. In some embodiments the Fe(III) chelator to be used in combination with an Fe(II) chelator is conalbumin. In some embodiments, the Fe(II) chelator and Fe(III) chelator administered in combination can be FerroZine® and conalbumin (see, for example, Examples 1-4).

In particular, in some embodiments, the combination of activation of Fe(II) and Fe(III) chelators in combination can be used to target mature biofilms. Mature biofilms are of significance, for example, because increased resistance to antibiotics (see, for example, Ito et al. Applied and Environmental Microbiology 2009, 75, 4093-4100) [14].

Thus, in some embodiments, a method for interfering with viability of bacteria comprises activating a combination of Fe(II) and Fe(III) chelators to substantially prevent and/or disrupt biofilm growth. In these embodiments, Fe(III) and Fe(II) chelators can act synergistically to substantially prevent and/or disrupt biofilm growth and can be used to target mature biofilms. (See Example 4).

The ability of the combination of Fe(III) and Fe(II) chelators in substantially preventing and/or disrupting biofilm growth can be due to the appreciable levels of ferrous iron [Fe(II)] which can exist in the majority of CF lung which can compromise Fe(III) chelation therapy under hypoxic conditions. Such appreciable levels of Fe(II) can be due to localized hypoxic microenvironments exist which can stabilize Fe(II) (see, for example, Examples 1-4).

Thus, in some embodiments, a treatment for cystic fibrosis (CF) patients comprises administering Fe(III) and Fe(II)

chelators in combination to substantially prevent and/or disrupt biofilm growth. (See, for example, Examples 1-4).

In some embodiments, compositions for substantially preventing and/or reducing biofilms are described. The composition comprises one or more agents able to chelate Fe(II) and/or Fe(III) to reduce survivability of bacteria. (See, for example, Examples 1-4).

In some embodiments, the composition comprises an Fe(II) chelator and an Fe(III) chelator. In some embodiments, the Fe(II) chelator is FerroZine® and is comprised in the composition in an amount ranging between 10-1000 µM. In some embodiments, the Fe(III) chelator is conalbumin and is comprised in the composition in an amount ranging between 10-1000 µM (see, for example, Examples 3-4).

In some embodiments, the composition comprises FerroZine® in an amount ranging between 10-1000 µM and conalbumin FerroZine® in an amount ranging between 10-1000 µM (see, for example, Examples 1-4).

In some embodiments, the composition comprises FerroZine® in an amount of approximately 200 µM (see, for example, Examples 1-4).

In some embodiments, the composition comprises conalbumin in an amount of approximately 100 µM (see, for example, Examples 1-4).

In some embodiments, the composition comprising a combination of the Fe(II) chelator and the Fe(III) chelator reduces biofilm accumulation by greater than approximately 20%. In some embodiments, composition comprising the combination of the Fe(II) chelator and the Fe(III) chelator reduces biofilm accumulation by greater than approximately 50% (see, for example, Examples 1-4).

Further, in other embodiments, a method and system for treating and/or preventing a bacterial infection in an individual is described. The method comprises administering an effective amount of one or more agents able to selectively chelate Fe(II) and/or Fe(III), in particular in combination with an antibiotic and/or other antimicrobial. The system comprises one or more agents able to specifically chelate Fe(II) and/or Fe(III) and an antibiotic and/or other antimicrobial (see, for example, Examples 1-4).

In particular, in some embodiments, a method for treating and/or preventing bacterial infection associated with cystic fibrosis is described. The method comprises administering a therapeutically effective amount of a combination of Fe(III) and Fe(II) chelators to an individual (see, for example, Examples 1-4).

In some embodiments, the administering can be performed by way of an aerosol comprising the Fe(III) and Fe(II) chelators, however other forms of administration, identifiable by a skilled person, can be used.

In some embodiment, the administering of the Fe(III) and Fe(II) chelators substantially prevents and/or disrupts biofilm growth in the lungs of an individual infected with the bacteria, such as a CF patient (see, for example, Examples 1-4).

In some embodiments, Fe(III) and Fe(II) chelators can act synergistically to substantially prevent and/or disrupt biofilm growth and can be used to target mature biofilms (see, for example, Examples 1-4).

In some embodiments, the Fe(II) chelator is FerroZine® and a therapeutically effective amount ranges from approximately 10-1000 µM. More particularly, in some embodiments, the therapeutically effective amount of FerroZine® is approximately 200 µM (see, for example, Examples 1-4).

In some embodiments, the Fe(III) chelator is conalbumin and a therapeutically effective amount ranges from approximately 10-1000 µM. More particularly, in some embodiments, the therapeutically effective amount of conalbumin is approximately 100 µM (see, for example, Examples 1-4).

The term "treatment" as used herein indicates any activity that is part of a medical care for, or deals with, a condition, medically or surgically.

The term "prevention" as used herein indicates any activity which reduces the burden of mortality or morbidity from a condition in an individual. This takes place at primary, secondary and tertiary prevention levels, wherein: a) primary prevention avoids the development of a disease; b) secondary prevention activities are aimed at early disease treatment, thereby increasing opportunities for interventions to prevent progression of the disease and emergence of symptoms; and c) tertiary prevention reduces the negative impact of an already established disease by restoring function and reducing disease-related complications.

The term "condition" as used herein indicates a physical status of the body of an individual (as a whole or as one or more of its parts), that does not conform to a standard physical status associated with a state of complete physical, mental and social well-being for the individual. Conditions herein described include but are not limited disorders and diseases wherein the term "disorder" indicates a condition of the living individual that is associated to a functional abnormality of the body or of any of its parts, and the term "disease" indicates a condition of the living individual that impairs normal functioning of the body or of any of its parts and is typically manifested by distinguishing signs and symptoms.

The term "individual" as used herein in the context of treatment includes a single biological organism, including but not limited to, animals and in particular higher animals and in particular vertebrates such as mammals and in particular human beings.

The wording "selective", "specific" "specifically" or "specificity" as used herein with reference to the binding of a first molecule to second molecule refers to the recognition, contact and formation of a stable complex between the first molecule and the second molecule, together with substantially less to no recognition, contact and formation of a stable complex between each of the first molecule and the second molecule with other molecules that may be present. Exemplary specific bindings are antibody-antigen interaction, cellular receptor-ligand interactions, polynucleotide hybridization, enzyme substrate interactions etc. The term "specific" as used herein with reference to a molecular component of a complex, refers to the unique association of that component to the specific complex which the component is part of. The term "specific" as used herein with reference to a sequence of a polynucleotide refers to the unique association of the sequence with a single polynucleotide which is the complementary sequence. By "stable complex" is meant a complex that is detectable and does not require any arbitrary level of stability, although greater stability is generally preferred. The term "selective" "specific" "specifically" or "specificity" as used herein with reference to a chemical or biological activity of a first molecule to second molecule of a certain bacteria or group of bacteria refers to the ability of the first molecule to direct the activity towards the second molecule, together with substantially less to no activity between the first molecule and molecules that may be present of organisms other than the bacteria or group of bacteria.

In some embodiments, the method for treating and/or preventing a bacterial infection in an individual comprises inactivation of phenazines and/or one or more phenazine related pathways of the bacteria as describe in any of the above embodiments. In particular, the inactivation of the phenazines and/or one or more phenazine related pathways of the bacteria performed as describe in any of the above embodiments will be recognized by the skilled person as not interfering in a deleterious manner with the normal biochemical pathways of the individual.

An "antimicrobial" as described herein indicates a substance that kills or inhibits the growth of microorganisms such as bacteria, fungi, or protozoans. Antimicrobial either kills microbes (microbiocidal) or prevent the growth of microbes (microbiostatic)

The terms "detect" or "detection" as used herein indicates the determination of the existence, presence or fact of a target in a limited portion of space, including but not limited to a sample, a reaction mixture, a molecular complex and a substrate. The "detect" or "detection" as used herein can comprise determination of chemical and/or biological properties of the target, including but not limited to ability to interact, and in particular bind, other compounds, ability to activate another compound and additional properties identifiable by a skilled person upon reading of the present disclosure. The detection can be quantitative or qualitative. A detection is "quantitative" when it refers, relates to, or involves the measurement of quantity or amount of the target or signal (also referred as quantitation), which includes but is not limited to any analysis designed to determine the amounts or proportions of the target or signal. A detection is "qualitative" when it refers, relates to, or involves identification of a quality or kind of the target or signal in terms of relative abundance to another target or signal, which is not quantified.

In some embodiments, an antimicrobial is described. The antimicrobial comprises one or more agents able to inactivate a phenazine and/or a phenazine related pathway in the bacteria to reduce antibiotic resistance and/or survivability of bacteria and optionally a compatible vehicle for effective administrating and/or delivering of the one or more agents to an individual.

In some embodiments, a pharmaceutical composition for the treatment of cystic fibrosis is described. The pharmaceutical composition for the treatment of cystic fibrosis comprises one or more agents able to inactivate a phenazine and/or a phenazine related pathway in the bacteria to reduce survivability of bacteria. In some embodiments the pharmaceutical composition for the treatment of cystic fibrosis comprises an Fe(II) chelator and an Fe(III) chelator.

In some embodiments the pharmaceutical composition for the treatment of cystic fibrosis further comprises a suitable vehicle for effective administrating and/or delivering of the one or more agents to an individual.

In some embodiments, the Fe(II) chelator is FerroZine® and is comprised in the pharmaceutical composition in an amount ranging between 10-1000 µM. In some embodiments, the Fe(III) chelator is conalbumin and is comprised in the pharmaceutical composition in an amount ranging between 10-1000 µM (see, for example, Examples 1-5 and 19-22).

In some embodiments, the pharmaceutical composition comprises FerroZine® in an amount ranging between 10-1000 µM and conalbumin in an amount ranging between 10-1000 µM (see, for example, Examples 1-5 and 19-22).

In some embodiments, the pharmaceutical composition comprises FerroZine® in an amount of approximately 200 µM (see, for example, Examples 1-5 and 19-22).

In some embodiments, the pharmaceutical composition comprises conalbumin in an amount of approximately 100 µM (see, for example, Examples 1-5 and 19-22).

In some embodiments, the pharmaceutical composition comprising a combination of the Fe(II) chelator and the Fe(III) chelator reduces biofilm accumulation by greater than approximately 20%. In some embodiments, the pharmaceutical composition comprising the combination of the Fe(II) chelator and the Fe(III) chelator reduces biofilm accumulation by approximately greater than 20% or by approximately 50% (see, for example, Examples 1-4).

The term "vehicle" as used herein indicates any of various media acting usually as solvents, carriers, binders or diluents for PSA comprised in the composition as an active ingredient.

In some embodiments, the antimicrobial further comprises antibiotic and/or an additional antimicrobial.

In some embodiments, the vehicle is a pharmaceutically acceptable vehicle and the composition is a pharmaceutical composition.

In particular some embodiments, the one or more agents can be included in pharmaceutical compositions together with an excipient or diluent and optionally with one or more antibiotics and/or other antimicrobial.

The term "excipient" as used herein indicates an inactive substance used as a carrier for the active ingredients of a medication. Suitable excipients for the pharmaceutical compositions herein disclosed include any substance that enhances the ability of the body of an individual to absorb the one or more agents. Suitable excipients also include any substance that can be used to bulk up formulations with the one or more agents to allow for convenient and accurate dosage. In addition to their use in the single-dosage quantity, excipients can be used in the manufacturing process to aid in the handling of the one or more agents. Depending on the route of administration, and form of medication, different excipients may be used. Exemplary excipients include but are not limited to anti-adherents, binders, coatings disintegrants, fillers, flavors (such as sweeteners) and colors, glidants, lubricants, preservatives, sorbents.

The term "diluent" as used herein indicates a diluting agent which is issued to dilute or carry an active ingredient of a composition. Suitable diluent include any substance that can decrease the viscosity of a medicinal preparation.

The term "antibiotics" as used herein refers to a type of antimicrobial used in the treatment and prevention of bacterial infection. Some antibiotics can either kill or inhibit the growth of bacteria. Others can be effective against fungi and protozoans. The term "antibiotics" can be used to refer to any substance used against microbes. Antibiotics are commonly classified based on their mechanism of action, chemical structure, or spectrum of activity. Most antibiotics target bacterial functions or growth processes. Antibiotics having bactericidal activities target the bacterial cell wall, such as penicillins and cephalosporins, or target the cell membrane, such as polymyxins, or interfere with essential bacterial enzymes, such as rifamycins, lipiarmycins, quinolones and sulfonamides. Antibiotics having bacteriostatic properties target protein synthesis, such as macrolides, lincosamides and tetracyclines. Antibiotics can be further categorized based on their target specificity. "Narrow-spectrum" antibacterial antibiotics target specific types of bacteria, such as Gram-negative or Gram-positive bacteria. "Broad-spectrum" antibiotics affect a wide range of bacteria.

In some embodiments suitable antibiotics that can be used in the antimicrobial in combination with Fe chelators include ampicillin, kanamycin, ofloxacin, Aminoglycosides, Carbapenems, Ceftazidime, Cefepime, Ceftobiprole, Fluoroquinolones, Piperacillin, Ticarcillin, tobramycin, aztreonam, coliston, tazobactam, and others (or combinations of these antibiotics) that can be readily recognized by a person skilled in the art.

In some embodiments, suitable antibiotics that possess antibiotic effective against pathogen *Pseudomonas aeruginosa* include Aminoglycosides, Carbapenems, Ceftazidime, Cefepime, Ceftobiprole, Fluoroquinolones, Piperacillin, Ticarcillin, tobramycin, aztreonam, coliston, and others (alone or in combination) that can be readily recognized by a skilled person.

As disclosed herein, the antimicrobial agents herein described can be provided as a part of systems to perform any methods, including any of the assays described herein. The systems can be provided in the form of arrays or kits of parts. An array, sometimes referred to as a "microarray", can include any one, two or three dimensional arrangement of addressable regions bearing a particular molecule associated to that region. Usually, the characteristic feature size is micrometers.

In a kit of parts, the antimicrobial agent, candidate agents and other reagents to perform the method can be comprised in the kit independently. The antimicrobial agent can be included in one or more compositions, and each capture agent can be in a composition together with a suitable vehicle.

Additional components can include labeled molecules and in particular, labeled polynucleotides, labeled antibodies, labels, microfluidic chip, reference standards, and additional components identifiable by a skilled person upon reading of the present disclosure. The terms "label" and "labeled molecule" as used herein as a component of a complex or molecule referring to a molecule capable of detection, including but not limited to radioactive isotopes, fluorophores, chemiluminescent dyes, chromophores, enzymes, enzymes substrates, enzyme cofactors, enzyme inhibitors, dyes, metal ions, nanoparticles, metal sols, ligands (such as biotin, avidin, streptavidin or haptens) and the like. The term "fluorophore" refers to a substance or a portion thereof which is capable of exhibiting fluorescence in a detectable image. As a consequence, the wording "labeling signal" as used herein indicates the signal emitted from the label that allows detection of the label, including but not limited to radioactivity, fluorescence, chemiluminescence, production of a compound in outcome of an enzymatic reaction and the like.

In some embodiments, detection of a viable bacteria can be carried either via fluorescent based readouts, in which the labeled antibody is labeled with fluorophore, which includes, but not exhaustively, small molecular dyes, protein chromophores, quantum dots, and gold nanoparticles. Additional techniques are identifiable by a skilled person upon reading of the present disclosure and will not be further discussed in detail.

In particular, the components of the kit can be provided, with suitable instructions and other necessary reagents, in order to perform the methods here described. The kit will normally contain the compositions in separate containers. Instructions, for example written or audio instructions, on paper or electronic support such as tapes or CD-ROMs, for carrying out the assay, will usually be included in the kit. The kit can also contain, depending on the particular method used, other packaged reagents and materials (i.e. wash buffers and the like).

In some embodiments, the antimicrobial agents herein described can be included in pharmaceutical compositions together with an excipient or diluent. In particular, in some embodiments, disclosed are pharmaceutical compositions which contain at least one multi-ligand capture agent as herein described, in combination with one or more compatible and pharmaceutically acceptable vehicles, and in particular with pharmaceutically acceptable diluents or excipients. In those pharmaceutical compositions the multi-ligand capture agent can be administered as an active ingredient for treatment or prevention of a condition in an individual.

Further advantages and characteristics of the present disclosure will become more apparent hereinafter from the following detailed disclosure by way or illustration only with reference to an experimental section.

EXAMPLES

The methods and systems and related compounds and compositions herein disclosed are further illustrated in the following examples, which are provided by way of illustration and are not intended to be limiting.

In particular, the following examples illustrate exemplary combined administration of Fe(II) and F(III) chelators and related methods and systems according to the present disclosure. Reference is made in this connection to the data and experimentations described in the paper from Ryan C. Hunter, Fadi Asfour, Jozef Dingemans, Brenda L. Osuna, Tahoura Samad, Anne Malfroot, Pierre Cornelis, and Dianne K. Newman in mBio July/August 2013 Volume 4 Issue 4 e00557-13 [16] and related supporting information incorporated herein by reference in their entirety. A person skilled in the art will appreciate the applicability and the necessary modifications to adapt the features described in detail in the present section, to additional solutions, methods and systems according to embodiments of the present disclosure.

The following materials and methods were used in performing the experiments illustrated in the examples herein described.

Chemicals.

Substantially iron-free conalbumin, 1, 10-phenanthroline, hydroxylamine hydrochloride, ammonium acetate, ferrous ammonium sulfate, and carrier DNA for yeast transformation were purchased from Sigma-Aldrich. All enzymes used for DNA manipulation were purchased from New England Biolabs.

Biofilm Experiments.

A flow cell system was constructed for biofilm experiments in Examples 1-4. The size of each flow channel was 1.5×4×34 mm; continuous flow of 1% TSB-based biofilm medium (with or without the respective additives detailed in the Results section) at the rate of 3 ml/h was supplied with a Watson-Marlow peristaltic pump; the temperature for biofilm growth was 22° C. An early stationary phase culture grown in 10% TSB was diluted to an $OD_{500}$ of 0.1 in biofilm control medium (1% TSB). Each flow cell was then inoculated with 300 μl of the diluted culture by injection with a 1 ml syringe. In order to allow cells to attach to the glass surface, the flow was arrested for 1.5 hours and then resumed throughout the length of each experiment (up to 6 days). To image biofilms, confocal laser scanning microscopy (CLSM) with a Leica TCS SPE inverted microscope was used. To assure images used for comparisons of biofilm formation were representative and reproducible, multiple fields of view were acquired over time with a 10× dry objective in each flow cell within a single experimental set, and at least 4 independent experimental sets were performed. Fluorescence and DIC images were processed using Bitplane Imaris and NIH imageJ software. In most cases, fluorescence-based multiple biofilm image stacks (spaced 1-2 μm apart) were analyzed using the autoCOMSTAT software, a modified version of the COMSTAT biofilm evaluation package by Heydorn [10] et al. [17, 18]. For each image a global threshold was calculated using the Robust Automated Threshold Selection algorithm with a critical-size setting of 20 μm, and connected-volume filtering was performed with a connectivity setting of 18 to remove free-floating biomass. Substratum coverage calculations were based on the first 3 μm above the substratum. The area of each analyzed image was $3.03 \times 10^5$ μm$^2$ and results from measurements of 1-6 images for each strain and treatment were averaged and sample standard deviations were calculated. The biofilm parameters reported here are biovolume per image area (referred to as biomass), substratum coverage, maximum height, and average height of the biomass, which excludes any area not covered by cells.

Cell-Surface Attachment.

Attachment was analyzed using phase contrast imaging on a Leica confocal microscope. Stationary-phase cultures were diluted 1:50 in 10% LB and 0.5 ml of this suspension were pipetted into a sterile chambered system (Lab-Tek, Rochester N.Y.) with a borosilicate cover glass bottom. After 0.5 h or 4 h incubation at 22° C., unattached cells were discarded by gently replacing the supernatant with fresh medium, and attached cells were counted. Six fields of view for each strain and condition were analyzed and the percent of the surface covered by attached cells was estimated using Adobe Photoshop.

Motility Assays.

Swimming, swarming and twitching motilities were determined as previously described [19].

Flow cell biofilms were grown under constant flow at 22° C. in 1.5×4×34 mm flow cells. Continuous flow of 10% LB was supplied with a peristaltic pump at a constant rate of 3 ml h$^{-1}$. An early stationary-phase culture was diluted to an optical density at 500 nm of around 0.1 and 300 μl were inoculated into the flow cell. Strains expressing eyfp constitutively were used to visualize the biofilms. Upon inoculation, cells were allowed to attach in the absence of flow for 1.5 h before flow was resumed. Developing biofilms were imaged in 3 dimensions using a Leica confocal microscope. eYFP was excited with a 488 nm laser beam kept at constant intensity throughout the experiment, and emission from 510 to 618 nm was collected. Routinely, the Applicant observed that the distribution of bacterial cells throughout the colonized surface varied depending on the region of the flow cell, probably due to factors such as flow or accumulation of planktonic cells. To assure reproducibility, all images were acquired from an area set in the middle of the flow cell. Three images of duplicate flow cell lines were recorded and at least two independent experiments were performed.

Colony biofilms were grown on agar containing 1% tryptone as previously described [20]. Three colonies from independent spottings were documented for 8 days using an Epson scanner.

Relative Quantification of Dissolved Oxygen in Batch Cultures.

Oxygen was measured in batch fermentor cultures using a Clark electrode [21]. The electrode was calibrated such that the reading obtained by the computer without the probe attached was equal to zero, while the initial reading for the uninoculated medium (after aeration and agitation for 12 hours) was set to 100 percent.

Study Design and Sample Collection.

Twenty-five participants (aged 7 to 20) and eight participants (aged 16 to 38) were recruited from Children's Hospital Los Angeles (CHLA) and the Academic Hospital UZ Brussel, respectively. Inclusion criteria were a positive diagnosis of CF, ability to expectorate sputum and informed consent. Sputum was flash frozen in liquid nitrogen shortly after expectoration to minimize oxidation and/or mRNA degradation and stored at −80° C. until processing. Disease severity was determined by FEV1% scores and patients were clustered using published guidelines [22] [23]. This study was approved by the ethical commissions of the California Institute of Technology, Children's Hospital Los Angeles, and the Academic Hospital UZ Brussel.

Sputum Collection.

In experiments herein described, sputum was obtained by expectoration and was immediately flash frozen in liquid nitrogen to minimize oxidation.

Sputum Processing.

In Examples 1-4, frozen sputum samples were allowed to thaw in an anaerobic chamber. Sputum was disrupted using a syringe and was further homogenized by vortexing in an equal volume of anaerobic 50 mM HEPES buffer. Sputum was centrifuged at 8,000×g for 10 min and supernatants were filtered through 0.22 μM columns for 20 minutes at 10,000×g. Filtrates were analyzed (anaerobically) for iron content. When sufficient material was obtained, 200 μL of filtrate was stored at −80° C. for ICP-MS analysis. In Examples 5 to 11 Sputum Processing. Frozen samples were thawed in an anaerobic chamber. Sputum was disrupted using a 16-gauge needle and was homogenized by vortexing in an equal volume of anoxic 50 mM 4-(2-hydroxyethyl)-1-piperazineethanesulfonic acid (HEPES) buffer. Sputum was centrifuged at 8,000×g for 10 min and supernatants were filtered through 0.22 μm pore-size columns for 20 minutes at 10,000×g. Filtrates were analyzed for iron content. When sufficient sputum material was obtained, 200 μL of filtrate was stored at −80° C. for ICP-MS analysis.

MBEC Assay for Biofilm Prevention and Dissolution.

In Examples 1 to 4, biofilm prevention and dissolution were measured via a high-throughput biofilm assay (MBEC Physiology and Genetics Assay) consisting of a 96-well plate into which a 96-peg plastic lid fits. This lid also fits over a standard 96-well plate, which was subsequently used to test the efficacy of iron chelators. Inoculum was prepared by diluting (30-fold) a 1.0 McFarland suspension of $P.$ $aeruginosa$ PA14 in TSB. 150 μL was dispensed into each of the 60 inner wells, while 200 μL of sterile trypticase soy broth (TSB) was placed in each perimeter well. For dissolution experiments, plates were incubated at 37° C. for 24 h, and were transferred to an anaerobic chamber for 24 h at 37° C. in anaerobic TSB containing 50 mM $KNO_3$. Biofilms were then exposed to conalbumin and/or FerroZine® for 24 h. Each treatment was complemented with the addition of 80 μM ferrous ammonium sulfate. After treatment, lids were rinsed once in 50 mM HEPES, air dried for 10 min and quantified by crystal violet staining [24]. For biofilm prevention, anaerobic inoculum was amended with conalbumin and/or FerroZine®. Media was replaced every 24 h by transferring the MBEC lid to a sterile plate containing growth media+/−treatments, and biofilms were allowed to develop for 168 h. Biomass was quantified as described above. Biological triplicates and six technical replicates (n=18) were used for each treatment.

Iron Quantification.

In Examples 1-4, ferrous iron and total iron were quantified using the FerroZine® assay [21]. Briefly, 50 μL of sputum filtrate was added to 504 of 1M HCl to quantify Fe(II). For total iron, 504 was treated with 504 of 10% hydroxylamine hydrochloride in 1M HCl to reduce Fe(III) to Fe(II). Samples were added to 1004 of FerroZine® (0.1% w/v in 50% ammonium acetate), incubated for 15 min, and absorbance was measured spectrophotometrically at 562 nm. Ferrous ammonium sulfate was used as the iron standard. FerroZine® was also used to determine the Fe(II) composition of the trypticase soy broth (TSB) growth medium. In Examples 1 to 4, samples were also analyzed by inductively coupled plasma mass spectrometry (ICP-MS), a highly sensitive mass spectrometry method capable of metal determination below one part per trillion. Briefly, 50 µL of filtrate was digested in 100 µL 8N nitric acid, and brought to a total of 1.5 mL in 5% nitric acid/indium standard. Samples were analyzed on an Agilent 7500 cx equipped with a reaction cell, using He (2 mL/min) and H2 (2.5 mL/min) as reaction gases. Fe concentrations were calculated using $^{56}$Fe and $^{57}$Fe signal intensities. In Examples 5 to 12 Iron levels were quantified using the FerroZine® assay (300). Briefly, 50 µL of sputum filtrate was carefully added (to avoid introducing bubbles) to 50 µL of 1 M HCl to quantify Fe(II). For total iron, 50 µL was treated with 50 µL of 10% hydroxylamine hydrochloride in 1 M HCl to reduce Fe(III) to Fe(II). Samples were added to 100 µL of FerroZine® (0.1% w/v in 50% ammonium acetate), incubated for 15 min, and absorbance was measured at 562 nm. Ferrous ammonium sulfate was used as the iron standard. Samples were also analyzed by inductively coupled plasma mass spectrometry (ICP-MS). Briefly, 50 µL of filtrate was digested in 100 µL 8 N nitric acid, and brought to a total of 1.5 mL in 5% nitric acid/indium standard. Samples were analyzed on an Agilent 7500 cx equipped with a reaction cell, using He (2 mL/min) and H$_2$ (2.5 mL/min) as reaction gases. Fe concentrations were calculated using $^{56}$Fe and $^{57}$Fe signal intensities.

ICP-MS Versus FerroZine® Determination of Total Iron.

Figure 2:
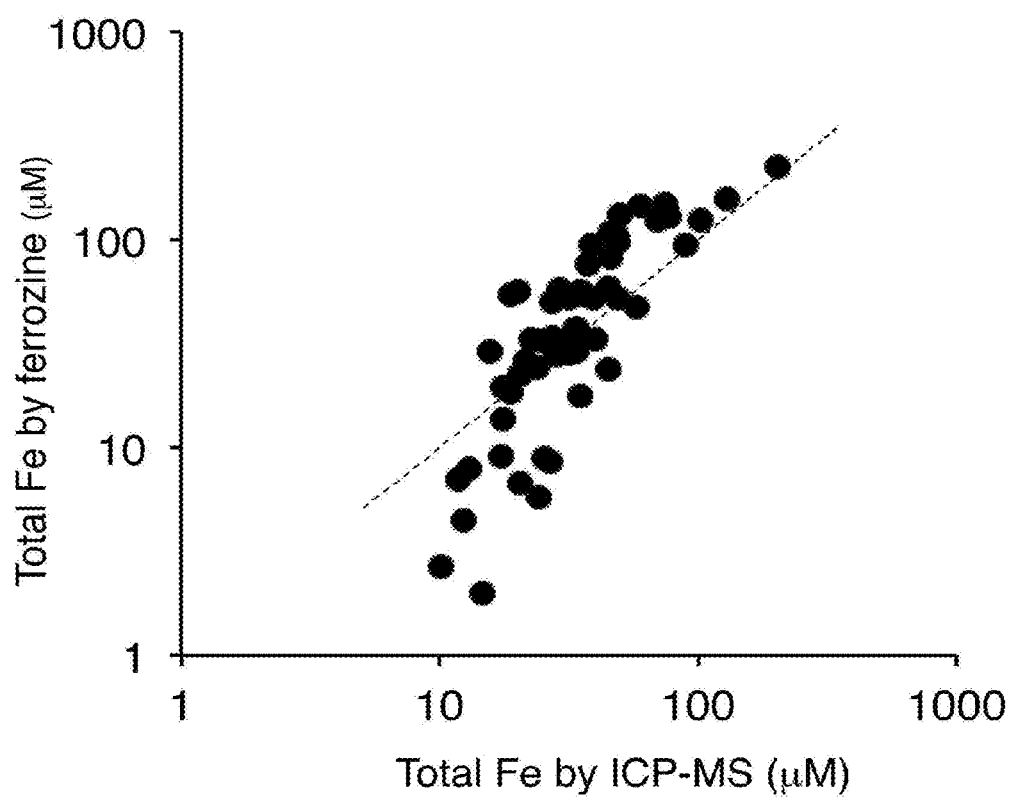
FIG. 2 shows a diagram illustrating results of a determination of total sputum iron using ICP-MS versus 3-(2-Pyridyl)-5,6-diphenyl-1,2,4-triazine-p,p'-disulfonic acid monosodium salt hydrate, which is also known under the trademark FerroZine®. The latter approach generally estimates ~30% more total iron than the more sensitive mass spectrometry method. Dashed line represents the 1:1 trendline.

In Examples 1 to 4, as the accuracy and precision of the FerroZine® assay might be compromised as the proportion of Fe(II) increases, leading to overestimations of total iron concentrations [25] to control for this, total sputum iron was quantified using inductively coupled plasma mass spectrometry (ICP-MS). As expected, comparison of the two methods revealed a higher estimate of total iron using the colorimetric approach (FIG. 2). On average, FerroZine® measurements were 30% greater than those obtained using ICP-MS, indicating that Fe(II) levels determined here were higher than those present in sputum. For this reason, a 30% reduction was applied to all reported ferrous iron sputum concentrations in the experiments of Examples 3-4. Despite this conservative reduction, sputum Fe(II) levels are frequently greater than those used in our chelation experiments (~10 µM), which were sufficient to impede Fe(III)-chelation treatment.

Sputum mRNA Extraction and Quantitative Real-Time PCR.

Sputum samples were collected, frozen, and homogenized as described above. Under anoxic conditions, homogenate was added to one volume of 0.1 mm zirconia beads and three volumes of Trizol LS, and mRNA was extracted as described by Lim et al. [26]. Purity and degradation was assessed using Nanodrop spectrophotometry, agarose gel electrophoresis and by an Agilent 2100 Bioanalyzer. cDNA was reverse transcribed from 1 µg of total RNA with the First-strand cDNA Synthesis Kit (Amersham Biosciences) or iScript (Bio-Rad) according to manufacturer protocols. cDNA was then used as a template for quantitative PCR (RealTime 7500 PCR machine; Applied Biosystems) using SYBR green with the ROX detection system (Bio-Rad). Triplicate measurements were made on each sputum sample. As controls, anaerobically-grown P. aeruginosa PA14 treated with 50 µM Fe(II), 50 µM Fe(III), or water (no iron) were assayed as previously described [27]. The primer sets are reported in Table 1 below.

TABLE 1

Oligonucleotide primers qRT-PCR oligonucleotide primers

| Target Gene | Primer | Sequence (5'-3') | SEQ ID NO | Primer Efficiency % | R$^2$ |
|---|---|---|---|---|---|
| clpX | clpX F | CCTGTGCAATGACATCATCC | 1 | | |
| | clpX R | TTCTTGTCACGCTGGTTGAG | 2 | | |
| oprI | oprI F | AGCAGCCACTCCAAAGAAAC | 3 | 99 | 0.999 |
| | opri R | CAGAGCTTCGTCAGCCTTG | 4 | | |
| bqsS | bqsS F | GAGCTGGAAAAGGACACCTG | 5 | 100 | 0.994 |
| | bqsS R | TTTCCAGGATCGGCGTATAG | 6 | | |
| bqsR | bqsR F | AGCCCTACGACCTGATCATT | 7 | 60 | 0.974 |
| | bqsR R | CGGCTTGGTCAGATAGTCGT | 8 | | |
| pvdA | pvdA F | CACAGCCAGTACCTGGAACA | 9 | 99 | 0.995 |
| | pvdA R | GGGTAGCTGTCGTTGAGGTC | 10 | | |
| fptA | fptA F | GGACCGCGACTACTTCTACG | 11 | 97 | 0.986 |
| | fptA R | TCGAGTCGATGTGCTGGTAT | 12 | | |
| feoA | feoA F | AACCGTCCCGTTCCTACC | 13 | 107 | 0.997 |
| | feoA R | CAGAAGCCCCATGGAGAA | 14 | | |
| feoB | feoB F | GAGCGGCTGATTACCATCAT | 15 | 90 | 0.996 |
| | feoB R | CGAGCAGGTACAGGGAGAAG | 16 | | |
| hasAp | hasAp F | AAGGTGGTCTACGGCCTGAT | 17 | 87 | 0.989 |
| | hasAp R | ACTGGTCGAAGGTGGAGTTG | 18 | | |

TABLE 1-continued

Oligonucleotide primers

Oligonucleotide primers for in vitro mRNA synthesis

| Target Gene | Primer | Sequence (5'-3')[a] | SEQ ID NO |
|---|---|---|---|
| clpX | clpXinvitroF | TAATACGACTCACTATAGGGAGATGCTGTATTGCTCCTTCTGC | 19 |
|  | clpXinvitroR | CGGGAAATCTTGTCGATCTC | 20 |
| bqsS | bqsSinvitroF | TAATACGACTCACTATAGGGAGAATGCAACTGGACGAGCAAC | 21 |
|  | bqsSinvitroR | GAACGCTTCAGGGTCTCCTC | 22 |
| bqsR | bqsRinvitroF | TAATACGACTCACTATAGGGAGAGCTGGTTGAGGATCACGTTC | 23 |
|  | bqsRinvitroR | GACCTCGATGACGTTGGAAT | 24 |

[a]underlined sequence represents T7 promoter region

For all primer sets (Table 1) the following cycling parameters were used: 94° C. for 3 min followed by 40 cycles of 94° C. for 60 s, 55° C. for 45 s, and 72° C. for 60 s, followed by 72° C. for 7 min. oprI and clpX were used to normalize levels of gene expression [28, 29] (see also FIG. 1 and procedure for validation of mRNA extraction and analysis). Primer efficiencies were determined using iQ™S Optical System Software (BioRad), and standard curves were constructed based on four different known quantities of genomic DNA of *P. aeruginosa* PAO1 (100 ng, 50 ng, 10 ng, and 5 ng) (Table 1). The threshold cycle (Ct) values of each gene were used to calculate relative gene expression using the $2^{-\Delta\Delta Ct}$ method [24]. The mRNA extraction protocol precluded a concurrent Fe(II) measurement because the coloration of the Trizol reagent interferes with the FerroZine® assay.

mRNA Recovery from Sputum.

Experiments were performed to determine whether the degradation of mRNA in sputum or via the extraction protocol would influence the quantification of bqsR and bqsS relative to the housekeeping gene, clpX (clpX was chosen as the length of oprI is not optimal for in vitro mRNA synthesis). To test this, we in vitro synthesized mRNA by amplifying a fragment of each gene using an invitroF primer with a 5' T7 promoter and an invitroR primer (Table 1). The PCR product was cleaned with ExoSAP-IT, and 2 μL of the product was in vitro transcribed using the Megascript T7 Kit. In addition to the reaction mixture, we added 2 μL recombinant RNasin Ribonuclease Inhibitor (Promega, Madison, Wis.). The RNA product was treated with 2 μL Turbo DNase for one hour to remove any DNA template and was further purified using the Megaclear Kit (Ambion, Foster City, Calif.) to remove unincorporated reaction components. The quantity of each transcript was determined by Nanodrop spectrophotometry. Assuming the average mass of a ribonucleotide to be 321 Da, the concentration of each transcript was converted to copy numbers/4, diluted to $2 \times 10^{12}$ copies/μL and stored at −80° C. $10 \times 10^{12}$ copies of each mRNA transcript were then spiked into six 500 μL sputum samples (from a *P. aeruginosa*-negative patient), immediately homogenized and resuspended in 750 μL of the Trizol reagent. As a control, mRNA was also spiked into Trizol alone to account for degradation as a result of our extraction protocol. mRNA was then extracted and quantified by qRT-PCR using the methods described in the main text. Ratios of bqsR and bqsS to clpX were used to determine potential mRNA degradation biases (see also FIG. 1 and validation of mRNA extraction and analysis procedures).

Validation of mRNA Extraction and Analysis.

Verification of RNA extraction and related analysis was performed by non denaturing agarose gel analysis of the mRNA extract from sputum related to a heat-degraded (95° C. for 20 min) bacterial mRNA control and the results reported in FIG. 1A. To confirm the related results Agilent 2100 Bioanalyzer electropherogram of a sputum mRNA extracts was performed and a representative result is shown in FIG. 1B. The large peaks represent abundance of low molecular weight species, 5S and 5.8S rRNA, tRNA and degradation products. The presence of other distinct peaks represents a mix of rRNA, intact mRNA and degradation products. Validation of clpX and oprI as reference genes for qRT-PCR in CF sputum was performed and the results reported in FIG. 1C. OprI is one of the most highly produced proteins in *P. aeruginosa* and is constitutively expressed. ClpX is a constitutively expressed ATP-binding subunit of serine protease. Both genes showed consistent transcriptional activity relative to one another ($R^2 = 0.87$), validating their use as reference genes in our sputum analysis. Also Trizol/glass bead extraction method in vitro was performed for synthesized mRNA recovery from sputum and Trizol. The results are illustrated in FIG. 1D. The method did not result in any significant differences in ratios of our target genes. In vitro transcripts introduced to sputum samples showed a 10-fold lower ratio for bqsS. While this is an imperfect experiment because it introduces mRNA directly into sputum (which likely degrades more rapidly than it would within a cellular context) it allowed experimentally assessing the potential for different degradation rates of bqsR and bqsS transcripts. Significant differences were observed in bqsS stability compared to clpX (indicating its abundance in sputum may be underestimated 10-fold); bqsR, in contrast, was as stable as clpX. It is noted that these data likely present a "worst-case" scenario because mRNA degradation is likely to be faster outside of the cell. Nevertheless, the values reported in Example 9 (expression of bqsS and bqsR relative to oprI, which is constant relative to clpX) are still consistent with a bioavailable Fe(II) pool: if anything, the values reported for bqsS underestimate its abundance.

HPLC Quantification of Phenazines.

Phenazine extraction and quantification was performed anaerobically as previously described [30]. 97 out of 115 samples contained sufficient sputum material for phenazine analysis [31].

MBEC Assay for Biofilm Prevention and Dissolution.

a high-throughput biofilm assay was used (MBEC Physiology and Genetics Assay) consisting of a 96-well plate and 96-peg lid. Inoculum was prepared by diluting (30-fold) a $10^7$ cell/ml suspension of *P. aeruginosa* PA14 in Trypticase Soy Broth (TSB). 150 µL was dispensed into each of the 60 inner wells, while 200 of sterile TSB was placed in each perimeter well. For dissolution experiments, plates were incubated at 37° C. for 24 h, and lids were transferred to a fresh 96-well TSB plate for 24 h at 37° C. or to an anaerobic chamber for 24 h at 37° C. in anaerobic TSB containing 50 mM $KNO_3$. Biofilms were exposed to 100 µM conalbumin and/or 200 µM FerroZine® for 24 h (concentrations were selected such that they were in molar excess of media iron concentrations). The dual chelator treatment was also complemented with 8 µg/mL tobramycin or 80 µM ferrous ammonium sulfate where indicated. After treatment, lids were rinsed once in 50 mM HEPES, air dried for 10 min and quantified by crystal violet staining [24]. For biofilm growth prevention assays, both aerobic and anaerobic inocula were amended with 100 µM conalbumin and/or 200 µM FerroZine®. For aerobic experiments, biofilms developed for 24 h. For anaerobic growth, the medium was replaced every 24 h by transferring the lid to a sterile plate containing TSB+/− treatments, and biofilms were developed for 168 h.

Statistical Analysis.

Figure 3:
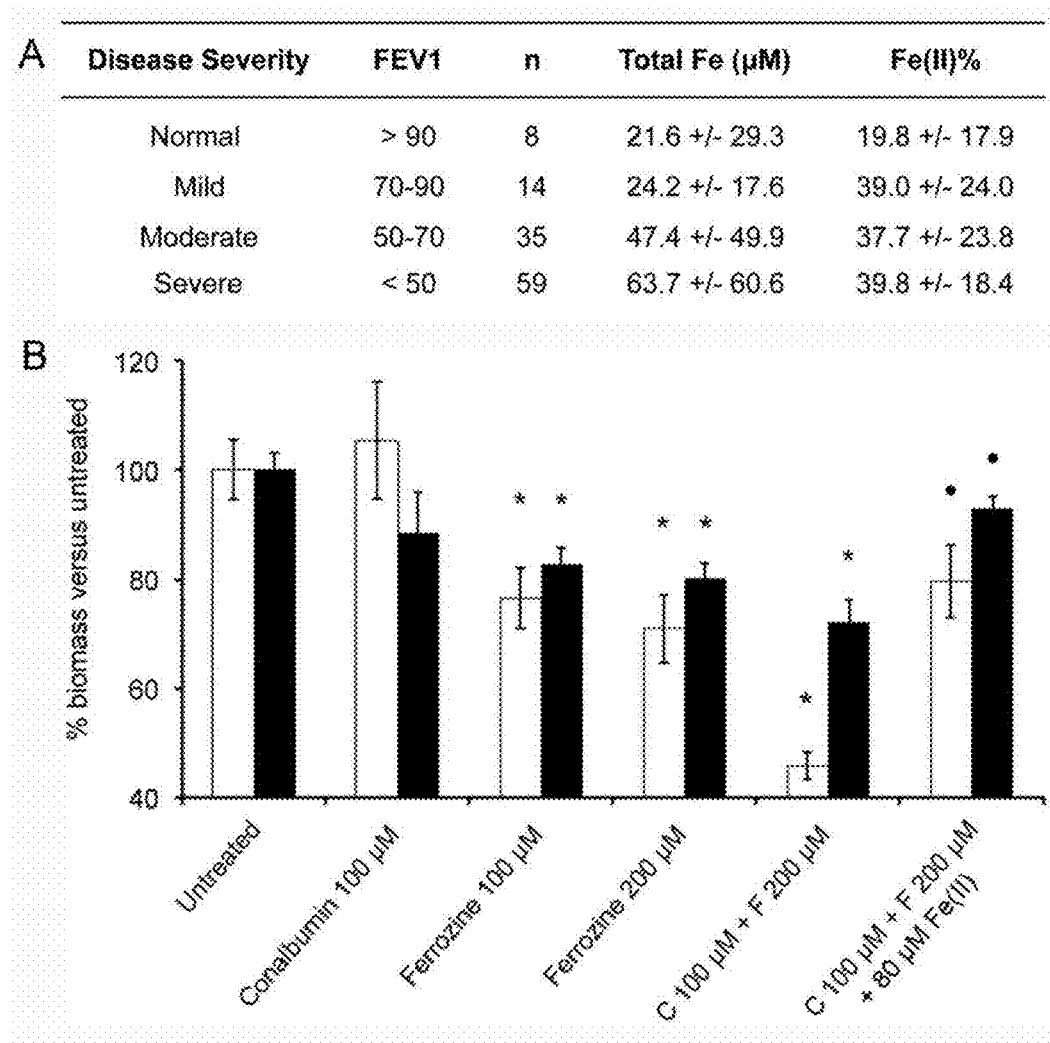
FIG. 3 shows a table and a diagram illustrating the results of experiments where Fe(II) chelators and Fe(III) chelator are administered in combination. In particular.

In Examples 1-4, two-tailed student t-tests were used for pair-wise comparisons between patients groups (FIG. 3A) and chelator treatments relative to untreated controls (FIG. 3A). Pairwise comparisons were also performed between chelator treatments and those complemented with 80 µM Fe(II). In all cases, P<0.05 was considered statistically significant. In Example 6 Spearman rank analysis (ρ) was performed on iron and phenazine concentrations versus lung function. In Example 10, two-tailed student t-tests were used for pair-wise comparisons between chelator treatments and controls. In all cases, p<0.05 was considered statistically significant

Example 1: Fe(II)/Fe(III) Combination Therapy for Cystic Fibrosis Patients

The abundance of Fe(II) in the lungs of cystic fibrosis patients has important implications for the design of novel antimicrobial therapies.

Competition between pathogens and their hosts for ferric iron [Fe(III)] has been extensively studied due to iron's critical importance in pathogenesis [3]. While microbial ferrous iron [Fe(II)] uptake pathways are known [4], therapeutic strategies designed to limit iron availability have only targeted Fe(III) because it is commonly assumed to be the dominant physiologically relevant form.

For example, Fe(III) chelation has been shown to dramatically improve antibiotic effectiveness against the opportunistic pathogen *Pseudomonas aeruginosa* in aerobic environments, and is being explored as a means to combat biofilm infections of cystic fibrosis (CF) patients [9], [8], [10], [11]. Based on the results obtained by this approach in vitro, it is expected that if it is to be similarly effective in vivo, iron would need to remain in its oxidized state [Fe(III)] as infections progress.

However, in late stages of CF infections, localized hypoxic microenvironments exist [12] which could stabilize Fe(II). Furthermore, *P. aeruginosa* produces redox-active phenazines in CF sputum [13] that can reduce Fe(III) to Fe(II) and circumvent Fe(III)-chelation in vitro[10].

Ferric iron [Fe(III)] chelation has been shown to combat pathogenic microbial biofilms in vitro, and has been proposed as a novel treatment for cystic fibrosis (CF) patients. However, the success of this approach assumes an abundance of Fe(III) in the infected environment. Here Applicants show that appreciable levels of ferrous iron [Fe(II)] exist in the majority of CF lungs, that Fe(II) compromises Fe(III) chelation therapy under anaerobic conditions, and that Fe(III) and Fe(II) chelators can act synergistically to prevent or disrupt biofilm growth.

In particular, Examples 2-4 (below) show that Fe(II) can be abundant at infection sites, and its concentration was measured in CF sputum from patients at different stages of lung function decline. While total iron has been quantified previously [18], this is the first report of its oxidation state in vivo.

Example 2: Demonstration of the Presence of Fe(II) in Sputum of Cystic Fibrosis Patients Twenty-five participants with cystic fibrosis (CF), aged 7 to 20, were recruited during scheduled visits to Children's Hospital Los Angeles (CHLA). Study inclusion criteria were a positive diagnosis of CF, ability to expectorate sputum and informed consent/assent. Disease severity was determined by FEV1% scores using published guidelines [20]. CHLA and the California Institute of Technology approved the study protocols (CCI-10-00232).

A total of 116 sputum samples from 25 patients were immediately flash frozen upon expectoration and moved to an anaerobic chamber for analysis. Samples were homogenized and ratios of Fe(II)/Fe(III) concentrations were determined using the FerroZine® assay. Total iron levels were confirmed using ICP-MS and increased significantly as lung function worsened (FIG. 3A). In most patients, a notable proportion of total iron was Fe(II) (>19%), though it was appreciably higher (>37%) in subjects with mild to severe pulmonary obstruction.

That such high concentrations of Fe(II) are observed at all stages of infection is striking, and reinforces the need to better understand the mechanisms of iron homeostasis in the lung environment [19].

Example 3: Demonstration of Synergistic Effect of Fe(II) and Fe(III) Chelators on Bacterial Biofilms Because the abundance of Fe(II) in infected environments of lungs of CF patients may compromise the success of Fe(III)-specific chelation therapies, the question of whether a combination of Fe(III) and Fe(II) chelators would be more effective than Fe(III) chelators alone was investigated. An anaerobic, high-throughput biofilm assay was used to determine whether FerroZine®, an Fe(II)-specific chelator, could act synergistically with conalbumin, an Fe(III) chelator, to prevent *P. aeruginosa* biofilm formation (FIG. 3B).

Neither compound affected planktonic growth rates. Contrary to aerobic observations [9], [8], 100 µM conalbumin was also ineffective in preventing biofilm growth under anaerobic conditions where ~10 µM Fe(II) and 10 µM Fe(III) were present. In contrast, 100 µM FerroZine® reduced biofilm accumulation by 24% and 200 µM FerroZine® reduced it slightly further. Strikingly, the combination of 100 µM conalbumin and 200 µM FerroZine® reduced biofilm accumulation by 54%. To determine whether this effect was due to iron sequestration rather than non-specific interactions, Fe(II) in excess of the chelation capacity was added. Under these conditions, biofilm growth was restored. Iron not only signals biofilm formation, but is involved in biofilm maintenance [11].

Example 4: Demonstration of Synergistic Effect of Fe(II) and Fe(III) Chelators on Mature Bacterial Biofilms Because iron not only signals biofilm formation, but is involved in biofilm maintenance [11], similar mixed Fe(II)/Fe(III) chelation experiments targeting mature biofilms (FIG. 3B) were performed.

Conalbumin did not significantly reduce established biomass, but ~20% dissolution was observed in the presence of 100 or 200 µM FerroZine®. Together with conalbumin, FerroZine® promoted even more dissolution, yet biomass was maintained at high levels in the presence of excess Fe(II). Collectively, the results of examples 1-4 indicate that as lung function declines and Fe(II) concentrations rise, targeting both oxidation states will be more effective than targeting Fe(III) alone.

Example 5: Total and Ferrous Iron Concentrations Increase within the Lung Environment as Infections Progress Although the total concentration of iron has been measured in the airways [32] [33] and is known to accumulate in the lavage and explanted lungs of CF patients [34], its oxidation state has not been defined. Experiments were therefore set out to measure Fe (II) abundance in CF sputum at different stages of disease progression. Accurately measuring the iron oxidation state is complicated by the rapid oxidation of Fe (II) to Fe (III) once expectorated sputum is exposed to ambient oxygen. With this in mind, a sputum collection and processing approach has been designed to better preserve and measure iron in its in vivo oxidation state.

Twenty-four pediatric patients from across the spectrum of disease severity provided 115 sputum samples that were rapidly flash frozen upon expectoration. Samples were then moved to an anaerobic chamber to impede oxidation, mechanically homogenized by syringe, and ratios of free Fe (II)/Fe (III) concentrations were then determined using the FerroZine® assay. As controls, total iron levels were also assayed using inductively-coupled plasma mass spectrometry and untreated samples stored under argon were compared to flash-frozen samples to test whether the iron oxidation state was faithfully preserved during cryo-storage.

Figure 4:
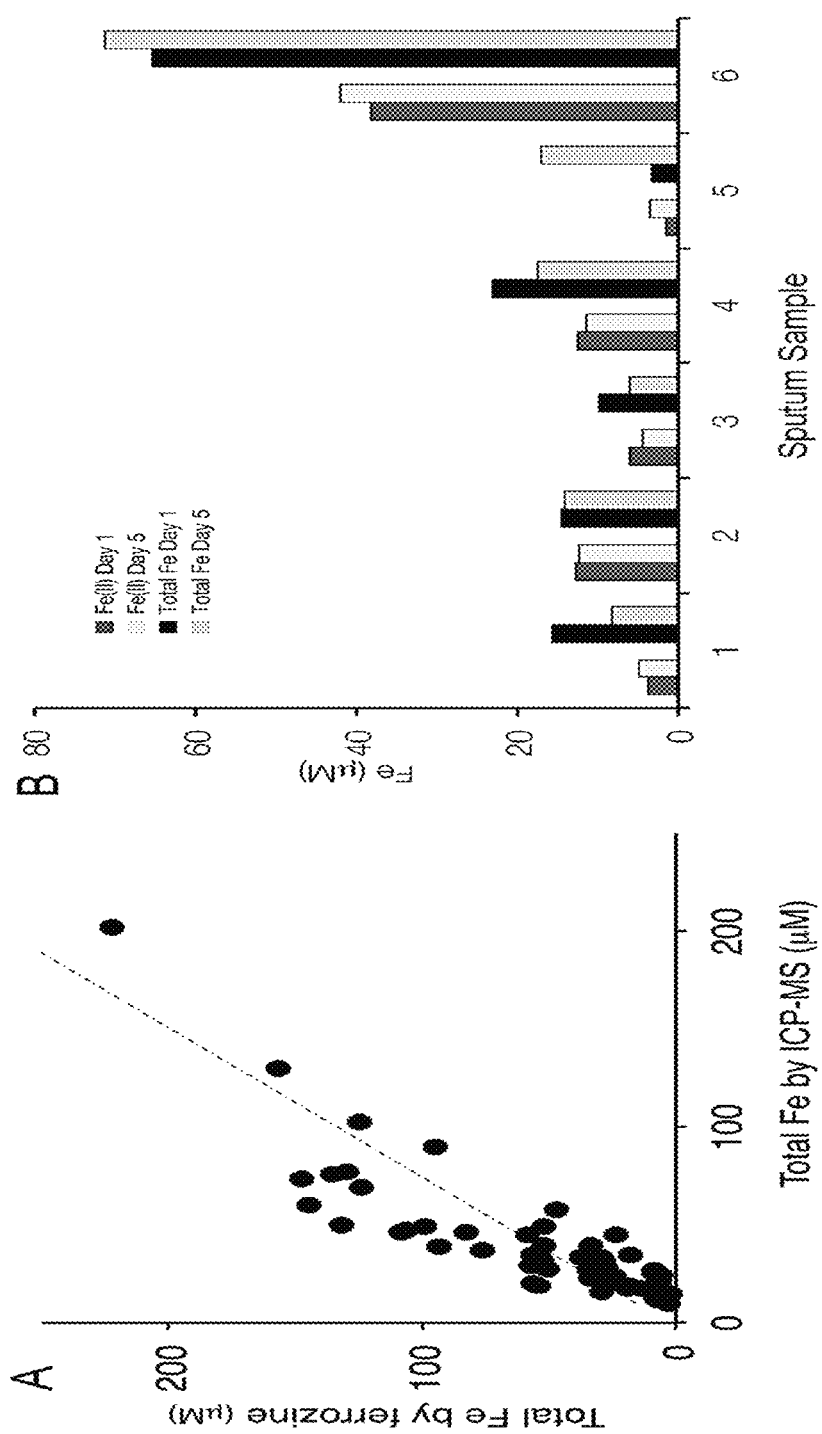
FIG. 4 shows diagrams illustrating iron detection in sputum samples. In particular.

In particular, to control accuracy and precision of the FerroZine® assay and avoiding obtaining compromised results as the proportion of Fe(II) increases [32], total sputum iron was also measured using ICP-MS, a highly sensitive mass spectrometry method capable of metal determination below one part per trillion. The results of the FerroZine® versus ICP-MS determination are illustrated in FIG. 4A.

Comparison of the two methods revealed a higher estimate of total iron using the colorimetric approach. On average, the FerroZine® reagent generally estimated ~30% more total iron than the more sensitive mass spectrometry method, indicating that Fe(II) levels determined here might be an over-estimate of those present in sputum. For this reason, a 30% reduction was applied to all reported ferrous iron sputum concentrations (FIG. 1, Table 1). Even after applying this conservative adjustment, sputum Fe(II) levels were frequently greater than those used in the chelation experiments (~10 µM), which are sufficient to impede Fe(III)-chelation treatment.

To verify the accuracy of the Fe(II) v. Fe (III) determination iron oxidation during sample storage was also measured. Six expectorated sputum samples were immediately stored under argon gas and moved to the anaerobic chamber within 4 hours of expectoration. Samples were mechanically homogenized by syringe, and an equal volume of 50 mM HEPES was added. Samples were split into two, one aliquot was removed from the chamber, immediately frozen in liquid nitrogen, and stored at −80° C. for 5 days. The anaerobic, unfrozen aliquot was subject to iron analysis as described in Materials and Methods (main text). Five days later, the frozen aliquot was returned to the anaerobic chamber where it was subject to the same analysis. Fe(II) and total iron were quantified and changes in iron chemistry were determined for the storage period. The results are illustrated in FIG. 4B which shows that on average for these six samples, the ferrous iron percentage of the total iron pool rose ~6% after storage.

Phenazine concentrations were also determined and the results of the detected concentrations of Fe(II) and Fe (III), detected phenazine concentration and lung function measured by forced expiratory volume, FEV1% are summarized in Table 2 below.

TABLE 2

Patient summary for iron and phenazine concentrations

| Patient | Sample ID | FEV1 % | Fe(II) (µM) | Total Fe | Fe(II) % | PYO (µM) | PCA (µM) | Total (µM) |
|---|---|---|---|---|---|---|---|---|
| 2 | 1/31/11 | 43 | 2.0 | 35.0 | 5.7 | 10.1 | 2.7 | 12.8 |
| 2 | 2/7/11 | 44 | 5.5 | 9.0 | 60.9 | 0 | 2.0 | 2.0 |
| 2 | 4/12/11 | 40 | 33.1 | 50.4 | 65.6 | 9.78 | 0.5 | 10.3 |
| 2 | 10/28/11 | 44 | 6.7 | 11.6 | 58.0 | | | |
| 3 | 1/31/11 | 66 | 40.0 | 133.2 | 30.0 | 18.9 | 19.6 | 38.5 |
| 3 | 3/28/11 | 62 | 0.6 | 8.6 | 7.3 | 9.6 | 8.9 | 18.5 |
| 3 | 5/24/11 | 57 | 7.1 | 19.7 | 35.8 | 2.0 | 1.4 | 3.4 |
| 3 | 7/8/11 | 63 | 8.5 | 33.5 | 25.4 | 14.6 | 3.4 | 18.0 |
| 3 | 7/12/11 | 68 | 21.0 | 26.5 | 79.2 | | | |
| 4 | 2/1/11 | 55 | 23.2 | 52.5 | 44.2 | 0 | 6.5 | 6.5 |
| 4 | 7/26/11 | 62 | 17.0 | 29.0 | 58.6 | | | |
| 5 | 2/1/11 | 52 | 48.8 | 60.5 | 80.7 | 19.7 | 6.5 | 26.2 |
| 5 | 7/19/11 | 45 | 169.0 | 370.0 | 45.7 | 8.8 | 9.0 | 17.8 |
| 5 | 9/12/11 | 38 | 26.1 | 38.8 | 67.3 | 2.8 | 7.6 | 10.4 |
| 5 | 11/28/11 | 51 | 146.0 | 186.9 | 78.1 | 3.6 | 9.4 | 13.0 |
| 6 | 2/1/11 | 32 | 6.1 | 15.1 | 40.5 | | | |
| 6 | 11/28/11 | 32 | 148.3 | 167.3 | 88.7 | 6.5 | 13.1 | 19.6 |
| 7 | 2/1/11 | 45 | 4.5 | 8.0 | 56.0 | 17.0 | 9.9 | 26.9 |
| 7 | 3/18/11 | 40 | 14.1 | 54.1 | 26.1 | 12.8 | 88.4 | 101.3 |
| 7 | 3/26/11 | 34 | 105.1 | 147.9 | 71.1 | 64.6 | 114.5 | 179.1 |
| 7 | 3/30/11 | 39 | 98.9 | 123.7 | 79.9 | 63.6 | 135.5 | 199.1 |
| 7 | 4/6/11 | 38 | 20.4 | 27.7 | 73.6 | 22.2 | 32.1 | 54.3 |
| 7 | 8/22/11 | 34 | 15.2 | 50.6 | 30.1 | 3.6 | 20.8 | 24.5 |
| 7 | 8/26/11 | 35 | 122.9 | 165.2 | 74.4 | 32.8 | 86.3 | 119.2 |
| 7 | 9/1/11 | 36 | 118.3 | 135.2 | 87.5 | 21.1 | 135.1 | 156.3 |
| 7 | 9/9/11 | 37 | 174.8 | 190.8 | 91.6 | 15.0 | 139.9 | 155.0 |
| 7 | 9/11/11 | 39 | 51.6 | 59.1 | 87.3 | 6.3 | 23.5 | 29.9 |
| 7 | 10/11/11 | 34 | 18.1 | 25.5 | 71.2 | 6.6 | 35.5 | 42.1 |
| 7 | 10/14/11 | 34 | 154.1 | 150.2 | 102.6 | 30.6 | 156.0 | 186.6 |
| 7 | 10/24/11 | 30 | 267.5 | 284.5 | 94.0 | 6.2 | 56.0 | 62.2 |
| 7 | 11/11/11 | 29 | 42.5 | 51.7 | 82.2 | 3.2 | 8.5 | 11.7 |
| 7 | 11/16/11 | 30 | 282.0 | 343.0 | 82.2 | 21.4 | 0 | 21.4 |
| 8 | 2/3/11 | 43 | 32.0 | 57.3 | 55.8 | 25.0 | 83.1 | 108.1 |
| 8 | 2/9/11 | 44 | 23.4 | 47.3 | 49.5 | 20.2 | 57.3 | 77.5 |
| 8 | 2/16/11 | 44 | 8.6 | 22.6 | 37.9 | 9.5 | 38.7 | 48.2 |
| 8 | 3/28/11 | 30 | 23.4 | 52.0 | 44.9 | 25.3 | 85.9 | 111.2 |
| 8 | 5/27/11 | 39 | 17.7 | 37.1 | 47.8 | 6.1 | 5.9 | 12.0 |
| 8 | 6/2/11 | 47 | 25.7 | 135.7 | 18.9 | 11.2 | 33.4 | 44.6 |
| 8 | 9/1/11 | 34 | 42.1 | 92.9 | 45.3 | 5.5 | 20.2 | 25.7 |
| 8 | 9/12/11 | 50 | 143.3 | 163.1 | 87.8 | 19.9 | 88.2 | 108.1 |
| 8 | 10/11/11 | 36 | 9.1 | 25.9 | 34.9 | 5.7 | 15.1 | 20.7 |

TABLE 2-continued

Patient summary for iron and phenazine concentrations

| Patient | Sample ID | FEV1 % | Fe(II) (µM) | Total Fe | Fe(II) % | PYO (µM) | PCA (µM) | Total (µM) |
|---|---|---|---|---|---|---|---|---|
| 8 | 10/14/11 | 36 | 162.3 | 178.6 | 90.9 | 22.4 | 50.3 | 72.7 |
| 8 | 10/20/11 | 42 | 143.9 | 156.1 | 92.2 | 3.8 | 14.9 | 18.7 |
| 9 | 2/3/11 | 65 | 7.3 | 52.5 | 13.9 | 28.1 | 31.9 | 60.0 |
| 9 | 2/4/11 | 59 | 22.3 | 36.0 | 61.9 | 28.1 | 29.8 | 58.0 |
| 9 | 3/22/11 | 48 | 38.4 | 82.7 | 46.5 | 17.4 | 15.5 | 32.8 |
| 9 | 7/8/11 | 48 | 85.0 | 222.5 | 38.2 | 26.4 | 21.2 | 47.7 |
| 9 | 8/2/11 | 62 | 26.0 | 76.5 | 34.0 | 5.8 | 10.0 | 15.8 |
| 9 | 8/4/11 | 61 | 51.0 | 157.0 | 32.5 | 7.2 | 3.9 | 11.1 |
| 9 | 10/4/11 | 66 | 38.7 | 42.7 | 90.7 | 3.8 | 2.4 | 6.2 |
| 9 | 11/16/11 | 50 | 121.6 | 123.9 | 98.1 | 23.2 | 12.5 | 35.7 |
| 9 | 11/22/11 | 56 | 53.9 | 50.7 | 106.4 | 15.8 | 8.6 | 24.5 |
| 9 | 11/28/11 | 56 | 186.0 | 200.0 | 93.0 | 14.3 | 9.6 | 23.9 |
| 10 | 2/7/11 | 70 | 11.0 | 23.7 | 46.5 | 7.7 | 5.1 | 12.7 |
| 10 | 11/21/11 | 67 | 234.0 | 315.0 | 74.3 | 6.0 | 13.7 | 19.7 |
| 11 | 2/9/11 | 59 | 0.0 | 3.5 | 0.0 | | | |
| 11 | 2/24/11 | 54 | 11.2 | 32.5 | 34.5 | 12.3 | 2.5 | 14.9 |
| 11 | 4/21/11 | 65 | 0.0 | 18.4 | 0.0 | 7.2 | 3.0 | 10.3 |
| 11 | 10/26/11 | 61 | 0.6 | 0.8 | 80.1 | 0.39 | 3.6 | 4.0 |
| 11 | 11/22/11 | 69 | 9.4 | 9.8 | 96.7 | | | |
| 12 | 2/14/11 | 38 | 4.4 | 5.9 | 75.6 | 33.3 | 29.8 | 63.1 |
| 12 | 4/11/11 | 30 | 6.4 | 29.1 | 22.0 | 15.2 | 5.3 | 20.5 |
| 12 | 4/21/11 | 34 | 70.4 | 93.7 | 75.1 | 16.2 | 4.4 | 20.6 |
| 13 | 2/15/11 | 96 | 1.4 | 24.7 | 5.5 | 16.0 | 20.2 | 36.2 |
| 13 | 3/14/11 | 80 | 2.9 | 25.2 | 11.7 | 6.5 | 9.2 | 15.7 |
| 13 | 3/18/11 | 110 | 2.7 | 34.1 | 7.9 | 0 | 3.5 | 3.5 |
| 13 | 3/26/11 | 125 | 0.3 | 2.7 | 10.3 | | | |
| 13 | 7/20/11 | 110 | 78.5 | 131.5 | 59.7 | 3.4 | 5.7 | 9.1 |
| 14 | 2/15/11 | 71 | 2.9 | 13.8 | 21.0 | 17.4 | 6.5 | 23.8 |
| 14 | 3/17/11 | 74 | 7.0 | 28.4 | 24.6 | 2.6 | 2.7 | 5.3 |
| 14 | 3/22/11 | 94 | 1.3 | 22.7 | 5.6 | | | |
| 14 | 6/23/11 | 36 | 71.5 | 189.0 | 37.8 | 9.7 | 0 | 9.7 |
| 14 | 7/19/11 | 57 | 63.0 | 95.0 | 66.3 | 49.0 | 2.8 | 51.8 |
| 14 | 11/15/11 | 65 | 42.0 | 60.9 | 69.0 | 3.3 | 12.2 | 15.6 |
| 15 | 2/23/11 | 95 | 4.3 | 5.8 | 74.0 | 0 | 2.4 | 2.4 |
| 15 | 4/21/11 | 81 | 0.0 | 17.7 | 0.0 | | | |
| 16 | 2/25/11 | 59 | 52.9 | 58.4 | 90.6 | 8.7 | 0 | 8.7 |
| 16 | 3/3/11 | 58 | 8.1 | 9.0 | 89.9 | 14.29 | 6.16 | 20.5 |
| 16 | 5/31/11 | 46 | 12.3 | 108.0 | 11.4 | | | |
| 16 | 8/30/11 | 27 | 15.2 | 49.8 | 30.5 | 10.7 | 22.8 | 33.5 |
| 16 | 10/10/11 | 44 | 14.7 | 17.3 | 84.7 | 12.5 | 0.6 | 13.1 |
| 17 | 3/21/11 | 26 | 21.3 | 54.1 | 39.3 | 21.4 | 41.3 | 62.8 |
| 17 | 6/23/11 | 29 | 49.8 | 129.8 | 38.4 | 30.0 | 5.5 | 35.5 |
| 17 | 6/29/11 | 31 | 26.5 | 124.9 | 21.2 | 30.7 | 7.0 | 37.7 |
| 18 | 3/24/11 | 107 | 3.0 | 6.8 | 44.4 | 0.7 | 21.0 | 21.8 |
| 18 | 11/16/11 | 99 | 3.8 | 19.4 | 19.4 | | | |
| 19 | 3/28/11 | 30 | 11.0 | 33.4 | 32.8 | 41.8 | 21.3 | 63.1 |
| 19 | 4/12/11 | 40 | 49.1 | 56.4 | 87.0 | 25.2 | 4.0 | 29.2 |
| 19 | 6/9/11 | 29 | 179.0 | 340.0 | 52.6 | | | |
| 19 | 6/14/11 | 41 | 10.4 | 24.4 | 42.6 | 10.3 | 1.0 | 11.3 |
| 19 | 6/17/11 | 44 | 13.2 | 106.5 | 12.4 | 19.1 | 4.8 | 23.9 |
| 19 | 9/13/11 | 41 | 8.4 | 30.2 | 28.0 | | | |
| 19 | 10/14/11 | 32 | 17.8 | 55.9 | 31.8 | 35.2 | 22.2 | 57.4 |
| 19 | 10/20/11 | 33 | 43.3 | 53.0 | 81.7 | | | |
| 19 | 10/24/11 | 43 | 58.1 | 65.2 | 89.2 | 7.6 | 11.1 | 18.7 |
| 22 | 5/9/11 | 47 | 63.1 | 99.1 | 63.7 | 3.1 | 1.9 | 5.0 |
| 22 | 11/11/11 | 44 | 32.8 | 40.8 | 80.5 | 1.8 | 10.3 | 12.1 |
| 22 | 11/8/11 | 35 | 9.4 | 14.5 | 64.5 | 1.0 | 5.6 | 6.6 |
| 22 | 11/16/11 | 44 | 1.1 | 13.9 | 7.8 | 1.2 | 5.5 | 6.7 |
| 23 | 5/10/11 | 78 | 1.1 | 29.1 | 3.6 | 5.0 | 0.4 | 5.4 |
| 25 | 6/23/11 | 68 | 54.0 | 145.0 | 37.2 | 1.2 | 12.2 | 13.4 |
| 25 | 7/21/11 | 63 | 43.0 | 56.5 | 76.1 | 3.8 | 2.3 | 6.1 |
| 25 | 7/26/11 | 83 | 22.5 | 37.5 | 60.0 | 2.2 | 1.0 | 3.3 |
| 25 | 7/28/11 | 83 | 0.0 | 35.5 | 0.0 | 7.7 | 3.8 | 11.6 |
| 25 | 8/2/11 | 76 | 0.0 | 4.5 | 0.0 | 4.9 | 0.3 | 5.3 |
| 25 | 8/4/11 | 89 | 0.0 | 2.0 | 0.0 | 5.6 | 2.6 | 8.1 |
| 25 | 9/1/11 | 86 | 54.4 | 88.3 | 61.7 | | | |
| 25 | 11/22/11 | 76 | 71.3 | 98.8 | 72.2 | 2.1 | 8.6 | 10.7 |
| 25 | 11/28/11 | 85 | 60.2 | 76.6 | 78.6 | 2.4 | 13.6 | 16.0 |
| 26 | 7/8/11 | 51 | 0.0 | 7.0 | 0.0 | 13.8 | 6.6 | 20.4 |
| 26 | 10/14/11 | 45 | 14.5 | 15.2 | 95.9 | | | |
| 27 | 10/14/11 | 54 | 2.3 | 6.1 | 38.4 | | | |
| 27 | 10/20/11 | 72 | 3.4 | 3.9 | 87.9 | 0.9 | 3.0 | 3.9 |
| 27 | 11/28/11 | 83 | 20.8 | 28.8 | 72.3 | 1.5 | 5.6 | 7.0 |
| 29 | 10/27/11 | 88 | 4.5 | 5.3 | 85.3 | | | |

Due to the temporal variability of sputum iron concentrations and differences in the number of samples collected for a given patient (Table 2), data were grouped over the entire period of the study and each patient's iron measurements was treated as an average, rather than as independent observations in order to test for correlations with patient disease state. The relevant data are reported in Table 3 below which reports values as mean concentrations+/−one standard deviation of iron detected in sputum samples collected over the study period. The values are conservative estimates based on FerroZine® and ICP-MS measurements (see FIG. 4).

TABLE 3

Summary of average Fe concentrations grouped by disease severity.

| Disease Severity | FEV1 | n | Total Fe (µM) | Fe(II) (µM) | Fe(II) % |
|---|---|---|---|---|---|
| Normal-Mild | >70 | 7 | 18 +/− 14 | 7 +/− 8 | 41 +/− 28 |
| Moderate | 40-69 | 2 | 48 +/− 38 | 28 +/− 27 | 52 +/− 10 |
| Severe | <40 | 5 | 62 +/− 20 | 39 +/− 22 | 56 +/− 15 |

The results summarized in Table 3 show that not only the total iron concentration increased with the severity of the disease, but also that Fe(II) increased significantly in patients were the severity of the disease was severely compromised.

On average, each patient had 42 µM total iron (range 3.7-118 µM) present in their sputum, which was highly dependent on the stage of disease (Table 3). These values are consistent with a range of studies reporting elevated iron levels in CF sputum and bronchoalveolar lavage (see e.g. [32], [33] and [35]), those studies however did not perform direct measurements of the iron oxidation state.

Figure 5:
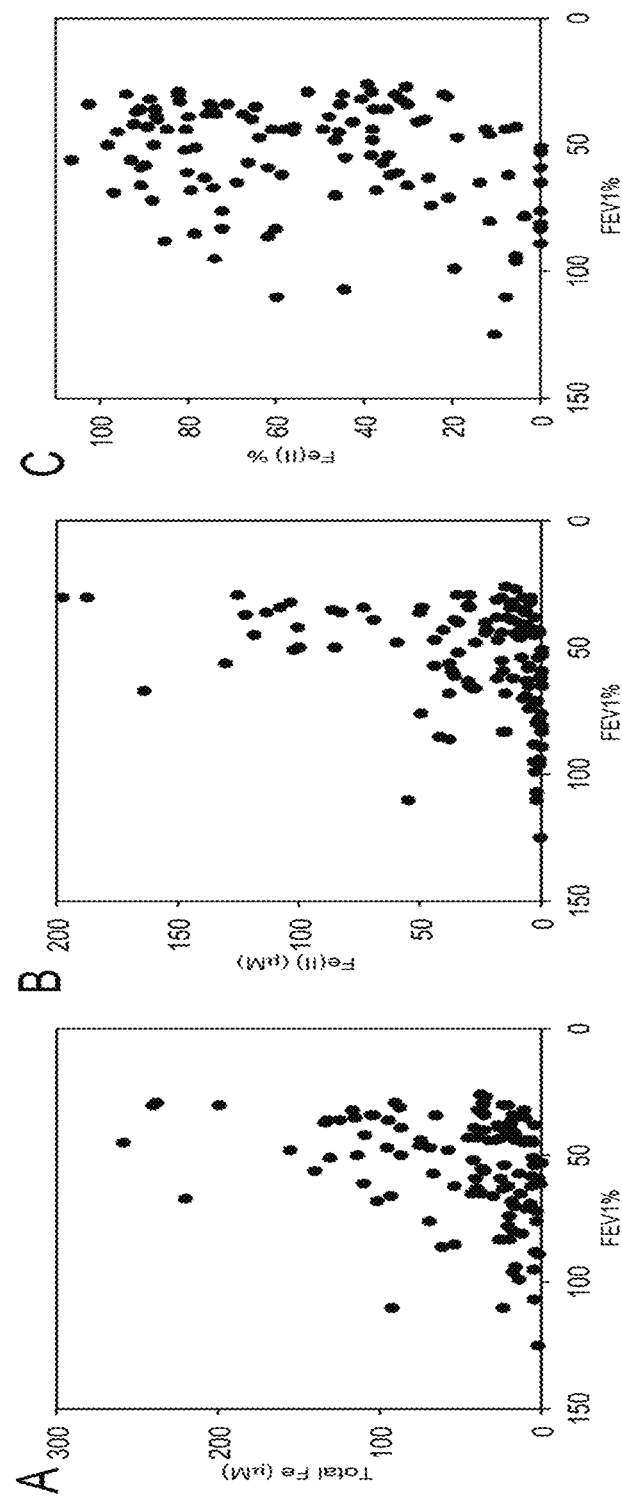
FIG. 5 shows diagram illustrating the results of direct detection of iron abundance and oxidation state within CF sputum.

In the present set of experiments data concerning iron abundance and oxidation state with cystic fibrosis patients were also retrieved and are reported in FIG. 5. In particular, in the illustration of FIGS. 5A-5C the concentration of total iron Fe(III)+Fe(II), concentration of Fe(II) and Fe(II) % measure all significantly increase as pulmonary function (FEV1%) declines. Accordingly those data support the conclusion that a correlation between total iron and FEV1%, derives from Fe(II) not Fe(III) as also confirmed by the experiments illustrated in Example 6.

Example 6: Correlation Between Total Iron and Ferrous Iron Increase and Declining Lung Function in Cystic Fibrosis Patients The data set of Table 3 retrieved in outcome of the experiments of Example 5, were clustered by patient (n=24), and Spearman rank analysis was performed as summarized in Table

TABLE 4

Summary of statistical relationships between iron concentrati disease severity (FEV1%)

| | N | Spearman Rank Coefficient | Sig. (Two-tailed) |
|---|---|---|---|
| Total Iron | 24 | −0.48 | 0.018 |
| Fe(III) | 24 | −0.21 | 0.316 |
| Fe(II) | 24 | −0.56 | 0.004 |
| Fe(II) % | 24 | −0.36 | 0.083 |

Figure 6:
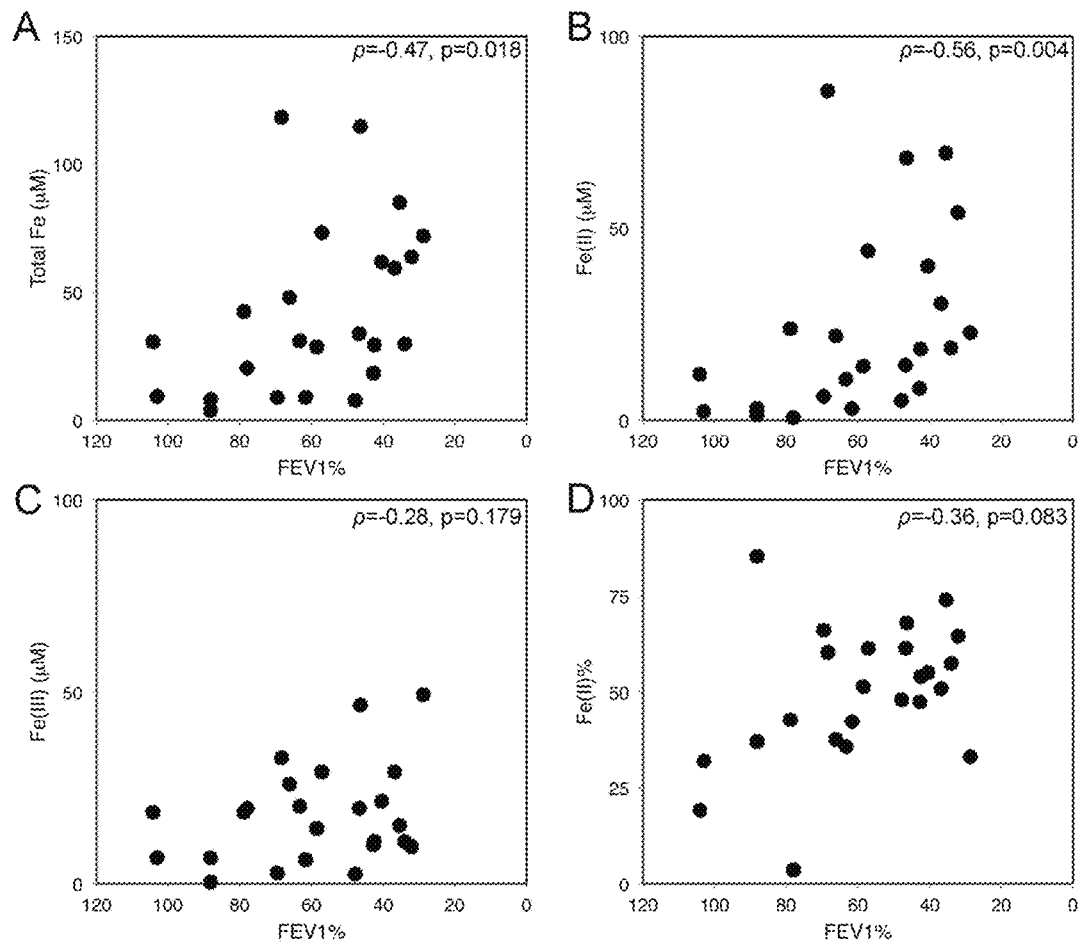
FIG. 6 shows diagrams illustrating the results of direct detection of iron abundance and oxidation state within CF sputum.

The correlation between total iron, Fe II and Fe III concentration detected in multiple sputum samples from CF patients and declining lung functions measure by FEV1% was also measured and the related results are reported in FIG. 6.

As illustrated in Table 4, the Spearman rank analysis revealed a significant negative correlation ($\rho=-0.47$, $p=0.018$) between total iron and declining lung function (measured by forced expiratory volume, FEV1%) which is also confirmed by the results of FIG. 6A.

Elevated iron levels (62+/−20 μM for severely infected patients; Table 3) were consistent with previous studies that quantified total iron levels and iron-related proteins in the CF airways [32] [33] [34]. Consistent with the expectations, a considerable amount of this iron was found in its ferrous form, as sputum from severely infected patients had 39+/−22 μM Fe(II).

Here, a highly significant negative correlation was found between absolute Fe(II) concentrations and disease status ($\rho=-0.56$, $p=0.004$; FIG. 6B), though a similar relationship was not found for Fe(III) ($\rho=-0.28$, $p=0.179$; FIG. 6C). The percentage of the total iron pool that was present as Fe(II) was also higher (though not significantly, $\rho=-0.36$, $p=0.083$) in patients with advanced disease states; in patients with severe lung obstruction (FEV1%<40), Fe(II) constituted 56+/−15% of the total iron pool (FIG. 6D).

These data confirm a correlation between ferrous iron and severity of the cystic fibrosis disease and reveal that the chemical environment of the lung is dynamic and evolves with respect to its iron redox chemistry as CF disease progresses.

Example 7: Increased Fe(II) Correlates with Elevated Phenazine Concentrations Supporting Conclusion at Least a Portion of Detected Fe(II) is Bioavailable The alteration of total iron concentrations and the rise in Fe(II) over time likely results from multiple inputs by both host and pathogen [32] [34]. For example, iron levels are known to increase due to inflammation [36], loss of intracellular iron by ΔF508 epithelial cells [37], altered production of the iron-related proteins heme, ferritin and transferrin [34] and their proteolysis [38].

In addition, redox-active phenazine metabolites produced by *P. aeruginosa* are abundant in CF sputum [30], some of which can readily reduce Fe(III) to Fe(II) [39]. Iron reduction by phenazines has been demonstrated to circumvent iron chelation in vitro, promoting the formation of biofilms [12].

Based on recent demonstration of a strong correlation between sputum phenazine levels and pulmonary decline [30], HPLC was used to assess whether elevated levels of two phenazines, pyocyanin (PYO) and phenazine-1-carboxylic acid (PCA), also correlated with high Fe(II) concentrations. The results are reported in FIGS. 7A-7C.

Consistent with the previous findings from an independent adult patient cohort, the majority of sputum samples tested had detectable phenazine concentrations (76 of 97 samples tested contained >10 μM total phenazine; Table 2).

Figure 7:
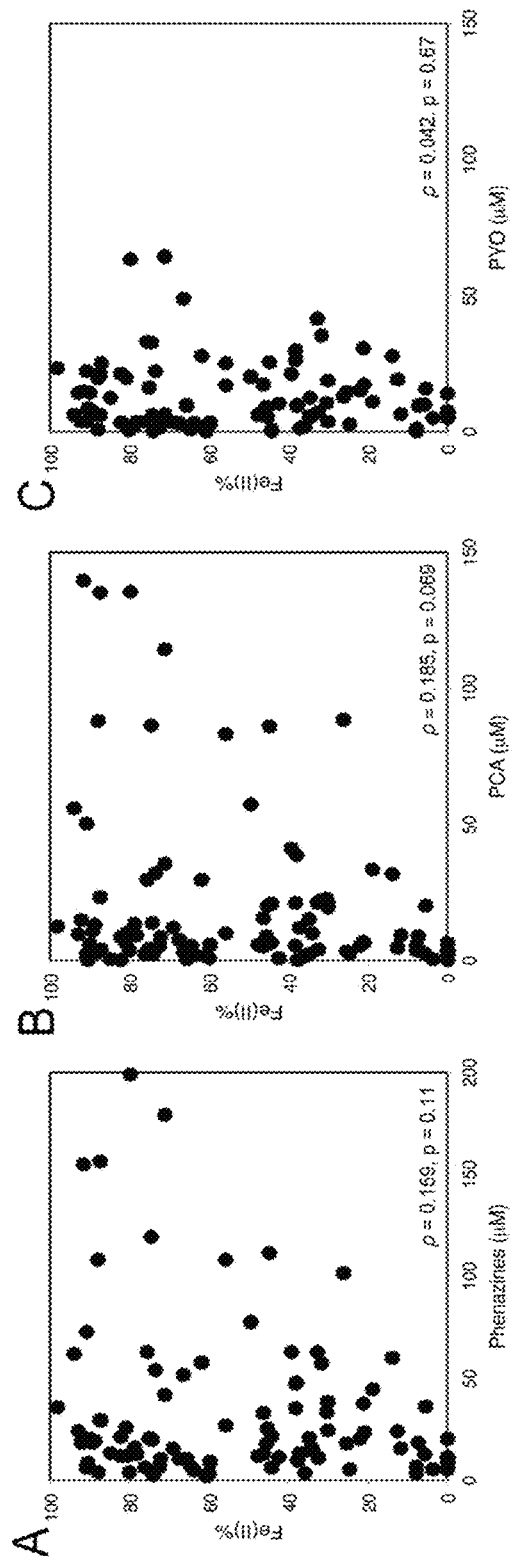
FIG. 7 shows diagrams illustrating Fe(II) percentage of the total iron pool relative to sputum phenazine content. In particular.

In sputum samples with low concentrations of phenazines, the percentage of the total iron pool that was Fe(II) ranged anywhere from 0 to 100%, revealing that phenazines are not required for the presence of ferrous iron (FIG. 7A). Yet, phenazines may facilitate Fe(III) reduction in vivo, as evidenced by the generally high percentage of Fe(II) once phenazine levels rise above ~50 μM in expectorated sputum.

Treating each sputum sample independently, a strong trend was found between PCA abundance and Fe(II) % ($\rho=0.185$, $p=0.069$), yet no correlation between PYO abundance and Fe(II) % ($\rho=0.042$, $p=0.67$) (FIGS. 7B,7C). This may reflect that PCA can reduce Fe(III) much faster than PYO under anoxic conditions [39].

Whether the PCA/Fe(II) % trend would pass a test of statistical significance ($p<0.05$) with additional sampling was not established. Samples were treated independently in this analysis in order to compare phenazine concentrations and Fe(II) % within a particular environment; given the variability of sputum chemistry over time (and likely also space) for individual patients (FIG. 5 and Table 2), averaging and comparing these values per patient would not have been meaningful. It is however expected that the PCA/Fe(II) % trend would pass a test of statistical significance ($p<0.05$) if performed.

In view of the above result in particular in view of the detection of a high level of Fe(II)-specific bqsRS expression (relative to oprI) in a majority of sputum samples (compared to tightly-controlled laboratory cultures), it was concluded that at least some portion of the Fe(II) pool is sensed by *P. aeruginosa* in vivo Example 8: Fe(II)-Responsive Genes and Multiple Iron Uptake Pathways are Expressed by *P. aeruginosa* in Planktonic *P. Aeruginosa* Cultures and within CF Sputum Further Supporting Conclusion at Least a Portion of Detected Fe(II) is Bioavailable Given the abundance of Fe(II) in vitro, the extracellular Fe(II) was predicted to be bioavailable to *P. aeruginosa* within the airways. To test this prediction, a quantitative real-time PCR (qRT-PCR) approach was used to measure the expression patterns of two Fe(II)-responsive genes within expectorated sputum relative to their expression patterns under controlled conditions.

The *P. aeruginosa* genes bqsR and bqsS encode a putative response regulator and sensor kinase, respectively, of a two-component system that was previously shown to be specifically upregulated in response to extracellular Fe(II) [40]. The NCBI Gene Expression Omnibus (GEO) database (at the www webpage ncbi.nlm.nih.gov/geo/) was mined for microarray data generated for *P. aeruginosa* grown under conditions relevant to the CF lung environment. The retrieved data are reported in Table 5.

TABLE 5

Gene Expression Omnibus (GEO) database microarray data for *P. aeruginosa* grown under various growth conditions relative to the CF lung.

|  | 04180 | bqsS | bqsR | feoA | feoB | hasA p | fptA | pvdA |
|---|---|---|---|---|---|---|---|---|
| Artificial sputum media[a] | − |  |  | − |  |  | −−− | − |
| Low pH (6.0) |  |  |  | + | + | − | − | − |
| low O2 | + |  |  | + | + | + |  |  |
| High nitrate |  |  |  | +++ | +++ |  | +++ |  |
| Phosphate starvation | −−− |  |  | −−− |  | +++ |  | +++ |
| Excess sulfur | + |  |  |  |  | − |  |  |
| Copper shock | − |  |  | + |  | Δ |  | + |
| Citrate |  |  |  |  |  |  |  |  |
| Palmitate |  |  |  |  |  |  |  |  |

TABLE 5-continued

Gene Expression Omnibus (GEO) database microarray data for P. aeruginosa grown under various growth conditions relative to the CF lung.

|  | 04180 | bqsS | bqsR | feoA | feoB | hasAp | fptA | pvdA |
|---|---|---|---|---|---|---|---|---|
| Phosphotidyl inositol |  |  |  |  |  | − |  |  |
| Phenylacetic acid |  |  |  |  |  |  |  |  |
| Oxidative stress |  |  |  |  |  | Δ |  |  |
| Azithromycin | cΔ | Δ | Δ |  | − | Δ | − | --- |
| Colistin |  |  |  |  |  |  |  |  |
| Tobramycin |  |  |  | Δ | Δ |  | --- |  |
| Temperature |  |  |  |  |  |  |  |  |
| Biofilm |  | + |  |  | + | + |  |  |
| Small colony variants | +++ |  |  |  |  | +++ | +++ |  |
| Mucoidy |  | + |  |  |  | Δ |  | Δ |
| PQS |  |  |  |  |  |  |  |  |
| Response to airway epithelia |  |  |  |  |  | +++ | + | +++ |
| Catabolite repression control (crc) |  |  |  |  |  |  |  |  |
| adenosine |  | − | − | − | − | − |  |  |

[a] symbols denote response in treatment relative to wild type or untreated control
[b] − slight down-regulation, --- downregulation, + slight up-regulation, +++ upregulation,
[c] Δ denotes poor or invalid microarray data These datasets revealed no differential expression of bqsRS in response to multiple environmental stimuli, including low oxygen, pH, phosphate starvation, oxidative stress, biofilm formation, and various antibiotic treatments (Table 5). Thus, bqsRS expression levels (relative to the constitutively-expressed gene oprI) serve as a reliable proxy for the bioavailability of Fe(II) in the lung.

Figure 8:
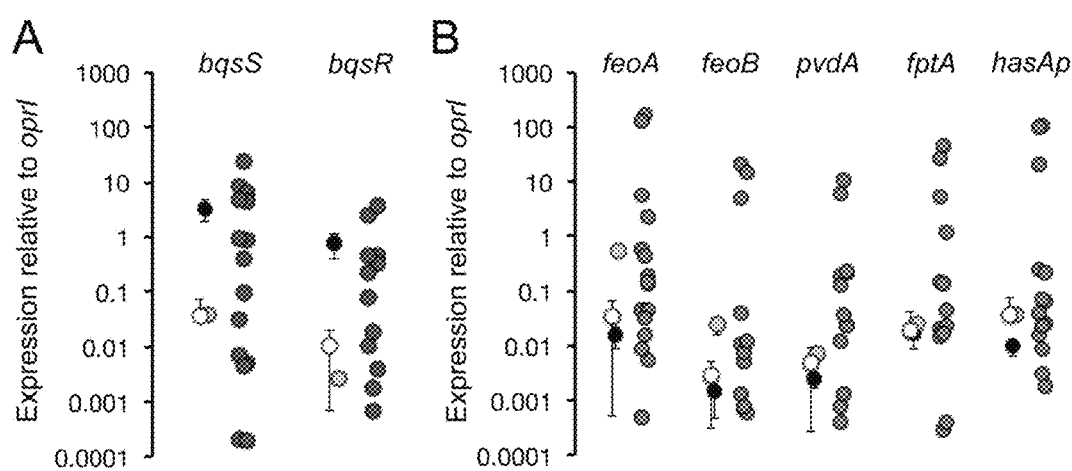
FIG. 8 shows diagrams illustrating the results of experiments directed to detect expression levels Fe(II)-relevant gene expression in CF sputum and planktonic cultures of P. Aeruginosa relative to the constitutively-expressed gene oprI In particular.

The expression levels of bqsS and bqsR relative to the constitutively-expressed gene oprI were therefore measured in planktonic cultures of P. aeruginosa in response to 50 μM Fe(II) relative to 50 μM Fe(III) or no treatment and in cystic fibrosis sputum samples in a further set of experiments illustrated in FIG. 8A where the transcriptional activity is shown relative to the endogenous housekeeping gene, oprI.

As can be seen in FIG. 8A, the Fe(II)-relevant bqsS gene expression is upregulated in planktonic cultures of P. aeruginosa in response to 50 μM Fe(II) (black) relative to 50 μM Fe(III) (white) or no treatment (light grey). A similar result is seen with bqsR (FIG. 8A). By comparison, expression levels of these Fe(II)-sensitive genes in CF sputum (FIG. 8A dark grey) vary over five orders of magnitude.

In particular, as previously observed, anaerobically-grown laboratory cultures of P. aeruginosa upregulated bqsS (>90-fold) in response to 50 μM Fe(II) relative to no treatment or treatment with 50 μM Fe(III) (FIG. 8A). Likewise, bqsR was highly expressed (>70-fold) in response to Fe(II) relative to other treatments. These gene expression patterns in controlled cultures were utilized to gain insight into the iron oxidation state perceived by P. aeruginosa in sputum. Consistent with the direct iron analyses, when bqsR and bqsS transcripts from sputum samples were quantified, expression was detected within the majority of patients (FIG. 8A).

Transcriptional activity varied between sputum samples, however, 8 of 16 patients harbored relative bqsS expression patterns comparable to Fe(II)-treated laboratory cultures. bqsR transcripts were also detected in the majority of sputum samples we tested, and many had relative expression levels comparable to Fe(II)-treated planktonic cultures. Unfortunately, technical limitations prevented us from measuring gene expression and iron content in the same sputum sample (see Materials and Methods). Despite potential differences in degradation rates for each transcript (FIG. 1), given the high direct measurements of Fe(II) in sputum, previous microarray data, and control experiments showing specific upregulation of bqsRS to Fe(II), the results are interpreted to indicate that the iron pool within the CF airways is of a mixed oxidation state, and that the infected lung environment frequently includes a ferrous portion that is sensed by P. aeruginosa.

The expression levels of feoA and feoB fptA, pvdA, and hasAp relative to the constitutively-expressed gene oprI were therefore measured in planktonic cultures of P. aeruginosa in response to 50 μM Fe(II) relative to 50 μM Fe(III) or no treatment and in cystic fibrosis sputum samples in a further set of experiments illustrated in FIG. 8B where the transcriptional activity is shown also relative to the endogenous housekeeping gene, oprI.

In particular feoA/B (encoding a ferrous iron transporter), fptA (ferripyochelin receptor), pvdA (pyoverdine biosynthetic protein), and hasAp (haem uptake protein) were targeted and quantified their relative expression levels in each sputum sample relative to oprI.

FIG. 8B also shows upregulation of expression of diverse iron uptake pathways within CF sputum. feoA and feoB encode proteins that transport Fe(II), while fptA, pvdA, and hasAp encode proteins that are involved in Fe(III) acquisition. The results of the related experiments of detection of P. aeruginosa gene transcripts encoding diverse Fe(II) and Fe(III)-specific uptake proteins also support the conclusion of a mixed-oxidation state of lung iron (FIG. 8B).

Consistent with previous in vitro studies demonstrating that P. aeruginosa grown in the presence of a sputum-derived medium expresses diverse iron-acquisition related genes [41], the above results indicate that genes involved in pyoverdine, pyochelin and heme uptake to be expressed in sputum, similar to another recent study [42]. In addition, direct measurements have also confirmed the presence of the siderophore pyoverdine in a high percentage of CF patients, but not all, indicating that P. aeruginosa uses multiple mechanisms for iron acquisition within the host [43]. Intriguingly, the data reported in the present example indicates that multiple iron uptake pathways are expressed simultaneously in several patients and several (e.g. pvdA, fptA and hasAp) do not appear to be iron-responsive under anoxic conditions (FIG. 8B). This apparent loss of Fur-regulation is expected to also reflect mutations that accrue as infections progress, as has been documented [44] and therefore further confirming expected effect.

Example 9: Fe(II)-Responsive Genes and Multiple Iron Uptake Pathways are Expressed within Sputum of Cystic Fibrosis Patients with Different Disease Severity Supporting Correlation Between Bioavailable Fe(II) and Disease Severity The expression values of bqsS, bqsR feoA and feoB fptA, pvdA, and hasAp detected in sputum of cystic fibrosis patients are reported in a patient by patient series of diagrams shown in FIG. 9. Expression of bqsS, and bqsR was also detected across the spectrum of cystic fibrosis severity and the results illustrated in FIG. 10 wherein the bqsS, and bqsR expression related to the constitutively expressed housekeeping gene, oprIi is shown relative to forced expiratory volume, FEV1%.

Figure 9:
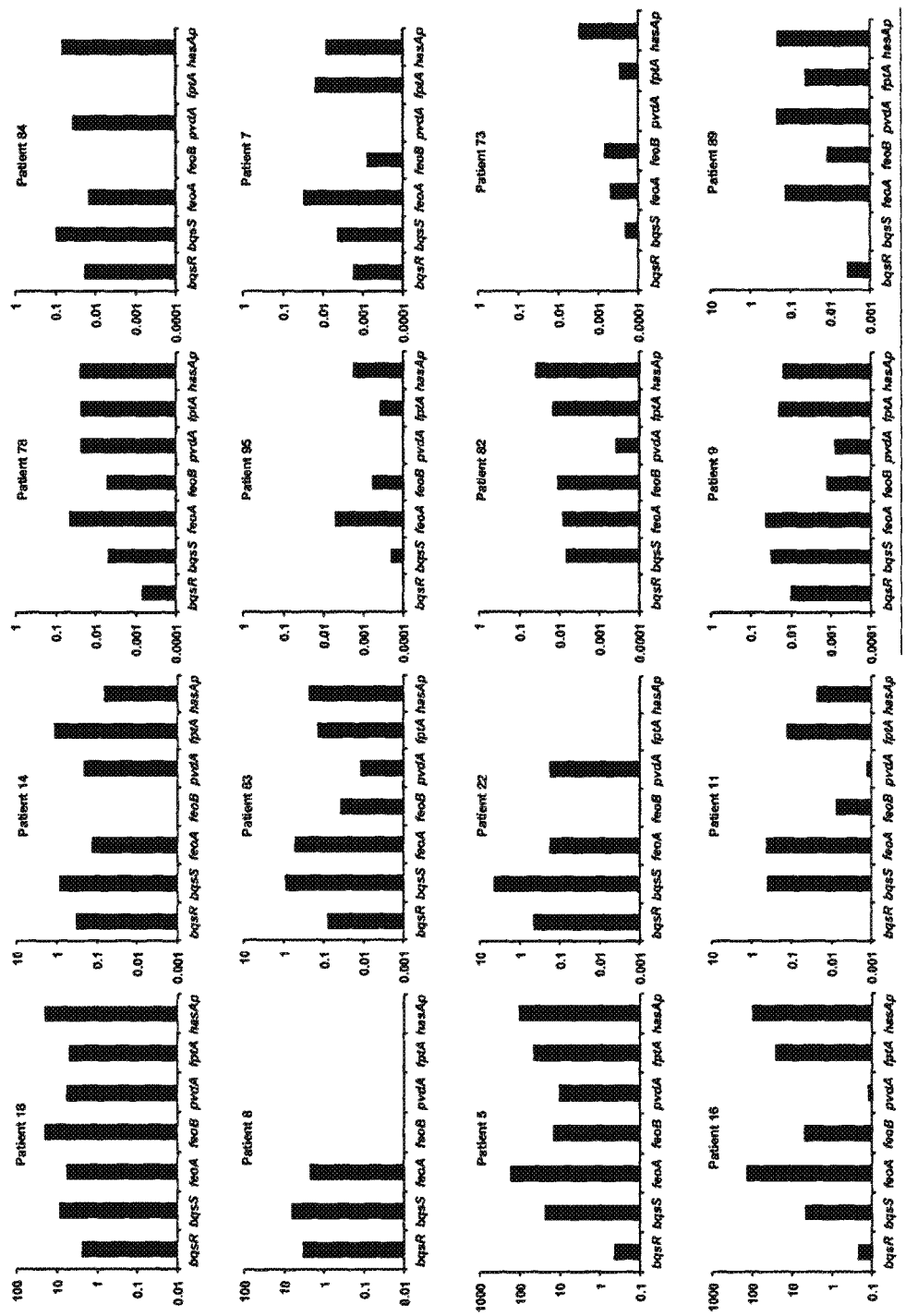
FIG. 9 shows diagrams illustrating results of experiments directed to detect within patient expression of iron-specific genes in CF sputum. Expression values are shown relative to oprI. Bars represent the average of triplicate measurements on a given gene in a single sputum sample. Note variation in y-axes. Primer efficiency values are provided in Table 1 in the Examples section.
Figure 10:
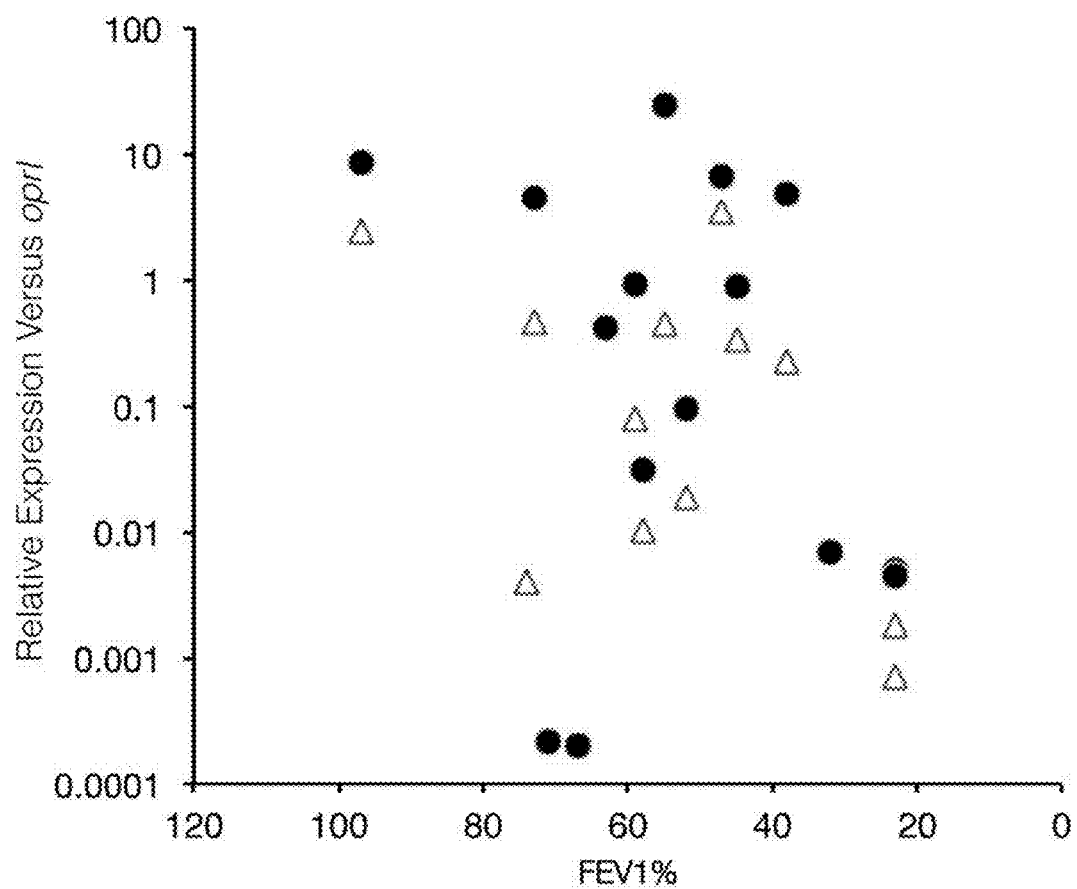
FIG. 10 shows a diagram illustrating expression of Fe(II)-sensitive genes bqsS and bqsR relative to disease severity. In particular in the diagram of FIG. 10 expression of bqsS (●) and bqsR (∆) gene expression relative to the constitutively expressed housekeeping gene, oprIi is shown relative to forced expiratory volume, FEV1%.

As can be seen by the illustration of FIG. 9, in a majority (75%) of patients, the prevalence bqsR and bqsS gene expression was comparable within patients. However, there was not a significant correlation between bqsRS transcriptional levels and disease severity (bqsR, p=0.13; bqsS, p=0.01) as can be seen by the illustration of FIG. 10). This is not surprising because the relative expression of each gene was previously shown to be upregulated in response to Fe(II) levels greater than 10 µM. In our patient cohort, on average, Fe(II) was frequently detected at levels above 10 µM, even at patients in early stages of disease. Thus, one would expect expression of these Fe(II)-sensitive genes across the spectrum of disease severity in response to the mixed-oxidation state of the iron pool.

Transcripts for each gene were detected in the majority of sputum samples analyzed (feoA, 15 out of 16 patients; feoB, 11/16; fptA, 13/16; pvdA, 11/16; hasAp, 14/16), though relative expression levels of each gene varied over five orders of magnitude between patients. Uptake systems for both iron oxidation states were simultaneously expressed within several individual patients (FIG. 9), consistent with a recent study that investigated the expression of these genes in an independent patient cohort [42].

Yet, the expression of Fe(II) uptake pathways did not correlate with the suppression of uptake pathways specific for Fe(III), or vice versa. Furthermore, because the regulation of these iron uptake pathways is complex [45] [46] and some (pvdA, fptA, and hasAp) appear to be independent from the oxidation state under anoxic conditions (FIG. 8B), these expression patterns alone are not predictive of the iron oxidation state in vivo. Rather, the expression of multiple iron uptake systems is supportive of an interpretation that $P.$ aeruginosa utilizes a mixed-oxidation pool of iron within the CF sputum environment.

The above data therefore supports the conclusion that the correlation between Fe(II) observed in the experiments of Examples 5 and 6 relate at least in part to bioavailable ferrous iron.

Figure 11:
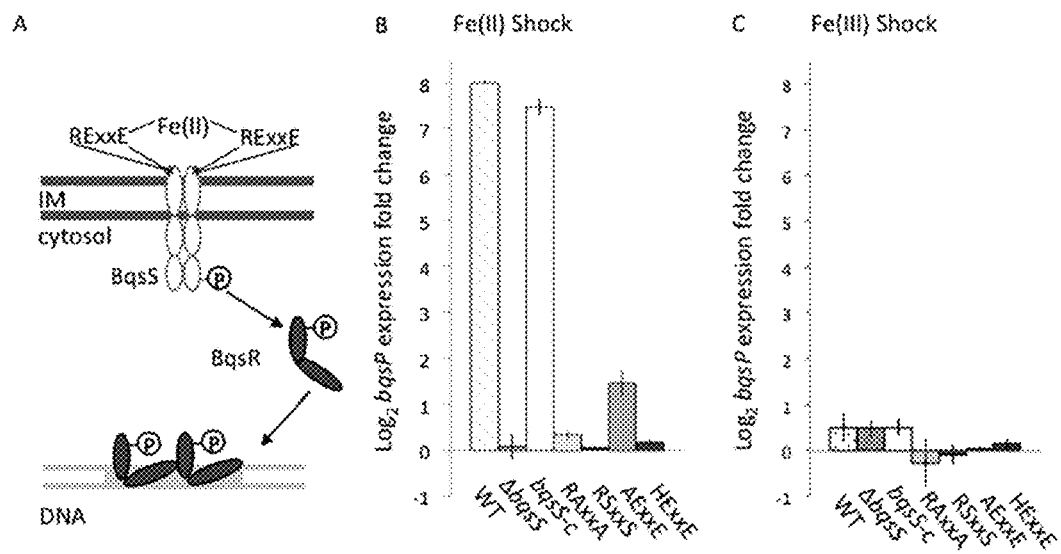
FIG. 11 shows BqsS senses Fe(II) through the RExxE motif. (A) Model of BqsS activation by Fe(II) through the periplasmic RExxE motif and signal transduction to BqsR. This model is based on analogy to similar two-component systems (54). (B) Point mutations of the RExxE motif in BqsS show a decreased transcriptional response to Fe(II), suggesting that this may be the binding site of ferrous iron. From left to right, the bars show the log 2-fold change in the bqsP (the first gene in the bqs operon) WT, bqsS, _bqsS-c (_bqsS::pbqs-bqsS), RAxxA (_bqsS::pbqs-RAxxA), RSxxS (_bqsS::pbqs-RSxxS), AExxE (_bqsS::pbqs-AExxE), and HExxE (_bqsS::pbqs-HExxE) strains. (C) Point mutations of the RExxE motif in BqsS show no transcriptional response to Fe(III). From left to right, the bars show the log 2-fold change in the bqsP (the first gene in the bqs operon) WT, _bqsS, _bqsS-C (_bqsS::pbqs-bqsS), RAxxA (_bqsS::pbqs-RAxxA), RSxxS (_bqsS::pbqs-RSxxS), AExxE (_bqsS::pbqs-AExxE), and HExxE (_bqsS::pbqs-HExxE) strains.

Example 10: RExxE Motif in BqsS is Required for BqsRS Activation in P. Aeruginosa Multiple bacterial protein prediction programs (TMpred [22] and DAS [23]) predict the sensor kinase BqsS to be a two-pass transmembrane protein with a periplasmic region containing an RExxE motif (FIG. 11A). To determine whether the RExxE motif is involved in Fe(II) sensing, strains with substitutions were generated in these residues (RExxE) in a AbqsS mutant background. Alleles with substitutions in the RExxE residues were created and expressed from a chromosomal insertion at the glmS locus comprised of the bqs promoter and the bqsS gene. Activation of the BqsS variants in the presence of Fe(II) was measured by following the transcriptional response of bqsP, the first gene in the bqs operon, to 200_M Fe(II) [here referred to as "Fe(II) shock"]. When the glutamates at positions 45 and 48 in BqsS were replaced with alanine (RAxxA) or serine (RSxxS), the transcriptional Fe(II) response was completely abolished. No change was seen in the levels of bqsP in these mutants, as for the bqsS negative control (FIG. 11B). The arginine residue at position 44 is also critical: when this amino acid was replaced with alanine (AExxE), the Fe(II) shock response decreased by 98%, and when replaced with histidine (HExxE), the response was abolished. None of the site-directed mutants responded to Fe(III) shock (FIG. 1C). Fe(II) sensing thus appears to be mediated through the periplasmic RExxE motif in BqsS.

The above results indicate that BqsS recognizes Fe(II) via the RExxE motif in its periphasmic domain, based on analogy to other Fe-sensing proteins. Although it is unusual for glutamates to prefer Fe(II) to Fe(III), the strongly positive arginine may tune the ligand environment to prefer the less positively charged Fe(II) over Fe(III).

The RExxE motif is just one strategy by which cells sense Fe(II). Other systems may be employed by other cells utilizing a different motif.

Example 11: Interfering with Bioavailable Fe(II) Limits Biofilm Formation Under Anoxic and Oxic Conditions Given that the CF sputum environment contains a mixture of Fe(III) and Fe(II), the implications for treating biofilm infections were investigated. In particular it was investigated whether abundant Fe(II) levels in infected environments compromise the success of Fe(III)-specific chelation therapies targeting P. aeruginosa. This was first suggested in a recent study that tested the efficacy of several iron-binding compounds in the disruption of P. aeruginosa biofilm growth under both oxic and hypoxic conditions [47].

While biofilm formation was prevented under most conditions tested, the specific oxidation state of iron was unknown. In view of these experiments, a high-throughput biofilm assay was utilized to measure biofilm formation in the presence of Fe(III) and Fe(II) with or without oxidation-state specific iron chelators.

First, it was tested whether FerroZine®, an Fe(II)-specific chelator, could act synergistically with conalbumin, a Fe(III)-specific chelator, to prevent biofilm development under anoxic or oxic conditions. The related results are illustrated in FIG. 12A and FIG. 12B.

Figure 12:
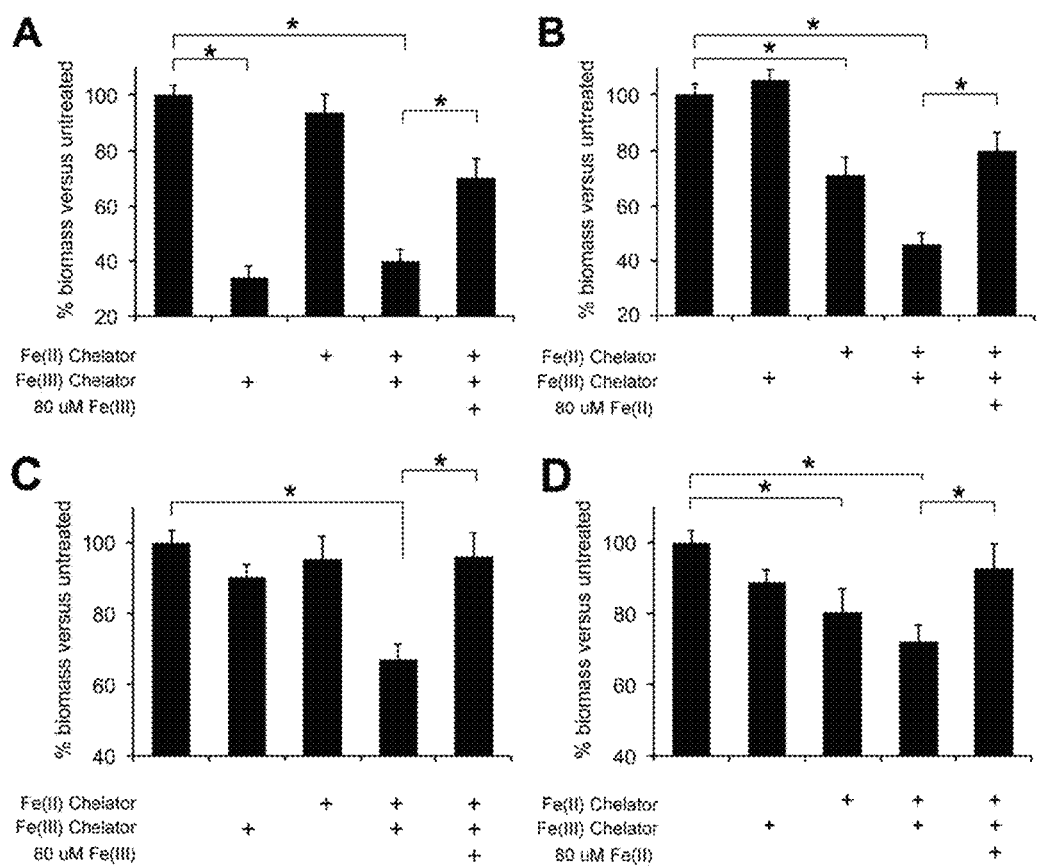
FIG. 12 shows diagrams illustrating results of experiments directed to detect biofilm growth prevention and biofilm dissolution following administration of Fe(II), Fe(II) chelator or both under aerobic and anaerobic conditions. In particular.

Consistent with previous studies [48] [47], 100 µM conalbumin prevented biofilm formation by 66% (p<0.001) under aerobic conditions where all iron (20 µM) was Fe(III) (FIG. 12A). In contrast, 200 µM FerroZine® (Fe(II)-specific) had no significant effect nor did the combination of FerroZine® and conalbumin treatments relative to conalbumin alone.

Conversely, under hypoxic conditions designed to mimic airway microenvironments during late stage infection, conalbumin was ineffective in preventing biofilm accumulation when ~10 µM Fe(II) and 10 µM Fe(III) were present (FIG. 12B). Here, 200 µM FerroZine® significantly reduced biofilm accumulation by 29% (p=0.012) and more notably, the combination of 100 µM conalbumin and 200 µM FerroZine® reduced biofilm accumulation by 54% (p<0.001), suggesting that targeting both oxidation states of iron in vivo might be more effective than targeting Fe(III) alone in the prevention of biofilm growth. Under both oxic and anoxic conditions, the addition of 80 µM iron (resulting in 100 µM total) in excess of the chelation capacity (conalbumin binds iron in a 2:1 ratio; FerroZine®, 3:1) restored biofilm accumulation, demonstrating that the chelator effect is likely due to iron sequestration rather than non-specific interactions.

Example 12: Combined Fe(III)/Fe(II) Chelation Promotes Biofilm Dissolution Under Anoxic and Oxic Conditions In addition to signaling biofilm formation, iron is essential for maintenance of established biofilm communities [11]. Therefore similar mixed Fe(II)/Fe(III) chelation experiments performed in Example 10 were performed targeting mature biofilms to test the ability of conalbumin and FerroZine® to dissolve bacterial biofilms that have already formed under anoxic or oxic conditions. The related results are reported in FIG. 12C and FIG. 12D.

Under aerobic conditions (FIG. 12C), the application of either conalbumin (100 µM) or FerroZine® (200 µM) in molar excess of iron in the growth medium showed minimal effect on biofilm dissolution. We hypothesized that this is due to the presence of both Fe(III) and Fe(II) in the hypoxic interior of aerobically-grown biofilms. Consistent with this prediction, the combined application of both Fe(III) and Fe(II) chelators revealed a synergistic dissolution effect, resulting in a 33% reduction (p=0.01) of biomass in the presence of oxygen. The addition of excess iron restored the untreated phenotype, corroborating an iron-specific mechanism of chelator-induced dispersal.

Similarly, 100 µM conalbumin did not significantly reduce established biofilm growth under anoxic conditions (FIG. 12D). However, significant biofilm dissolution (20%; p<0.001) was observed in the presence of 200 µM FerroZine®, indicating that *P. aeruginosa* biofilms can reduce Fe(III) present in the growth medium. More notably, when applied together with conalbumin, FerroZine® promoted further dissolution of established biofilms at levels comparable to those under oxic conditions (28%; p<0.001), supporting the case for targeting both Fe(III) and Fe(II) to disrupt *P. aeruginosa* biofilm growth in the CF airways.

In an additional set of experiments, biofilm growth was performed as described (see Materials and Methods). Following anoxic growth, biofilms were treated with iron chelators (conalbumin and FerroZine®) alone or in combination with tobramycin (8 µg/ml). The related results are reported in FIG. 13.

Figure 13:
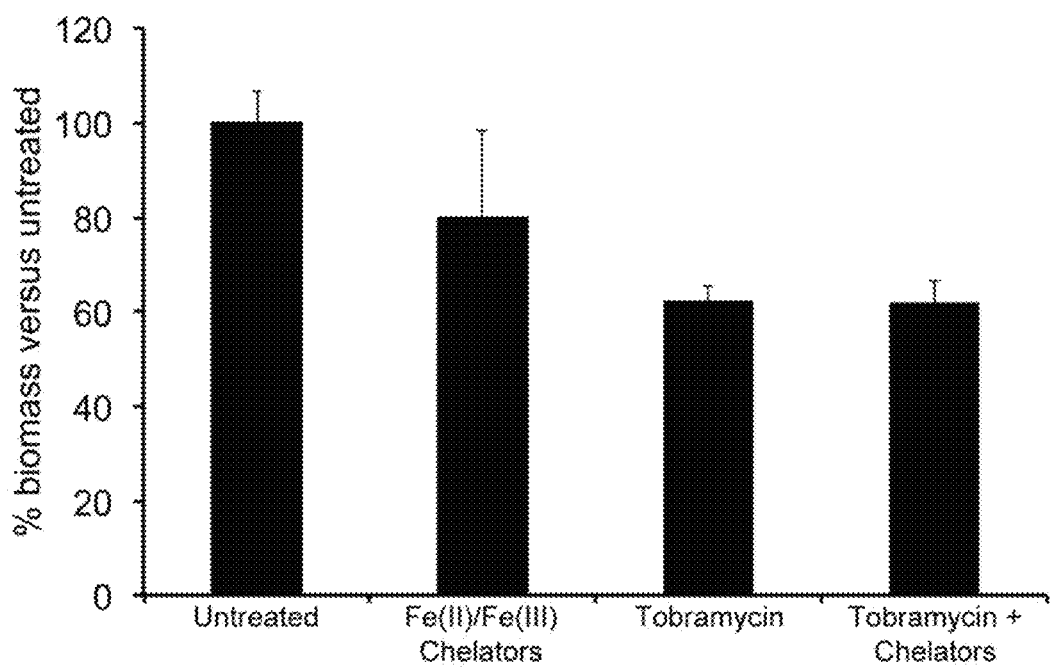
FIG. 13 shows a diagram illustrating the results of— Antibiotic treatment of iron-chelator challenged anoxic biofilms. In particular in the illustration of FIG. 13 percentage of biofilm mass versus untreated is reported relative to iron chelators (conalbumin and FerroZine®) alone or in combination with tobramycin (8 µg/ml) following growth under anoxic condition

In contrast to previous experiments performed under oxic conditions [49], dual exposure to iron chelators and tobramycin did not exhibit a synergistic effect under anoxic conditions (FIG. 13). The minimum biofilm inhibitory concentrations (BIC) were also determined under oxic conditions using the same biofilm assay and were consistent with those previously reported [50].

Example 13: Combined Fe(III)/Fe(II) Chelation Promotes Biofilm Dissolution Under Aerobic Conditions in Equipment Surfaces All of the instrumentation in the Caltech Flow Cytometry Cell Sorting Facility became contaminated in February 2014 with what it was thought to be a fungus. Attempts at cleaning the instrumentation using microbicide, bleach and commercial sheath buffer which contains a microbicide were successful for the analyzers, but unsuccessful for the sheath tanks.

In particular, attempts at cleaning the sheath tanks were first made with a microbicide that is made on the premises, namely phosphate buffered saline, made every day for the following day and by bleach failed to eliminate contamination. By the end of the second day following cleaning the sheath tank was cloudy and users were reporting a white contamination in their cultures after 4-5 days of mammalian cell culture. There are many fluidic tanks and lines in these instruments and there is a manifold that directs the fluidics.

In view of the above it was assumed that it was a fungal infection and the instrumentation was then extensively washed with bleach. All the fluidic filters were taken off the instrument and replaced with homemade bypasses to prevent the filters from disintegrating in the instrument. Many rounds of 100% bleach for 1-2 hours were performed running in all of the tanks and many aseptic sort procedures (a protocol routinely used between samples) with bleach in all the tanks and the sample injection port. This did not cure the problem as the white contamination was present after sorting and culturing the sorted cells.

In view of the unsuccessful treatment with bleach, upon indication of the manufacturer 100% white vinegar was also used in all the tanks and sample injection port, where the white vinegar was left overnight in situ and then running an hour in the morning before rinsing with sterile water. This protocol was followed by treatment with 70% ethanol in all the tanks and sample injection port for several hours and sitting overnight before washing out with sterile water. Again, sorted customer samples came back to us with the white contamination after four days of culture. The instrument was therefore cleaned by incubating with methylparabens followed by a wash/bleach/wash.

Failure by the above procedures to eliminate the contamination indicated a contamination which appeared not possible to clean up with conventional methods.

Samples were sent to the American Research and Testing and the analysis were subcontracted to Michelson Laboratories for plate counts and identification. In particular, the outflows were tested from the FACSAriaIIu otherwise known as the waste stream or the sort stream.

The results of the Michelson laboratories testing are shown in FIGS. 14 to 16. The outflow from the Aria, was testing positive for *Ochrobactrum anthropi* a known microorganism to be found in biomedical devices and likes especially to stick to synthetic materials like silicone and catheter tubing. Traces of *Pseudomonas mendocina* and *Pseudomonas stutzeri* were also detected as well as several additional bacteria were also found to contaminate the instrument as indicated in the tables from the report of the Michelson Laboratories illustrated in FIGS. 14 to 16.

A solution was then prepared comprising 200 uM EDTA and 200 uM FerroZine® (chelators that have highest affinity for ferric and ferrous iron, respectively). This formula was based upon the experiments reported in Examples 11 and 12 resulting in blocking and dissolving biofilm formation by a different organism, *Pseudomonas aeruginosa* (see paper by Hunter et al, 2013 incorporated herein by reference in its entirety) [16]. The formula was effective to remove the contamination reported by the Michelson Laboratory and is indicative of ability of a Fe(II) and Fe(III) combined treatment to remove different types of biofilms under various conditions, and in particular under oxic conditions.

Biofilm formation is a huge problem in many settings, affecting not only the community of people who use flow cytometers but people who are working with medical devices (catheters, etc.) that readily get contaminated by biofilms.

Accordingly, the above experiments confirm that a mixture of ferric and ferrous iron chelators is expected to be broadly useful in removing bacteria in a much broader context than treatment of *P. Aeruginosa*.

The data reported in the above examples support the conclusion that interfering with a mixed-oxidation state iron pool can limit biofilm formation and promote biofilm dissolution. The data reported in the above examples also support the conclusion that the mixed-oxidation approach using a combined Fe(II) and Fe(III) (e.g. conalbumin/FerroZine®) combined treatment to iron chelation is expected to be effective in preventing and/or disrupting biofilm formation, and that under oxic conditions, it is effective not only with respect to *Pseudomonas aeruginosa* but also towards a wide range of bacteria alone or in combination with conventional antimicrobial treatments. Additionally, the above results also supports the conclusion that mixed- Fe(III)/Fe(II) chelation is expected to be significant under anoxic conditions (thought to be prevalent throughout the CF airways [51]), by preventing or disrupting biofilms. In particular under conditions in which cells revert to a planktonic lifestyle and therefore are expected to remain tolerant to conventional antibiotics due to slow anaerobic growth and physiological changes [22], treatment with combined Fe(II) chelator and Fe(III) chelators is expected to result in having those cells no longer protected from the host immune response, and possibly more readily cleared from the host environment.

In view of the above, according to a first approach interfering with viability of bacteria can be performed in vivo or in vitro by activating one or more Fe (II) chelators in the bacteria, and in particular a Fe (II) chelator in the form of a protein and/or a chemical compound in combination with activating one or more Fe(III) chelators possibly being an Fe(III)-chelating protein or Fe(III)-chelating compound. In particular the Fe (II) chelator can be FerroZine®, and the activating can be performed for example by delivering FerroZine® into the mucus environment of bacteria using an aerosol. In some embodiments the Fe (II) chelator is a host protein. activating a Fe (II) chelator comprises regulating of one or more host genes encoding a host Fe (II) chelator. According to the first approach According to the ninth approach the Fe(III) chelator can be a conalbumin According to the first approach, the Fe(III) chelator and the Fe(II) chelator are administered for a time and under condition to substantially prevents and/or disrupts biofilm growth. According to the first approach, the Fe(III) and Fe(II) chelators can be administered for a time and under condition to act synergistically to substantially prevent and/or disrupt biofilm growth. According to the first approach, the Fe(III) and Fe(II) chelators can be administered for a time and under condition to disrupt mature biofilms.

According to a second approach, treating cystic fibrosis can be performed with a comprising: administering a therapeutically effective amount of a composition comprising an Fe(II) chelator in combination with and an Fe(III) chelator to an individual. According to the second approach, the administering can be performed by way of an aerosol comprising the Fe(III) chelator and the Fe(II) chelator. According to the second approach, the Fe(II) chelator can be FerroZine®, and an amount FerroZine® and the therapeutically effective amount of the composition can range from 10-1000 µM. According to the eleventh approach, the Fe(II) chelator can be conalbumin, and the therapeutically effective amount of the composition can range from 10-1000 µM.

According to a third approach, interfering with viability of bacteria can be performed by a composition comprising one or more Fe(II) chelators and one or more an Fe(III) chelators and in particular FerroZine®, possibly comprised in the composition in an amount ranging between 10-1000 µM, and/or conalbumin, possibly comprised in the composition in an amount ranging between 10-1000 µM. According to the third approach, the composition can be formulated to reduce biofilm accumulation by greater than approximately 50%. According to the twelfth approach, the composition can be a pharmaceutical composition in for treatment of cystic fibrosis and possibly further comprise a suitable vehicle for administering and/or delivering the one or more agents to an individual. According to the third approach, the composition can be formulated for topical administration and in particular being in the form of aerosol.

The examples set forth above are provided to give those of ordinary skill in the art a complete disclosure and description of how to make and use the embodiments of the compounds, compositions, systems and methods of the disclosure, and are not intended to limit the scope of what the inventors regard as their disclosure. All patents and publications mentioned in the specification are indicative of the levels of skill of those skilled in the art to which the disclosure pertains.

The entire disclosure of each document cited (including patents, patent applications, journal articles, abstracts, laboratory manuals, books, or other disclosures) in the Background, Summary, Detailed Description, and Examples is hereby incorporated herein by reference. All references cited in this disclosure are incorporated by reference to the same extent as if each reference had been incorporated by reference in its entirety individually. However, if any inconsistency arises between a cited reference and the present disclosure, the present disclosure takes precedence.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the disclosure claimed. Thus, it should be understood that although the disclosure has been specifically disclosed by preferred embodiments, exemplary embodiments and optional features, modification and variation of the concepts herein disclosed can be resorted to by those skilled in the art upon the reading of the present disclosure, and that such modifications and variations are considered to be within the scope of this disclosure as defined by the appended claims.

It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

When a Markush group or other grouping is used herein, all individual members of the group and all combinations and possible subcombinations of the group are intended to be individually included in the disclosure. Every combination of components or materials described or exemplified herein can be used to practice the disclosure, unless otherwise stated. One of ordinary skill in the art will appreciate that methods, device elements, and materials other than those specifically exemplified can be employed in the practice of the disclosure without resort to undue experimentation. All art-known functional equivalents, of any such methods, device elements, and materials are intended to be included in this disclosure. Whenever a range is given in the specification, for example, a temperature range, a frequency range, a time range, or a composition range, all intermediate ranges and all sub-ranges, as well as, all individual values included in the ranges given are intended to be included in the disclosure. Any one or more individual members of a range or group disclosed herein can be excluded from a claim of this disclosure. The disclosure illustratively described herein suitably can be practiced in the absence of any element or elements, limitation or limitations which are not specifically disclosed herein.

A number of embodiments of the disclosure have been described. The specific embodiments provided herein are examples of useful embodiments of the disclosure and it will be apparent to one skilled in the art that the disclosure can be carried out using a large number of variations of the devices, device components, methods steps set forth in the present description. As will be obvious to one of skill in the art, methods and devices useful for the present methods can include a large number of optional composition and processing elements and steps.

In particular, it will be understood that various modifications may be made without departing from the spirit and scope of the present disclosure. Accordingly, other embodiments are within the scope of the following claims.

REFERENCES

1. Elble, R., *A simple and efficient procedure for transformation of yeasts*. Biotechniques, 1992. 13(1): p. 18-20.
2. Mavrodi, D. V., W. Blankenfeldt, and L. S. Thomashow, *Phenazine compounds in fluorescent Pseudomonas spp. biosynthesis and regulation*. Annu Rev Phytopathol, 2006. 44: p. 417-45.
3. Wang, Y., S. E. Kern, and D. K. Newman, *Endogenous phenazine antibiotics promote anaerobic survival of Pseudomonas aeruginosa via extracellular electron transfer*. J Bacteriol, 2010. 192(1): p. 365-9.
4. Moker, N., C. R. Dean, and J. Tao, *Pseudomonas aeruginosa increases formation of multidrug-tolerant persister cells in response to quorum-sensing signaling molecules*. J Bacteriol, 2010. 192(7): p. 1946-55.
5. Gibbs, C. R., *Characterization and application of ferrozine iron reagent as a ferrous iron indicator*. Analytical Chemistry, 1976. 48(8): p. 1197-1201.
6. Im, J., J. Lee, and F. E. Löffler, *Interference of ferric ions with ferrous iron quantification using the ferrozine assay*. Journal of microbiological methods, 2013. 95(3): p. 366-367.
7. Anastacio, A. S., et al., *Limitations of the ferrozine method for quantitative assay of mineral systems for ferrous and total iron*. Geochimica et Cosmochimica Acta, 2008. 72(20): p. 5001-5008.
8. Martell, A. E. and R. M. Smith, *Critical stability constants*. Vol. 6. 1989: Springer.
9. Morel, F. M. M. and J. G. Hering, *Principles and Applications of Aquatic Chemistry* 1993, New York, N.Y.: John Wiley & Sons.
10. Heydorn, A., et al., *Quantification of biofilm structures by the novel computer program COMSTAT*. Microbiology, 2000. 146 (Pt 10): p. 2395-407.
11. Banin, E., M. L. Vasil, and E. P. Greenberg, Iron and *Pseudomonas aeruginosa* biofilm formation. Proc Natl Acad Sci USA, 2005. 102(31): p. 11076-81.
12. Wang, Y., et al., *Phenazine-1-carboxylic acid promotes bacterial biofilm development via ferrous iron acquisition*. J Bacteriol, 2011. 193(14): p. 3606-17.
13. Corkery, K., *Inhalable drugs for systemic therapy*. Respir Care, 2000. 45(7): p. 831-5.
14. Ito, A., et al., *Increased antibiotic resistance of Escherichia coli in mature biofilms*. Appl Environ Microbiol, 2009. 75(12): p. 4093-100.
15. Moreau-Marquis, S., B. A. Stanton, and G. A. O'Toole, *Pseudomonas aeruginosa biofilm formation in the cystic fibrosis airway*. Pulmonary pharmacology & therapeutics, 2008. 21(4): p. 595-599.
16. Hunter, R. C., et al., *Ferrous iron is a significant component of bioavailable iron in cystic fibrosis airways*. MBio, 2013. 4(4): p. e00557-13.
17. Heydorn, A., et al., *Quantification of biofilm structures by the novel computer program COMSTAT*. Microbiology, 2000. 146: p. 2395-2407.
18. Merritt, P. A., T. Danhorn, and C. Fuqua, *Motility and chemotaxis in Agrobacterium tumefaciens surface attachment and Biofilm formation*. Journal of Bacteriology, 2007. 189(22): p. 8005-8014.
19. Rashid, M. H. and A. Kornberg, *Inorganic polyphosphate is needed for swimming, swarming, and twitching motilities of Pseudomonas aeruginosa*. Proc Natl Acad Sci USA, 2000. 97(9): p. 4885-90.
20. Dietrich, L. E. P., et al., *Redox-active antibiotics control gene expression and community behavior in divergent bacteria*. Science, 2008. 321(5893): p. 1203-1206.
21. Clark Jr., L. C., et al., *Continuous recording of blood oxygen tensions by polarography*. Journal of Applied Physiology, 1953. 6(3): p. 189-93.
22. Miller, M. R., et al., *General considerations for lung function testing*. Eur Respir J, 2005. 26(1): p. 153-61.
23. Flume, P. A., et al., *Cystic fibrosis pulmonary guidelines: chronic medications for maintenance of lung health*. Am J Respir Crit Care Med, 2007. 176(10): p. 957-69.
24. Tomlin, K. L., et al., *Quorum-sensing mutations affect attachment and stability of Burkholderia cenocepacia biofilms*. Appl Environ Microbiol, 2005. 71(9): p. 5208-18.
25. Fischbach, M. A., et al., *How pathogenic bacteria evade mammalian sabotage in the battle for iron*. Nature chemical biology, 2006. 2(3): p. 132-138.
26. Lim, Y. W., et al., *Metagenomics and metatranscriptomics: Windows on CF-associated viral and microbial communities*. Journal of Cystic Fibrosis, 2013. 12(2): p. 154-164.
27. Kreamer, N. N., et al., *BqsR/BqsS constitute a two-component system that senses extracellular Fe (II) in Pseudomonas aeruginosa*. Journal of Bacteriology, 2012. 194(5): p. 1195-1204.
28. De Vos, D., et al., *Direct detection and identification of Pseudomonas aeruginosa in clinical samples such as skin biopsy specimens and expectorations by multiplex PCR based on two outer membrane lipoprotein genes, oprI and oprL*. Journal of clinical microbiology, 1997. 35(6): p. 1295-1299.
29. Wolfgang, M. C., et al., *Pseudomonas aeruginosa regulates flagellin expression as part of a global response to airway fluid from cystic fibrosis patients*. Proceedings of the National Academy of Sciences of the United States of America, 2004. 101(17): p. 6664-6668.
30. Hunter, R. C., et al., *Phenazine content in the cystic fibrosis respiratory tract negatively correlates with lung function and microbial complexity*. Am J Respir Cell Mol Biol, 2012. 47(6): p. 738-45.
31. Rajan, S. and L. Saiman. *Pulmonary infections in patients with cystic fibrosis*. in Seminars in respiratory infections. 2002.
32. Reid, D., et al., *Increased airway iron as a potential factor in the persistence of Pseudomonas aeruginosa infection in cystic fibrosis*. European Respiratory Journal, 2007. 30(2): p. 286-292.
33. Stites, S. W., et al., *Increased iron and ferritin content of sputum from patients with cystic fibrosis or chronic bronchitis*. Chest, 1998. 114(3): p. 814-9.
34. Ghio, A. J., et al., *Iron accumulates in the lavage and explanted lungs of cystic fibrosis patients*. J Cyst Fibros, 2013. 12(4): p. 390-8.

35. Gifford, A. H., et al., *Iron homeostasis during cystic fibrosis pulmonary exacerbation*. Clin Transl Sci, 2012. 5(4): p. 368-73.
36. Mateos, F., J. H. Brock, and J. L. Perez-Arellano, *Iron metabolism in the lower respiratory tract*. Thorax, 1998. 53(7): p. 594-600.
37. Moreau-Marquis, S., et al., *The DeltaF508-CFTR mutation results in increased biofilm formation by Pseudomonas aeruginosa by increasing iron availability*. Am J Physiol Lung Cell Mol Physiol, 2008. 295(1): p. L25-37.
38. Miller, R. A. and B. E. Britigan, *Protease-cleaved iron-transferrin augments oxidant-mediated endothelial cell injury via hydroxyl radical formation*. J Clin Invest, 1995. 95(6): p. 2491-500.
39. Wang, Y. and D. K. Newman, *Redox reactions of phenazine antibiotics with ferric (hydr)oxides and molecular oxygen*. Environ Sci Technol, 2008. 42(7): p. 2380-6.
40. Bultreys, A., et al., *High-performance liquid chromatography analyses of pyoverdin siderophores differentiate among phytopathogenic fluorescent Pseudomonas species*. Applied and Environmental Microbiology, 2003. 69(2): p. 1143-1153.
41. Palmer, K. L., L. M. Aye, and M. Whiteley, *Nutritional cues control Pseudomonas aeruginosa multicellular behavior in cystic fibrosis sputum*. J Bacteriol, 2007. 189(22): p. 8079-87.
42. Konings, A. F., et al., *Pseudomonas aeruginosa uses multiple pathways to acquire iron during chronic infection in cystic fibrosis lungs*. Infect Immun, 2013. 81(8): p. 2697-704.
43. Panter, S. S., *Release of iron from hemoglobin*, 1993, DTIC Document.
44. Chen, X. and P. S. Stewart, *Role of electrostatic interactions in cohesion of bacterial biofilms*. Appl Microbiol Biotechnol, 2002. 59(6): p. 718-20.
45. Vasil, M. L. and U. A. Ochsner, *The response of Pseudomonas aeruginosa to iron: genetics, biochemistry and virulence*. Mol Microbiol, 1999. 34(3): p. 399-413.
46. Cornelis, P., S. Matthijs, and L. Van Oeffelen, *Iron uptake regulation in Pseudomonas aeruginosa*. Biometals, 2009. 22(1): p. 15-22.
47. Che, Y., et al., *Iron-binding compounds impair Pseudomonas aeruginosa biofilm formation, especially under anaerobic conditions*. Journal of medical microbiology, 2009. 58(6): p. 765-773.
48. Singh, P. K., *Iron sequestration by human lactoferrin stimulates P. aeruginosa surface motility and blocks biofilm formation*. Biometals, 2004. 17(3): p. 267-70.
49. Moreau-Marquis, S., G. A. O'Toole, and B. A. Stanton, *Tobramycin and FDA-approved iron chelators eliminate Pseudomonas aeruginosa biofilms on cystic fibrosis cells*. Am J Respir Cell Mol Biol, 2009. 41(3): p. 305-13.
50. Reid, D. W., G. J. Anderson, and I. L. Lamont, *Role of lung iron in determining the bacterial and host struggle in cystic fibrosis*. Am J Physiol Lung Cell Mol Physiol, 2009. 297(5): p. L795-802.
51. Worlitzsch, D., et al., *Effects of reduced mucus oxygen concentration in airway<i> Pseudomonas</i> infections of cystic fibrosis patients*. The Journal of clinical investigation, 2002. 109(3): p. 317-325.

The invention claimed is:

1. A method for interfering with viability of a bacterium in a medium, the method comprising
contacting the medium with an Fe(II) chelator selected from the group consisting of 1,10 phenanthroline and 3-(2-Pyridyl)-5,6-diphenyl-1,2,4-triazine-p,p'-disulfonic acid monosodium salt hydrate and an Fe(III) chelator selected from the group consisting of hemoglobin, transferrin, lactoferrin, conalbumin, EDTA, desferrinferrioxamine B, siderophores and ferritin to reduce survivability and/or antibiotic resistance of the bacterium in the medium.

2. The method of claim 1, wherein the Fe(II) chelator comprises 3-(2-Pyridyl)-5,6-diphenyl-1,2,4-triazine-p,p'-disulfonic acid monosodium salt hydrate and the Fe(III) chelator comprises conalbumin.

3. The method of claim 1, wherein the Fe(II) chelator and the Fe(III) chelator are provided in an amount that substantially inhibits and/or disrupts biofilm growth.

4. The method of claim 1, wherein the Fe(II) chelator and the Fe(III) chelator are in an amount of 10-1000 μM.

5. The method of claim 1, wherein the bacterium is *Pseudomonas aeruginosa*.

6. A method to minimize contamination of a surface from a bacterium, the method comprising
contacting the surface with an Fe(II) chelator selected from the group consisting of 1,10 phenanthroline and 3-(2-Pyridyl)-5,6-diphenyl-1,2,4-triazine-p,p'-disulfonic acid monosodium salt hydrate and an Fe(III) chelator selected from the group consisting of hemoglobin, transferrin, lactoferrin, conalbumin, EDTA, desferrinferrioxamine B, siderophores and ferritin optionally in combination with an antibiotic and/or other antimicrobial.

7. The method of claim 1, wherein the contacting is performed under hypoxic or anoxic condition.

8. The method of claim 1, wherein the medium comprises biofilm.

9. The method of claim 1, wherein the medium is in the lungs.

10. The method of claim 1, further comprising adding an antibiotic and/or an antimicrobial to the medium.

11. The method of claim 1, wherein the contacting is performed to reduce survivability and/or antibiotic resistance of the bacterium in vivo.

12. The method of claim 1, wherein the Fe(II) chelator is 3-(2-Pyridyl)-5,6-diphenyl-1,2,4-triazine-p,p'-disulfonic acid monosodium salt hydrate in an amount of 10-250 μM and the Fe(III) chelator is conalbumin in an amount of 10-250 μM.

13. The method of claim 1, wherein the Fe(II) chelator and the Fe(III) chelator are in an amount capable of reducing biofilm accumulation by greater than approximately 50%.

14. A method for interfering with viability of a bacterium in a medium, the method comprising
contacting the medium with an Fe(II) chelator selected from the group consisting of 1,10 phenanthroline and 3-(2-Pyridyl)-5,6-diphenyl-1,2,4-triazine-p,p'-disulfonic acid monosodium salt hydrate and an Fe(III) chelator selected from the group consisting of Trans-1,2-Cyclohexanediaminetetraacetic Acid, Nitrilotriacetic acid, iminodiacetic acid, and citrate conalbumin to reduce survivability and/or antibiotic resistance of the bacterium in the medium.

15. The method of claim 14, wherein the Fe(II) chelator and the Fe(III) chelator are provided in an amount that substantially inhibits and/or disrupts biofilm growth.

16. The method of claim 14, wherein the Fe(II) chelator and the Fe(III) chelator are in an amount of 10-1000 μM.

17. The method of claim 14, wherein the bacterium is *Pseudomonas aeruginosa*.

18. The method of claim 14, wherein the contacting is performed under hypoxic or anoxic condition.

19. The method of claim 14, wherein the medium comprises biofilm.

20. The method of claim 14, wherein the medium is in the lungs.

21. The method of claim 14, further comprising adding an antibiotic and/or an antimicrobial to the medium.

22. A method to minimize contamination of a surface from a bacterium, the method comprising
contacting the surface with an Fe(II) chelator selected from the group consisting of 1,10 phenanthroline and 3-(2-Pyridyl)-5,6-diphenyl-1,2,4-triazine-p,p'-disulfonic acid monosodium salt hydrate and an Fe(III) chelator selected from the group consisting of Trans-1,2-Cyclohexanediaminetetraacetic Acid, Nitrilotriacetic acid, iminodiacetic acid, and citrate conalbumin optionally in combination with an antibiotic and/or other antimicrobial.

* * * * *